(12) United States Patent
Dunn et al.

(10) Patent No.: US 12,325,752 B2
(45) Date of Patent: Jun. 10, 2025

(54) IMMUNOGLOBULIN PROTEINS THAT BIND TO NPR1 AGONISTS

(71) Applicant: REGENERON PHARMACEUTICALS, INC., Tarrytown, NY (US)

(72) Inventors: Michael E. Dunn, Montvale, NJ (US); Lori C. Morton, Chappaqua, NY (US); Neil Stahl, Carmel, NY (US); Tammy T. Huang, Cross River, NY (US); Ishita Chatterjee, Nanuet, NY (US); Vishal Kamat, Northbridge, MA (US); Ashique Rafique, Yonkers, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 17/554,276

(22) Filed: Dec. 17, 2021

(65) Prior Publication Data
US 2022/0195058 A1    Jun. 23, 2022

Related U.S. Application Data

(60) Provisional application No. 63/127,959, filed on Dec. 18, 2020.

(51) Int. Cl.
  *C07K 16/28*    (2006.01)
  *A61K 39/00*    (2006.01)
  *A61P 9/12*     (2006.01)
(52) U.S. Cl.
  CPC ............ *C07K 16/2869* (2013.01); *A61P 9/12* (2018.01); *A61K 2039/505* (2013.01);
  (Continued)

(58) Field of Classification Search
  CPC .......... C07K 16/2869; C07K 2317/565; C07K 2317/76; C07K 2317/92; A61P 9/12; A61K 2039/505
  See application file for complete search history.

(56) References Cited

U.S. PATENT DOCUMENTS

| | | | |
|---|---|---|---|
| 6,596,541 | B2 | 7/2003 | Murphy et al. |
| 7,582,298 | B2 | 9/2009 | Stevens et al. |

(Continued)

FOREIGN PATENT DOCUMENTS

| | | |
|---|---|---|
| WO | 91/17271 | 11/1991 |
| WO | 92/01047 | 1/1992 |

(Continued)

OTHER PUBLICATIONS

Kussie, Paul H., "A Single Engineered Amino Acid Substitution Changes Antibody Fine Specificity", 1994, Journal of Immunology 152(1): pp. 146-152. (Year: 1994).*

(Continued)

*Primary Examiner* — Aurora M Fontainhas
*Assistant Examiner* — Selam Berhane
(74) *Attorney, Agent, or Firm* — Merchant & Gould P.C.

(57) ABSTRACT

The present disclosure provides novel immunoglobulin proteins that bind to a human natriuretic peptide receptor 1 (NPR1) agonist, preferably an anti-NPR1 antibody. In certain embodiments, the proteins of the disclosure comprise at least one immunoglobulin variable domain that binds to an anti-NPR1 antibody. In certain embodiments, the proteins of the disclosure are useful in blocking and/or reversing the effect of an administered anti-NPR1 antibody. In certain embodiments, the antigen-binding proteins are useful for effective management of blood pressure and hemodynamics in humans.

44 Claims, 12 Drawing Sheets

Specification includes a Sequence Listing.

(52) U.S. Cl.
CPC .... *C07K 2317/565* (2013.01); *C07K 2317/76* (2013.01); *C07K 2317/92* (2013.01)

(56) References Cited

U.S. PATENT DOCUMENTS

| | | | |
|---|---|---|---|
| 8,246,995 | B2 | 8/2012 | Dai et al. |
| 8,257,740 | B1 | 9/2012 | Sung et al. |
| 9,090,695 | B2 | 7/2015 | Waterman et al. |
| 11,306,148 | B2 | 4/2022 | Dunn |
| 11,820,826 | B2 | 11/2023 | Dunn |
| 2004/0101920 | A1 | 5/2004 | Radziejewski et al. |
| 2010/0310561 | A1 | 12/2010 | Canada et al. |
| 2010/0331527 | A1 | 12/2010 | Davis et al. |
| 2011/0195454 | A1 | 8/2011 | McWhirter et al. |
| 2012/0114659 | A1 | 5/2012 | Waterman et al. |
| 2012/0270923 | A1 | 10/2012 | Mohapatra |
| 2014/0031234 | A1 | 1/2014 | Despres |
| 2014/0243504 | A1 | 8/2014 | Davis et al. |
| 2014/0343120 | A1 | 11/2014 | Mohapatra |
| 2016/0168251 | A1 | 6/2016 | Waterman et al. |
| 2016/0199487 | A1 | 7/2016 | Gu et al. |
| 2017/0355756 | A1* | 12/2017 | Julien .............. C07K 16/18 |
| 2020/0123263 | A1 | 4/2020 | Dunn |
| 2022/0204634 | A1 | 6/2022 | Dunn |
| 2023/0250170 | A1 | 8/2023 | Dunn |

FOREIGN PATENT DOCUMENTS

| | | | |
|---|---|---|---|
| WO | 2004/011618 | 2/2004 | |
| WO | 05/103081 | 11/2005 | |
| WO | WO-2008068048 A2 * | 6/2008 | .............. A61P 31/10 |
| WO | 2010/065293 | 6/2010 | |
| WO | 2016/131943 | 8/2016 | |
| WO | 2017/209553 | 12/2017 | |
| WO | 2018/075792 | 4/2018 | |
| WO | 2019/090039 | 5/2019 | |
| WO | 2020/086406 | 4/2020 | |
| WO | 2020/131935 | 6/2020 | |
| WO | 2020/250159 | 12/2020 | |
| WO | 2022/130182 | 6/2022 | |
| WO | 2022/133239 | 6/2022 | |

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Dondelinger, Mathieu, et al: "Understanding the Significance and Implications of Antibody Numbering and Antigen-Binding Surface/Residue Definition", Frontiers in Immunology, Oct. 16, 2018;9:Article 2278, 15 pages.

Blech, Michaela et al., "Structure of a Therapeutic Full-Length Anti-NPRA IgG4 Antibody: Dissecting Conformational Diversity", Biophys J. May 7, 2019; 116(9): 1637-1649, Published online Apr. 5, 2019. doi: 10.1016/j.bpj.2019.03.036.

Bostrom, Jenny et al: "Improving antibody binding affinity and specificity for therapeutic development", Methods Mol Biol. 2009;525:353-76, xiii. Doi: 10.1007/978-1-59745-554-1_19.

Gonzales, Noreen R., et al., "Minimizing the Immunogenicity of Antibodies for Clinical Application", Tumour Biol. Jan.-Feb. 2005;26(1):31-43. doi: 10.1159/000084184.

Kunik, Vered et al., "Structural consensus among antibodies defines the antigen binding site", PLoS Comput Biol. 2012;8(2):e1002388. doi: 10.1371/journal.pcbi.1002388.Epub Feb. 23, 2012.

Kussie, Paul H. et al., "A Single Engineered Amino Acid Substitution Changes Antibody Fine Specificity", Journal of Immunology, 1994, 152: 146-152.

Morris, Glenn E., "Epitope Mapping of Protein Antigens by Competition ELISA", The Protein Protocols Handbook, Totowa, NJ, Humana Press, (Jan. 1, 1996), pp. 595-600, doi: 10.1007/978-1-60327-259-9_96, ISBN 978-1-60-327259-9, DOI:http://dx.doi.org/10.1007/978-1-60327-259-9_96.

Panka, et al: "Variable region framework differences result in decreased or increased affinity of variant anti-digoxin antibodies", Proc Natl Acad Sci USA, May 1988;85(9):3080-4. doi: 10.1073/pnas.85.9.3080.

Rudikoff et al., "Single amino acid substitution altering antigen-binding specificity", Proc. Nat. Acad. Sci. USA vol. 79, pp. 1979-1983, Mar. 1982. DOI: 10.1073/pnas.79.6.1979.

Wark, KL et al., "Latest technologies for the enhancement of antibody affinity", Advanced Drug Delivery Reviews, Elsevier, vol. 58, No. 5-6,doi:10.1016/J.ADDR.2006.01.025, ISSN 0169-409X, (Aug. 7, 2006), pp. 657-670.

Benjamini, Eli, et al., "1991 Immunology: A Short Course", 2nd Edition, Wiley-Liss, Inc. New York, NY, USA, 1991, p. 40.

Ferrara, Fortunato, et al., "Recombinant renewable polyclonal antibodies", Jan./Feb. 2015 mAbs. 7(1): 32-41.

Garbers, David L. et al., "Membrane guanylyl cyclase receptors: an update", Trends in Endocrinology and Metabolism, vol. 17, No. 6, pp. 251-258.

Garbers, David L., The guanylyl cyclase receptors, Zygote 8 (Supplement) 2000, Cambridge Univ. Press, FDSUMI Symposium Proc., pp. S24-S25.

Kuhn, Michaela, (2003), "Structure, Regulation, and Function of Mammalian Membrane Guanylyl Cyclase Receptors, With a Focus on Guanylyl Cyclase-A", Circ. Res. 93: 700-709.

Lowe, D. G. et al., "Human natriuretic peptide receptor—A guanylyl cyclase. Hormone cross-linking and antibody reactivity distinguish receptor glycoforms", The Journal of Biological Chemistry, Oct. 25, 1992, vol. 267, No. 30, pp. 21691-21697.

Misono, Kunio S., (2011), Minireview, "Structure, signaling mechanism and regulation of the natriuretic peptide receptor guanylate cyclase", FEBS Journal 278: 1818-1829.

Mohapatra, Shyam S., (2007), "Role of natriuretic peptide signaling in modulating asthma and inflammation", Can. J. Physiol. Pharmacol. 85: 754-759.

Oliver, Paula M. et al., "Natriuretic peptide receptor 1 expression influences blood pressures of mice in a dose-dependent manner", Proc. Natl. Acad. Sci. USA, vol. 95, pp. 2547-2551, Mar. 1998.

Pandey, Kailash N., (2011), "The functional genomics of guanylyl cyclase/natriuretic peptide receptor-A: Perspectives and paradigms", Minireview, the FEBS Journal 278: 1792-1807.

Pandey, Kailash N., (2011), "Guanylyl cyclase / atrial natriuretic peptide receptor-A: role in the pathophysiology of cardiovascular regulation", Can. J. Physiol. Pharmacol. 89: 557-573.

Potter, Lincoln R. et al., (2006), "Natriuretic Peptides, Their Receptors, and Cyclic Guanosine Monophosphate-Dependent Signaling Functions", Endocrine Reviews 27(1): 47-72.

Potter, Lincoln R., "Guanylyl Cyclase-linked natriuretic Peptide Receptors: Structure and Regulation", The Journal of Biological Chemistry, vol. 276, No. 9, Issue of Mar. 2, 2001, pp. 6057-6060.

Potter, Lincoln R., "Regulation and Therapeutic Targeting of Peptide-Activated Receptor Guanylyl Cyclases", Pharmacology & Therapeutics 130 (2011) 71-82.

Saito, Yoshihiko et al., (2011), "Roles of guanylyl cyclase—A signaling in the cardiovascular system", Can. J. Physiol. Pharmacol. 89: 551-556.

Zhao, Zhilong, et al., (2013), "ANP-NPRA Signaling Pathway—A Potential Therapeutic Target for the Treatment of Malignancy", Critical Reviews in Eukaryotic Gene Expression, 23(2): 93-101.

PCT International Search Report and Written Opinion in International Application PCT/US2021/064073, mailed Apr. 13, 2022, 25 pgs.

(56) References Cited

OTHER PUBLICATIONS

Cruz, Dinna, "Midodrine: a selective [alpha]—adrenergic agonist for orthostatic hypotension and dialysis hypotension", Expert Opin Pharmacother, vol. 1, No. 4, May 1, 2000, pp. 835-840.

Luscher, Thomas, et al., "From 'essential' hypertension to intensive blood pressure lowering: the pros and cons of lower target values", European Heart Journal, vol. 38, No. 44, Nov. 21, 2017, pp. 3258-3271.

Regeneron Pharmaceuticals: "Study to Assess the Safety, Tolerability, and Pharmacokinetics of REGN5381 (an NPR1 Agonist) in Adult Humans—NCT04506645", Clinical trials.gov, Aug. 10, 2020, XP055905554, Retrieved from the Internet: URL:https://clinicaltrials.gov/ct2/show/NCT04506645, [retrieved on Mar. 25, 2022], 20 pgs.

Regeneron Pharmaceuticals: "A Study to Evaluate the Safety, Tolerability, Pharmacokinetics, and Pharmacodynamics of REGN9035 in Healthy Adult Volunteers and Mildly Hypertensive Participants—NCT05291546", Clinical Trials.gov, Mar. 22, 2022, XP055907382, Retrieved from the Internet: URL:https://clinicaltrials.gov/ct2/show/NCTO5291546?term=regn5381&draw=2&rank=2, [retrieved on Mar. 30, 2022], 10 pgs.

Kitano, Katsuhiko, et al., "Production and characterization of monoclonal antibodies against human natriuretic peptide receptor-A or-B", Immunology Letters, vol. 47, No. 3, Sep. 1, 1995, pp. 215-222.

Solinski, Hans Jurgen, et al., "Inhibition of natriuretic peptide receptor 1 reduces itch in mice", Sci Transl Med, vol. 11, No. 10, Jul. 10, 2019, 15 pages.

Caton, Andrew et al., "Influenza virus hemagglutinin-specific antibodies isolated from a combinatorial expression library are closely related to the immune response of the donor", Proc. Natl. Acad, Scl., USA, 87:6450-6454, No. 16, Aug. 1990.

Verbrugge, Frederik et al., "Altered Hemodynamics and End-Organ Damage in Heart Failure", Sep. 8, 2000, Circulation 142(10):998-1012.

Kymes, Steven et al., "Real-world droxidopa or midodrine treatment persistence in patients with neurogenic orthostatic hypotension or orthostatic hypotension", Autonomic Neuroscience: Basic and Clinical 225 (2020); 102659, 5 pages.

Branden, Carl et al., "Introduction to Protein Structure", 2nd edition, Shanghai science and Technology Press, Jan. 31, 2007, (cited Chinese document and corresponding p. 306 in the English version of the document), 9 pages combined.

Republica de Colombia, Ministry of Social Protection, Instituto Nacional de Vigilancia de Medicamentos y Alimentos (INVIMA), Resolution 2023026320 (a commercial authorization issued by the sanitary Colombian authority (INVIMA)) for droxidopa, published Jun. 15, 2023, including English translation of summarizing section, 5 pages.

U.S. Appl. No. 18/485,241 (Unpublished), entitled "Anti-NPR1 Antibodies and Uses Thereof", filed Oct. 11, 2023, 114 pgs.

Centers for Disease Control and Prevention, "High Blood Pressure Symptoms and Causes", last reviewed May 18, 2021, accessed online on Mar. 23, 2024 at: https://www.cdc.gov/bloodpressure/about.htm, 6 pages.

Inbal Sela-Culang et al., "The Structural Basis of Antibody-Antigen Recognition", Frontiers in Immunology, Oct. 8, 2013, vol. 4, Article 302, http://dx.doi.org/10.3389/fimmu.2013.00302, 13 pages.

* cited by examiner

SEQUENCE LISTING

```
<160> NUMBER OF SEQ ID NOS: 59

<210> SEQ ID NO 1
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcactt atatggtttg atggaggtta taaatactat     180
gcagactccg tgaagggccg attcaccatc tccagagaca attccaagaa cacgctgtat     240
ctccaaatga acagcctgag agccgacgac acggctgtgt attactgtgc gagaggttcc     300
gcagcagctg gccacgttcc gtttgactac tggggccagg gaatcctggt caccgtctcc     360
tca                                                                   363
```

<210> SEQ ID NO 2
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Phe Asp Gly Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Gly Ser Ala Ala Ala Gly His Val Pro Phe Asp Tyr Trp Gly
            100                 105                 110

Gln Gly Ile Leu Val Thr Val Ser Ser
        115                 120

<210> SEQ ID NO 3
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 3
ggattcacct tcagtagcta tggc                                              24

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 4

Gly Phe Thr Phe Ser Ser Tyr Gly
1               5

<210> SEQ ID NO 5
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5
atatggtttg atggaggtta taaa                                              24

```
<210> SEQ ID NO 6
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ile Trp Phe Asp Gly Gly Tyr Lys
1               5

<210> SEQ ID NO 7
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
gcgagaggtt ccgcagcagc tggccacgtt ccgtttgact ac                          42

<210> SEQ ID NO 8
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ala Arg Gly Ser Ala Ala Ala Gly His Val Pro Phe Asp Tyr
1               5                   10

<210> SEQ ID NO 9
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
gacatccaga tgacccagtc tccttccacc ctgtctgcat ctgtaggaga cagggtcacc        60
atcacttgtc gggccagtca gagtattagt agttggttgg cctggtatca gcagaaacca       120
gggaaagccc ctaagctcct gatctataag gcgtctagtt tagaaagtgg ggtcccatca       180
aggttcagcg gcagtggatc tgagacagaa ttcactctca ccatcagcag cctgcagcct       240
gatgattttg caacttatta ctgccaacag tataatagtt attggacgtt cggcccaggg       300
accaaggtgg aaatcaaa                                                     318

<210> SEQ ID NO 10
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10
```

-continued

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Glu Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Pro Gly Thr Lys Val Glu Ile Lys
            100                 105

<210> SEQ ID NO 11
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
cagagtatta gtagttgg                                                 18

<210> SEQ ID NO 12
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gln Ser Ile Ser Ser Trp
1               5

<210> SEQ ID NO 13
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13 aaggcgtct                                                            9

<210> SEQ ID NO 14
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Lys Ala Ser
1
```

<210> SEQ ID NO 15
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
caacagtata atagttattg gacg                                          24

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gln Gln Tyr Asn Ser Tyr Trp Thr
1               5

<210> SEQ ID NO 17
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

| | | | | | |
|---|---|---|---|---|---|
| caggtgcagc | tggtggagtc | tgggggaggc | gtggtccagc | ctgggaggtc | cctgagactc | 60 |
| tcctgtgcag | cgtctggatt | caccttcagt | agctatggca | tgcactgggt | ccgccaggct | 120 |
| ccaggcaagg | ggctggagtg | ggtggcactt | atatggtttg | atggaggtta | taaatactat | 180 |
| gcagactccg | tgaagggccg | attcaccatc | tccagagaca | attccaagaa | cacgctgtat | 240 |
| ctccaaatga | acagcctgag | agccgacgac | acggctgtgt | attactgtgc | gagaggttcc | 300 |
| gcagcagctg | gccacgttcc | gtttgactac | tggggccagg | gaatcctggt | caccgtctcc | 360 |
| tcagcctcca | ccaagggccc | atcggtcttc | cccctggcgc | cctgctccag | gagcacctcc | 420 |
| gagagcacag | ccgccctggg | ctgcctggtc | aaggactact | tccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacgaag | 600 |
| acctacacct | gcaacgtaga | tcacaagccc | agcaacacca | aggtggacaa | gagagttgag | 660 |
| tccaaatatg | gtcccccatg | cccacccttgc | ccagcacctg | agttcctggg | gggaccatca | 720 |
| gtcttcctgt | tccccccaaa | acccaaggac | actctcatga | tctcccggac | ccctgaggtc | 780 |
| acgtgcgtgg | tggtggacgt | gagccaggaa | gaccccgagg | tccagttcaa | ctggtacgtg | 840 |
| gatggcgtgg | aggtgcataa | tgccaagaca | aagccgcggg | aggagcagtt | caacagcacg | 900 |
| taccgtgtgg | tcagcgtcct | caccgtcctg | caccaggact | ggctgaacgg | caaggagtac | 960 |
| aagtgcaagg | tctccaacaa | aggcctcccg | tcctccatcg | agaaaaccat | ctccaaagcc | 1020 |
| aaagggcagc | cccgagagcc | acaggtgtac | accctgcccc | catcccagga | ggagatgacc | 1080 |
| aagaaccagg | tcagcctgac | ctgcctggtc | aaaggcttct | accccagcga | catcgccgtg | 1140 |

```
gagtgggaga gcaatgggca gccggagaac aactacaaga ccacgcctcc cgtgctggac    1200
tccgacggct ccttcttcct ctacagcagg ctcaccgtgg acaagagcag gtggcaggag    1260
gggaatgtct tctcatgctc cgtgatgcat gaggctctgc acaaccacta cacacagaag    1320
tccctctccc tgtctctggg taaatga                                          1347
```

<210> SEQ ID NO 18
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Phe Asp Gly Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Gly Ser Ala Ala Gly His Val Pro Phe Asp Tyr Trp Gly
            100                 105                 110

Gln Gly Ile Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
```

```
            305                 310                 315                 320
Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 19
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
gacatccaga tgacccagtc tccttccacc ctgtctgcat ctgtaggaga cagggtcacc      60
atcacttgtc gggccagtca gagtattagt agttggttgg cctggtatca gcagaaacca    120
gggaaagccc ctaagctcct gatctataag gcgtctagtt tagaaagtgg ggtcccatca    180
aggttcagcg gcagtggatc tgagacagaa ttcactctca ccatcagcag cctgcagcct    240
gatgattttg caacttatta ctgccaacag tataatagtt attggacgtt cggcccaggg    300
accaaggtgg aaatcaaacg aactgtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtt ag                       642

<210> SEQ ID NO 20
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
```

```
            35                  40                  45
Tyr Lys Ala Ser Ser Leu Glu Ser Gly Val Pro Ser Arg Phe Ser Gly
 50                  55                  60

Ser Gly Ser Glu Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Trp Thr
                 85                  90                  95

Phe Gly Pro Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 21
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21

```
caggtgcagc tgcaggagtc gggcccagga ctggtgaagc cttcggagac cctgtccctc      60
acctgcactg tctctggtgc ctccatcagt acttactact ggagctggat ccggcagccc     120
ccagggaagg gactggagtg gattgggtat atttattaca gtgggaccac taactacaat     180
ccctccctca gagtcgagt caccatttca gtagacacgt ccaagaacca gttctccctg     240
aaattgagct ctgtgaccgc tgcggacacg gccgtgtatt actgtgcgag agatagggt      300
ggctacgatg gggagtgggg ccagggaacc ctggtcaccg tctcctca               348
```

<210> SEQ ID NO 22
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Ala Ser Ile Ser Thr Tyr
             20                  25                  30

Tyr Trp Ser Trp Ile Arg Gln Pro Pro Gly Lys Gly Leu Glu Trp Ile
        35                  40                  45
```

```
Gly Tyr Ile Tyr Tyr Ser Gly Thr Thr Asn Tyr Asn Pro Ser Leu Lys
        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Asp Arg Gly Gly Tyr Asp Gly Glu Trp Gly Gln Gly Thr Leu Val
            100                 105                 110

Thr Val Ser Ser
        115

<210> SEQ ID NO 23
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
ggtgcctcca tcagtactta ctac                                          24

<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Ala Ser Ile Ser Thr Tyr Tyr
 1               5

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
atttattaca gtgggaccac t                                             21

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ile Tyr Tyr Ser Gly Thr Thr
 1               5

<210> SEQ ID NO 27
<211> LENGTH: 30
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 27
gcgagagata ggggtggcta cgatggggag                                    30

<210> SEQ ID NO 28
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ala Arg Asp Arg Gly Gly Tyr Asp Gly Glu
1               5                   10

<210> SEQ ID NO 29
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29
gacatcgtga tgacccagtc tccagactcc ctggctgtgt ctctgggcga gagggccacc    60
atcaactgca agtccagcca gagtgtttta tacagctcca acaataagaa ctacttaact   120
tggtaccagc agaaaccagg acagcctcct aagctgctca tttactgggc gtctacccgg   180
gaatccgggg tccctgaccg attcagtggc agcgggtctg ggacagattt cactctcacc   240
atcagcagcc tgcaggctga agatgtggca gtttattact gtcagcaata ttatactact   300
ccgttcactt tcggcggagg gaccaaggtg gagatcaaa                          339

<210> SEQ ID NO 30
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Phe Thr Phe Gly Gly Gly Thr Lys Val Glu Ile
```

Lys

<210> SEQ ID NO 31
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
cagagtgttt tatacagctc caacaataag aactac                                    36

<210> SEQ ID NO 32
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gln Ser Val Leu Tyr Ser Ser Asn Asn Lys Asn Tyr
1               5                   10

<210> SEQ ID NO 33
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33 tgggcgtct                                                                   9

<210> SEQ ID NO 34
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Trp Ala Ser
1

<210> SEQ ID NO 35
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
cagcaatatt atactactcc gttcact                                               27

<210> SEQ ID NO 36
<211> LENGTH: 9

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gln Gln Tyr Tyr Thr Thr Pro Phe Thr
1               5

<210> SEQ ID NO 37
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
caggtgcagc tgcaggagtc gggcccagga ctggtgaagc cttcggagac cctgtccctc      60
acctgcactg tctctggtgc ctccatcagt acttactact ggagctggat ccggcagccc     120
ccagggaagg gactggagtg gattgggtat atttattaca gtgggaccac taactacaat     180
ccctccctca gagtcgagt caccatttca gtagacacgt ccaagaacca gttctccctg     240
aaattgagct ctgtgaccgc tgcggacacg gccgtgtatt actgtgcgag atagggggt    300 ggctacgatg gggagtgggg ccagggaacc ctggtcaccg tctcctcagc ctccaccaag     360
ggcccatcgg tcttcccct ggcgccctgc tccaggagca cctccgagag cacagccgcc     420
ctgggctgcc tggtcaagga ctacttcccc gaaccggtga cggtgtcgtg aactcaggc     480 gccctgacca gcggcgtgca caccttcccg gctgtcctac agtcctcagg actctactcc     540
ctcagcagcg tggtgaccgt gccctccagc agcttgggca cgaagaccta cacctgcaac     600
gtagatcaca gcccagcaa caccaaggtg gacaagagag ttgagtccaa atatggtccc     660
ccatgcccac cctgcccagc acctgagttc ctggggggac catcagtctt cctgttcccc     720
ccaaaaccca aggacactct catgatctcc cggacccctg aggtcacgtg cgtggtggtg     780
gacgtgagcc aggaagaccc cgaggtccag ttcaactggt acgtggatgg cgtggaggtg     840
cataatgcca agacaaagcc gcgggaggag cagttcaaca gcacgtaccg tgtggtcagc     900
gtcctcaccg tcctgcacca ggactggctg aacggcaagg agtacaagtg caaggtctcc     960
aacaaaggcc tcccgtcctc catcgagaaa accatctcca aagccaaagg gcagccccga    1020
gagccacagg tgtacaccct gcccccatcc caggaggaga tgaccaagaa ccaggtcagc    1080
ctgacctgcc tggtcaaagg cttctacccc agcgacatcg ccgtggagtg ggagagcaat    1140
gggcagccgg agaacaacta caagaccacg cctcccgtgc tggactccga cggctccttc    1200
ttcctctaca gcaggctcac cgtggacaag agcaggtggc aggagggaa tgtcttctca    1260 tgctccgtga tgcatgaggc tctgcacaac cactacacac agaagtccct ctccctgtct    1320
ctgggtaaat ga                                                        1332

<210> SEQ ID NO 38
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Thr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Arg Gly Gly Tyr Asp Gly Glu Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly

```
                    405                 410                 415
Asn Val Phe Ser Cys Ser Val Met His Glu Ala Leu His Asn His Tyr
            420                 425                 430

Thr Gln Lys Ser Leu Ser Leu Ser Leu Gly Lys
            435                 440

<210> SEQ ID NO 39
<211> LENGTH: 663
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39
gacatcgtga tgacccagtc tccagactcc ctggctgtgt ctctgggcga gagggccacc      60
atcaactgca agtccagcca gagtgtttta tacagctcca acaataagaa ctacttaact     120
tggtaccagc agaaaccagg acagcctcct aagctgctca tttactgggc gtctacccgg     180
gaatccgggg tccctgaccg attcagtggc agcgggtctg ggacagattt cactctcacc     240
atcagcagcc tgcaggctga agatgtggca gtttattact gtcagcaata ttatactact     300
ccgttcactt tcggcggagg gaccaaggtg gagatcaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
tag                                                                   663

<210> SEQ ID NO 40
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Phe Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125
```

```
Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 41
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
caggtgcagc tggtggagtc tgggggaggc gtggtccagc ctggggaggtc cctgagactc     60 tcctgtgcag cgtctggatt caccttcagt agctatggca tgcactgggt ccgccaggct    120
ccaggcaagg ggctggagtg ggtggcactt atatggtttg atggaggtta taaatactat    180
gcagactccg tgaagggccg attcaccatc tccagagaca attccaagaa cacgctgtat    240
ctccaaatga acagcctgag agccgacgac acggctgtgt attactgtgc gagaggttcc    300
gcagcagctg gccacgttcc gtttgactac tggggccagg gaatcctggt caccgtctcc    360
tcagccagca caaaggtcc tagcgttttt ccacttgccc catgttcaag gtcaacctcc    420
gaaagtaccg ccgctcttgg ctgtctcgta aaagattatt ttcccgaacc tgtaactgtc    480
tcctggaact ccggcgcact cacttccggc gtacatacct ccccgctgt cctccaatct    540 tccggtctct actccctgtc ttctgttgtc actgttccat catcctcact cggcacaaaa    600
acatatacct gcaacgttga tcacaagcca gtaataccaa agttgataag cgcgtcgaa    660 tccaaatacg gtcccccctg ccccccatgt cccgctccag gtttctcgg tggcccctct    720 gttttccttt ttcccccctaa acccaaagat accctcatga tttccagaac cccgaggtc    780 acctgcgtcg tcgttgatgt aagccaagaa gatcccgaag tccagttcaa ttggtatgta    840
gacggtgttg aagtccataa tgcaaaaaca aaacccagag aggaacagtt taattcaacc    900
tatcgtgtcg ttagcgtact caccgttctt catcaagact ggctcaatgg aaaagaatat    960
aaatgtaaag ttagcaacaa aggtctgccc agttcaatcg aaaaaacaat tagcaaagcc   1020
aaaggccaac ctcgcgaacc ccaagtctat accttgcccc cttctcagga gaaatgacc   1080 aaaaaccaag tttcactcac atgcctcgta aaaggattct atccatcaga cattgcagta   1140
gaatgggaat ctaacggcca acctgaaaat aattacaaaa ccactcctcc tgtcctcgat   1200
tctgacggct cttttttcct ttactccaga ttgactgttg ataaatcccg ctggcaggaa   1260
ggtaacgttt tttcttgttc tgtgatgcac gaagccctcc ataacagatt cactcaaaaa   1320
tctctttctc tctcccctgg caaataa                                       1347

<210> SEQ ID NO 42
```

<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Leu Ile Trp Phe Asp Gly Gly Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Gly Ser Ala Ala Gly His Val Pro Phe Asp Tyr Trp Gly
            100                 105                 110

Gln Gly Ile Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

```
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
            420                 425                 430
Leu His Asn Arg Phe Thr Gln Lys Ser Leu Ser Leu Ser Pro Gly Lys
        435                 440                 445
```

```
<210> SEQ ID NO 43
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43
caggtgcagc tgcaggagtc gggcccagga ctggtgaagc cttcggagac cctgtccctc      60
acctgcactg tctctggtgc ctccatcagt acttactact ggagctggat ccggcagccc     120
ccagggaagg gactggagtg gattgggtat atttattaca gtgggaccac taactacaat     180
ccctccctca gagtcgagt caccatttca gtagacacgt ccaagaacca gttctccctg      240
aaattgagct ctgtgaccgc tgcggacacg gccgtgtatt actgtgcgag agatagggggt    300 ggctacgatg gggagtgggg ccagggaacc ctggtcaccg tctcctcagc cagcacaaaa    360
ggtcctagcg ttttccact tgccccatgt tcaaggtcaa cctccgaaag taccgccgct      420
cttggctgtc tcgtaaaaga ttattttccc gaacctgtaa ctgtctcctg gaactccggc    480
gcactcactt ccggcgtaca taccttcccc gctgtcctcc aatcttccgg tctctactcc    540
ctgtcttctg ttgtcactgt tccatcatcc tcactcggca caaaaacata tacctgcaac    600
gttgatcaca gccaagtaa taccaaagtt gataagcgcg tcgaatccaa atacggtccc     660
ccctgccccc catgtcccgc tccagagttt ctcggtggcc cctctgtttt ccttttttccc    720 cctaaaccca agatacccct catgatttcc agaaccccc g aggtcacctg cgtcgtcgtt     780
gatgtaagcc aagaagatcc cgaagtccag ttcaattggt atgtagacgg tgttgaagtc    840
cataatgcaa aaacaaaacc cagagaggaa cagtttaatt caacctatcg tgtcgttagc    900
gtactcaccg ttcttcatca agactggctc aatggaaaag aatataaatg taaagttagc    960
aacaaaggtc tgcccagttc aatcgaaaaa acaattagca aagccaaagg ccaacctcgc    1020
gaaccccaag tctataccctt gccccctcct caggaagaaa tgaccaaaaa ccaagtttca    1080
ctcacatgcc tcgtaaaagg attctatcca tcagacattg cagtagaatg ggaatctaac    1140
ggccaacctg aaaataatta caaaaccact cctcctgtcc tcgattctga cggctctttt    1200
ttcctttact ccagattgac tgttgataaa tcccgctggc aggaaggtaa cgttttttct    1260
tgttctgtga tgcacgaagc cctccataac agattcactc aaaaatctct ttctctctcc    1320
cctggcaaat aa                                                        1332
```

```
<210> SEQ ID NO 44
<211> LENGTH: 443
<212> TYPE: PRT
<213> ORGANISM: Artificial Sequence
<220> FEATURE:
```

<221> NAME/KEY: source
<223> OTHER INFORMATION: /note="Description of Artificial Sequence: Synthetic polypeptide"

<400> SEQUENCE: 44

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Ala Ser Ile Ser Thr Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Gly Thr Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Asp Arg Gly Gly Tyr Asp Gly Glu Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Cys Ser Arg Ser Thr Ser Glu Ser Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Lys Thr Tyr Thr Cys Asn Val Asp His Lys Pro Ser Asn Thr
        195                 200                 205
Lys Val Asp Lys Arg Val Glu Ser Lys Tyr Gly Pro Pro Cys Pro Pro
    210                 215                 220
Cys Pro Ala Pro Glu Phe Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser Gln Glu Asp Pro Glu Val Gln Phe Asn
            260                 265                 270
Trp Tyr Val Asp Gly Val Glu Val His Asn Ala Lys Thr Lys Pro Arg
        275                 280                 285
Glu Glu Gln Phe Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Ala Lys
                325                 330                 335
Gly Gln Pro Arg Glu Pro Gln Val Tyr Thr Leu Pro Pro Ser Gln Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
```

```
385                 390                 395                 400
Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn Arg Phe
            420                 425                 430

Thr Gln Lys Ser Leu Ser Leu Ser Pro Gly Lys
        435                 440
```

<210> SEQ ID NO 45
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45

```
gagtccaaat atggtccccc atgcccaccc tgcccagcac ctgagttcct ggggggacca      60
tcagtcttcc tgttcccccc aaaacccaag gacactctca tgatctcccg gacccctgag     120
gtcacgtgcg tggtggtgga cgtgagccag gaagaccccg aggtccagtt caactggtac     180
gtggatggcg tggaggtgca taatgccaag acaaagccgc gggaggagca gttcaacagc     240
acgtaccgtg tggtcagcgt cctcaccgtc ctgcaccagg actggctgaa cggcaaggag     300
tacaagtgca aggtctccaa caaaggcctc ccgtcctcca tcgagaaaac catctccaaa     360
gccaaagggc agccccgaga gccacaggtg tacaccctgc ccccatccca ggaggagatg     420
accaagaacc aggtcagcct gacctgcctg gtcaaaggct tctacccag cgacatcgcc      480
gtggagtggg agagcaatgg gcagccggag aacaactaca agaccacgcc tcccgtgctg     540
gactccgacg gctccttctt cctctacagc aggctcaccg tggacaagag caggtggcag     600
gaggggaatg tcttctcatg ctccgtgatg catgaggctc tgcacaacca ctacacacag     660
aagtccctct ccctgtctct gggtaaatga                                      690
```

<210> SEQ ID NO 46
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110
```

```
Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 47
<211> LENGTH: 469
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gly Asn Leu Thr Val Ala Val Val Leu Pro Leu Ala Asn Thr Ser Tyr
1               5                   10                  15

Pro Trp Ser Trp Ala Arg Val Gly Pro Ala Val Glu Leu Ala Leu Ala
            20                  25                  30

Gln Val Lys Ala Arg Pro Asp Leu Leu Pro Gly Trp Thr Val Arg Thr
        35                  40                  45

Val Leu Gly Ser Ser Glu Asn Ala Leu Gly Val Cys Ser Asp Thr Ala
    50                  55                  60

Ala Pro Leu Ala Ala Val Asp Leu Lys Trp Glu His Asn Pro Ala Val
65                  70                  75                  80

Phe Leu Gly Pro Gly Cys Val Tyr Ala Ala Pro Val Gly Arg Phe
            85                  90                  95

Thr Ala His Trp Arg Val Pro Leu Leu Thr Ala Gly Ala Pro Ala Leu
            100                 105                 110

Gly Phe Gly Val Lys Asp Glu Tyr Ala Leu Thr Thr Arg Ala Gly Pro
            115                 120                 125

Ser Tyr Ala Lys Leu Gly Asp Phe Val Ala Ala Leu His Arg Arg Leu
            130                 135                 140

Gly Trp Glu Arg Gln Ala Leu Met Leu Tyr Ala Tyr Arg Pro Gly Asp
145                 150                 155                 160

Glu Glu His Cys Phe Phe Leu Val Glu Gly Leu Phe Met Arg Val Arg
                165                 170                 175

Asp Arg Leu Asn Ile Thr Val Asp His Leu Glu Phe Ala Glu Asp Asp
            180                 185                 190

Leu Ser His Tyr Thr Arg Leu Leu Arg Thr Met Pro Arg Lys Gly Arg
            195                 200                 205

Val Ile Tyr Ile Cys Ser Ser Pro Asp Ala Phe Arg Thr Leu Met Leu
210                 215                 220
```

```
Leu Ala Leu Glu Ala Gly Leu Cys Gly Glu Asp Tyr Val Phe Phe His
225                 230                 235                 240

Leu Asp Ile Phe Gly Gln Ser Leu Gln Gly Gly Gln Gly Pro Ala Pro
            245                 250                 255

Arg Arg Pro Trp Glu Arg Gly Asp Gly Gln Asp Val Ser Ala Arg Gln
        260                 265                 270

Ala Phe Gln Ala Ala Lys Ile Ile Thr Tyr Lys Asp Pro Asp Asn Pro
    275                 280                 285

Glu Tyr Leu Glu Phe Leu Lys Gln Leu Lys His Leu Ala Tyr Glu Gln
290                 295                 300

Phe Asn Phe Thr Met Glu Asp Gly Leu Val Asn Thr Ile Pro Ala Ser
305                 310                 315                 320

Phe His Asp Gly Leu Leu Tyr Ile Gln Ala Val Thr Glu Thr Leu
            325                 330                 335

Ala His Gly Gly Thr Val Thr Asp Gly Glu Asn Ile Thr Gln Arg Met
            340                 345                 350

Trp Asn Arg Ser Phe Gln Gly Val Thr Gly Tyr Leu Lys Ile Asp Ser
            355                 360                 365

Ser Gly Asp Arg Glu Thr Asp Phe Ser Leu Trp Asp Met Asp Pro Glu
370                 375                 380

Asn Gly Ala Phe Arg Val Val Leu Asn Tyr Asn Gly Thr Ser Gln Glu
385                 390                 395                 400

Leu Val Ala Val Ser Gly Arg Lys Leu Asn Trp Pro Leu Gly Tyr Pro
                405                 410                 415

Pro Pro Asp Ile Pro Lys Cys Gly Phe Asp Asn Glu Asp Pro Ala Cys
            420                 425                 430

Asn Gln Asp His Leu Ser Thr Leu Glu Glu Gln Lys Leu Ile Ser Glu
            435                 440                 445

Glu Asp Leu Gly Gly Glu Gln Lys Leu Ile Ser Glu Glu Asp Leu His
    450                 455                 460

His His His His
465

<210> SEQ ID NO 48
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Lys Pro Asn Ser Gly Gly Thr Asn Ser Ala Gln Arg Phe
    50                  55                  60

Gln Gly Arg Ile Thr Met Thr Trp Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ser Arg Gly Gly Pro Val Met Asn Tyr Tyr Tyr Tyr Tyr Gly Met Asp
```

100                 105                 110
Val Trp Gly Gln Gly Thr Thr Val Thr Val Ser Ser
        115                 120

<210> SEQ ID NO 49
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Tyr Thr Phe Thr Asp Tyr Tyr
1               5

<210> SEQ ID NO 50
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ile Lys Pro Asn Ser Gly Gly Thr
1               5

<210> SEQ ID NO 51
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ser Arg Gly Gly Pro Val Met Asn Tyr Tyr Tyr Tyr Tyr Gly Met Asp
1               5                   10                  15

Val

<210> SEQ ID NO 52
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Lys Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Thr
                85                  90                  95

Phe Gly Gln Gly Thr Arg Leu Glu Ile Lys
            100                 105

<210> SEQ ID NO 53
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gln Ser Ile Asp Ser Tyr
1               5

<210> SEQ ID NO 54
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Val Ala Ser
1

<210> SEQ ID NO 55
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gln Gln Ser Tyr Ser Ile Pro Thr
1               5

<210> SEQ ID NO 56
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Lys Pro Asn Ser Gly Gly Thr Asn Ser Ala Gln Arg Phe
    50                  55                  60

Gln Gly Arg Ile Thr Met Thr Trp Asp Thr Ser Ile Ser Thr Ala Tyr
65                  70                  75                  80

Met Glu Leu Ser Arg Leu Arg Ser Asp Asp Thr Ala Val Tyr Tyr Cys

```
                    85                  90                  95
Ser Arg Gly Gly Pro Val Met Asn Tyr Tyr Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 57
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 57

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Lys Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Thr
                85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 58
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn Arg Phe Thr Gln Lys Ser Leu Ser
210                 215                 220

Leu Ser Pro Gly Lys
225

<210> SEQ ID NO 59
<211> LENGTH: 1061
<212> TYPE: PRT
<213> ORGANISM: Homo sapiens

<400> SEQUENCE: 59

Met Pro Gly Pro Arg Arg Pro Ala Gly Ser Arg Leu Arg Leu Leu Leu
1               5                   10                  15

Leu Leu Leu Leu Pro Pro Leu Leu Leu Leu Arg Gly Ser His Ala
            20                  25                  30

Gly Asn Leu Thr Val Ala Val Leu Pro Leu Ala Asn Thr Ser Tyr
            35                  40                  45

Pro Trp Ser Trp Ala Arg Val Gly Pro Ala Val Glu Leu Ala Leu Ala
        50                  55                  60

Gln Val Lys Ala Arg Pro Asp Leu Leu Pro Gly Trp Thr Val Arg Thr
65                  70                  75                  80

Val Leu Gly Ser Ser Glu Asn Ala Leu Gly Val Cys Ser Asp Thr Ala
                85                  90                  95

Ala Pro Leu Ala Ala Val Asp Leu Lys Trp Glu His Asn Pro Ala Val
            100                 105                 110

Phe Leu Gly Pro Gly Cys Val Tyr Ala Ala Ala Pro Val Gly Arg Phe
        115                 120                 125

Thr Ala His Trp Arg Val Pro Leu Leu Thr Ala Gly Ala Pro Ala Leu
        130                 135                 140

Gly Phe Gly Val Lys Asp Glu Tyr Ala Leu Thr Thr Arg Ala Gly Pro
145                 150                 155                 160

Ser Tyr Ala Lys Leu Gly Asp Phe Val Ala Ala Leu His Arg Arg Leu
                165                 170                 175

Gly Trp Glu Arg Gln Ala Leu Met Leu Tyr Ala Tyr Arg Pro Gly Asp
            180                 185                 190

Glu Glu His Cys Phe Phe Leu Val Glu Gly Leu Phe Met Arg Val Arg
        195                 200                 205

Asp Arg Leu Asn Ile Thr Val Asp His Leu Glu Phe Ala Glu Asp Asp
        210                 215                 220

Leu Ser His Tyr Thr Arg Leu Leu Arg Thr Met Pro Arg Lys Gly Arg
225                 230                 235                 240

Val Ile Tyr Ile Cys Ser Ser Pro Asp Ala Phe Arg Thr Leu Met Leu
                245                 250                 255

```
Leu Ala Leu Glu Ala Gly Leu Cys Gly Glu Asp Tyr Val Phe Phe His
            260                 265                 270
Leu Asp Ile Phe Gly Gln Ser Leu Gln Gly Gln Gly Pro Ala Pro
            275                 280                 285
Arg Arg Pro Trp Glu Arg Gly Asp Gly Gln Asp Val Ser Ala Arg Gln
290                 295                 300
Ala Phe Gln Ala Ala Lys Ile Ile Thr Tyr Lys Asp Pro Asp Asn Pro
305                 310                 315                 320
Glu Tyr Leu Glu Phe Leu Lys Gln Leu Lys His Leu Ala Tyr Glu Gln
            325                 330                 335
Phe Asn Phe Thr Met Glu Asp Gly Leu Val Asn Thr Ile Pro Ala Ser
            340                 345                 350
Phe His Asp Gly Leu Leu Leu Tyr Ile Gln Ala Val Thr Glu Thr Leu
            355                 360                 365
Ala His Gly Gly Thr Val Thr Asp Gly Glu Asn Ile Thr Gln Arg Met
    370                 375                 380
Trp Asn Arg Ser Phe Gln Gly Val Thr Gly Tyr Leu Lys Ile Asp Ser
385                 390                 395                 400
Ser Gly Asp Arg Glu Thr Asp Phe Ser Leu Trp Asp Met Asp Pro Glu
                405                 410                 415
Asn Gly Ala Phe Arg Val Val Leu Asn Tyr Asn Gly Thr Ser Gln Glu
            420                 425                 430
Leu Val Ala Val Ser Gly Arg Lys Leu Asn Trp Pro Leu Gly Tyr Pro
            435                 440                 445
Pro Pro Asp Ile Pro Lys Cys Gly Phe Asp Asn Glu Asp Pro Ala Cys
450                 455                 460
Asn Gln Asp His Leu Ser Thr Leu Glu Val Leu Ala Leu Val Gly Ser
465                 470                 475                 480
Leu Ser Leu Leu Gly Ile Leu Ile Val Ser Phe Phe Ile Tyr Arg Lys
                485                 490                 495
Met Gln Leu Glu Lys Glu Leu Ala Ser Glu Leu Trp Arg Val Arg Trp
            500                 505                 510
Glu Asp Val Glu Pro Ser Ser Leu Glu Arg His Leu Arg Ser Ala Gly
            515                 520                 525
Ser Arg Leu Thr Leu Ser Gly Arg Gly Ser Asn Tyr Gly Ser Leu Leu
            530                 535                 540
Thr Thr Glu Gly Gln Phe Gln Val Phe Ala Lys Thr Ala Tyr Tyr Lys
545                 550                 555                 560
Gly Asn Leu Val Ala Val Lys Arg Val Asn Arg Lys Arg Ile Glu Leu
                565                 570                 575
Thr Arg Lys Val Leu Phe Glu Leu Lys His Met Arg Asp Val Gln Asn
            580                 585                 590
Glu His Leu Thr Arg Phe Val Gly Ala Cys Thr Asp Pro Pro Asn Ile
            595                 600                 605
Cys Ile Leu Thr Glu Tyr Cys Pro Arg Gly Ser Leu Gln Asp Ile Leu
            610                 615                 620
Glu Asn Glu Ser Ile Thr Leu Asp Trp Met Phe Arg Tyr Ser Leu Thr
625                 630                 635                 640
Asn Asp Ile Val Lys Gly Met Leu Phe Leu His Asn Gly Ala Ile Cys
                645                 650                 655
Ser His Gly Asn Leu Lys Ser Ser Asn Cys Val Val Asp Gly Arg Phe
            660                 665                 670
```

-continued

Val Leu Lys Ile Thr Asp Tyr Gly Leu Glu Ser Phe Arg Asp Leu Asp
            675                 680                 685

Pro Glu Gln Gly His Thr Val Tyr Ala Lys Lys Leu Trp Thr Ala Pro
690                 695                 700

Glu Leu Leu Arg Met Ala Ser Pro Val Arg Gly Ser Gln Ala Gly
705                 710                 715                 720

Asp Val Tyr Ser Phe Gly Ile Ile Leu Gln Glu Ile Ala Leu Arg Ser
            725                 730                 735

Gly Val Phe His Val Glu Gly Leu Asp Leu Ser Pro Lys Glu Ile Ile
            740                 745                 750

Glu Arg Val Thr Arg Gly Glu Gln Pro Pro Phe Arg Pro Ser Leu Ala
            755                 760                 765

Leu Gln Ser His Leu Glu Glu Leu Gly Leu Leu Met Gln Arg Cys Trp
770                 775                 780

Ala Glu Asp Pro Gln Glu Arg Pro Pro Phe Gln Gln Ile Arg Leu Thr
785                 790                 795                 800

Leu Arg Lys Phe Asn Arg Glu Asn Ser Ser Asn Ile Leu Asp Asn Leu
            805                 810                 815

Leu Ser Arg Met Glu Gln Tyr Ala Asn Asn Leu Glu Glu Leu Val Glu
            820                 825                 830

Glu Arg Thr Gln Ala Tyr Leu Glu Glu Lys Arg Lys Ala Glu Ala Leu
835                 840                 845

Leu Tyr Gln Ile Leu Pro His Ser Val Ala Glu Gln Leu Lys Arg Gly
850                 855                 860

Glu Thr Val Gln Ala Glu Ala Phe Asp Ser Val Thr Ile Tyr Phe Ser
865                 870                 875                 880

Asp Ile Val Gly Phe Thr Ala Leu Ser Ala Glu Ser Thr Pro Met Gln
            885                 890                 895

Val Val Thr Leu Leu Asn Asp Leu Tyr Thr Cys Phe Asp Ala Val Ile
            900                 905                 910

Asp Asn Phe Asp Val Tyr Lys Val Glu Thr Ile Gly Asp Ala Tyr Met
            915                 920                 925

Val Val Ser Gly Leu Pro Val Arg Asn Gly Arg Leu His Ala Cys Glu
930                 935                 940

Val Ala Arg Met Ala Leu Ala Leu Leu Asp Ala Val Arg Ser Phe Arg
945                 950                 955                 960

Ile Arg His Arg Pro Gln Glu Gln Leu Arg Leu Arg Ile Gly Ile His
            965                 970                 975

Thr Gly Pro Val Cys Ala Gly Val Val Gly Leu Lys Met Pro Arg Tyr
            980                 985                 990

Cys Leu Phe Gly Asp Thr Val Asn Thr Ala Ser Arg Met Glu Ser Asn
            995                 1000                1005

Gly Glu Ala Leu Lys Ile His Leu Ser Ser Glu Thr Lys Ala Val
        1010            1015               1020

Leu Glu Glu Phe Gly Gly Phe Glu Leu Glu Leu Arg Gly Asp Val
        1025            1030              1035

Glu Met Lys Gly Lys Gly Lys Val Arg Thr Tyr Trp Leu Leu Gly
        1040            1045              1050

Glu Arg Gly Ser Ser Thr Arg Gly
        1055            1060

IMMUNOGLOBULIN PROTEINS THAT BIND TO NPR1 AGONISTS

CROSS-REFERENCE TO RELATED APPLICATIONS

This application claims priority to U.S. Provisional Patent Application No. 63/127,959, filed Dec. 18, 2020, the entire content of which is incorporated by reference herein.

FIELD OF THE INVENTION

The present disclosure is related to immunoglobulin proteins that specifically bind to natriuretic peptide receptor 1 (NPR1) agonists, and therapeutic methods of using those proteins.

SEQUENCE STATEMENT

The instant application contains a Sequence Listing, which has been submitted electronically in ASCII format and is hereby incorporated by reference in its entirety. Said ASCII copy, created on Dec. 13, 2021, is named 40848-0104USU1-SeqListing.txt and is 71 kilobytes in size.

BACKGROUND

Natriuretic peptide receptor 1 (NPR1; also known as NPR-A) belongs to the cell-surface family of the guanylyl cyclase receptors, enzymes that catalyze the conversion of GTP into cyclic GMP. NPR1 is highly expressed in kidney, lungs, adrenal, vasculature, brain, liver, endothelial and adipose tissues and at lower levels in the heart. It is activated by binding to atrial natriuretic peptide (ANP) or brain natriuretic peptide (BNP). NPR1 activation and signaling stimulate many physiologic responses involving many tissues. The ANP-NPR1 system has been well studied for its role in vasorelaxation, natriuresis, diuresis, endothelial permeability and in non-cardiovascular functions like lipolysis and immune cell functions (Potter 2011, *Pharmacol. Ther.* 130: 71-82). Activation of NPR1 leads to natriuresis (excretion of salt by kidneys) and lowers blood pressure.

Currently approved therapeutics intended for agonism of NPR1 present with multiple clinical challenges.

Monoclonal antibodies to NPR1 were first described by Kitano, et al., (1995 *Immunol Lett* 47: 215-22). Activating or agonist anti-NPR1 antibodies are disclosed in, for example, US Patent/Publication Nos. 9090695, and 20160168251, and in WO2010065293. Fully human agonist antibodies that specifically bind to NPR1 protein with high affinity and activate it have been described in US Publication No. 20200123263. R5381, is an agonist of NPR1 that has shown long duration of effect in reduction of systemic blood pressure as compared to current standard-of-care therapies.

In vivo studies have shown that R5381 induced significant and persistent reductions of systemic blood pressure, with no evidence of adverse hypotension (i.e., syncope, altered locomotion, death). Because the primary mode of action of certain anti-NPR1 antibodies has been found to be hemodynamic, there is a need for a reversal agent to preempt their hemodynamic effects.

SUMMARY

In an effort to address possible concerns regarding the use of NPR1 agonists (e.g., an activating or agonist anti-NPR1 antibody), reversal agents that bind specifically to such NPR1 agonists were developed, as disclosed herein.

Anti-NPR1 antibodies have been described for the treatment and/or prevention of a disease, disorder, or condition associated with NPR1 and/or for ameliorating at least one symptom associated with such disease, disorder, or condition (see, for example, WO2020/086406). The primary mode of action of the anti-NPR1 antibody is hemodynamic. Potential adverse events associated with the lowered blood pressure may include persistent, symptomatic hypotension, reflex tachycardia from compensatory sympathetic nervous system responses (possibly increasing the risk for myocardial infarction, stroke, arrhythmias, heart failure), and decreased cardiac output and end-organ perfusion in subjects with normal (low) venous pressures. Thus, there is a need for a reversal agent (or a rescue agent) that can target and stabilize or reduce or reverse the hemodynamic effects of the anti-NPR1 antibody.

Accordingly, the present disclosure provides an agent that reverses the hemodynamic effects of a natriuretic peptide receptor 1 (NPR1) agonist. The agent is also referred to as a reversal or rescue agent herein.

In another aspect, the present disclosure provides an agent that reverses a reduction in blood pressure associated with the administration of a NPR1 agonist in a subject.

In one embodiment, the agent is selected from the group consisting of an immunoglobulin protein, a vasopressor, an alpha-adrenoreceptor agonist, a steroid, an antidiuretic hormone, an angiogenesis inhibitor, and a small molecule agent that increases blood pressure.

In one embodiment, the agent is an immunoglobulin protein. In one embodiment, the agent specifically binds to the NPR1 agonist. In one embodiment, the NPR1 agonist is an antibody or antigen-binding fragment thereof that binds specifically to NPR1. In one embodiment, the anti-NPR1 antibody or antigen-binding fragment thereof comprises three heavy chain complementarity determining regions (CDRs) (HCDR1, HCDR2, and HCDR3) contained within a heavy chain variable region (HCVR) comprising SEQ ID NO:48; and three light chain CDRs (LCDR1, LCDR2 and LCDR3) contained within a light chain variable region (LCVR) comprising SEQ ID NO:52. In one embodiment, the anti-NPR1 antibody comprises three heavy chain complementarity determining regions (CDRs) (HCDR1, HCDR2, and HCDR3) comprising SEQ ID NOs:49, 50, and 51, respectively; and three light chain CDRs (LCDR1, LCDR2 and LCDR3) comprising SEQ ID NO:53, 54, and 55, respectively. In one embodiment, the anti-NPR1 antibody or antigen-binding fragment thereof comprises a HCVR of SEQ ID NO: 48 and a LCVR of SEQ ID NO: 52. In one embodiment, the anti-NPR1 antibody is a monoclonal antibody. In one embodiment, the anti-NPR1 antibody is an IgG1 or IgG4 antibody. In one embodiment, the anti-NPR1 antibody or antigen-binding fragment thereof comprises a heavy chain comprising SEQ ID NO:56 and a light chain comprising SEQ ID NO:57. In one embodiment, the anti-NPR1 antibody is R5381.

In one embodiment, the rescue agent is an immunoglobulin protein. In one embodiment, the immunoglobulin protein comprises a monoclonal antibody or antigen-binding fragment thereof. In another embodiment, the immunoglobulin protein comprises a bivalent antibody. In another embodiment, the immunoglobulin protein comprises a monovalent or 'one-armed' antibody. In another embodiment, the immunoglobulin protein comprises a recombinant monoclonal antibody. In another embodiment, the immunoglobulin protein comprises a fully human monoclonal antibody that is bivalent or monovalent. In another embodiment, the immunoglobulin protein is a fully human monoclonal antibody that is of IgG1 or IgG4 isotype. In one embodiment, the immunoglobulin protein comprises a Fab fragment. In some embodiments, the immunoglobulin protein comprises a monoclonal antibody or antigen-binding fragment thereof, a bivalent monoclonal antibody, a monovalent monoclonal antibody, a Fab fragment, F(ab)2 fragment, Fv fragment, Fd fragment, scFv, or dAb. In one embodiment, the immunoglobulin protein comprises at least one immunoglobulin variable domain comprising three heavy chain complementarity determining regions (CDRs) (HCDR1, HCDR2, and HCDR3) contained within a heavy chain variable region (HCVR) and three light chain CDRs (LCDR1, LCDR2 and LCDR3) contained within a light chain variable region (LCVR). In one embodiment, the immunoglobulin protein comprises one immunoglobulin variable domain comprising three heavy chain CDRs contained in a HCVR and three light chain CDRs contained in a LCVR. In one embodiment, the immunoglobulin protein further comprises a multimerizing component, wherein the multimerizing component comprises at least one Fc fragment. In one embodiment, the multimerizing component comprises a first Fc fragment and a second Fc fragment wherein the first Fc fragment or the second Fc fragment, but not both, comprises a modification in the CH3 domain that reduces binding of the immunoglobulin protein to Protein A as compared to an immunoglobulin protein lacking the modification. In one embodiment, the modification comprises a H315R substitution and a Y316F substitution (EU numbering).

In one embodiment, the immunoglobulin protein comprises a monovalent antibody, wherein the monovalent antibody comprises a heavy chain comprising a heavy chain constant region and a HCVR, and a light chain comprising a light chain constant region and a LCVR wherein the heavy chain is of human IgG1 or IgG4 isotype. In one embodiment, the heavy chain constant region comprises a modification in the CH3 domain that reduces binding of the immunoglobulin protein to Protein A as compared to an immunoglobulin protein lacking the modification. In one embodiment, the modification comprises a H315R substitution and a Y316F substitution (EU numbering). In one embodiment, the immunoglobulin protein further comprises a multimerizing component, wherein the multimerizing component comprises a Fc fragment. In one embodiment, the Fc fragment is of human IgG1 or IgG4 isotype.

In one embodiment, the immunoglobulin protein comprises a Fab fragment comprising one immunoglobulin variable domain comprising three heavy chain CDRs contained in a HCVR and three light chain CDRs contained in a LCVR. In one embodiment, the immunoglobulin protein further comprises a multimerizing component. In one embodiment, the multimerizing component comprises at least one Fc fragment. In one embodiment, the Fc fragment is of isotype IgG1, IgG4 or a variant thereof. In one embodiment, the multimerizing component comprises a first Fc fragment and a second Fc fragment wherein the first Fc fragment or the second Fc fragment, but not both, comprises a modification in the CH3 domain that reduces binding of the immunoglobulin protein to Protein A as compared to an immunoglobulin protein lacking the modification. In one embodiment, the modification comprises a H315R substitution and a Y316F substitution (EU numbering) in a Fc fragment of IgG1 or IgG4 isotype.

Table 1 sets forth the amino acid sequence identifiers of the heavy chain variable regions (HCVRs), light chain variable regions (LCVRs), heavy chain complementarity determining regions (HCDRs) (HCDR1, HCDR2 and HCDR3), and light chain complementarity determining regions (LCDRs) (LCDR1, LCDR2 and LCDR3) of exemplary immunoglobulin proteins. Table 2 sets forth the nucleic acid sequence identifiers of the HCVRs, LCVRs, HCDR1, HCDR2 HCDR3, LCDR1, LCDR2 and LCDR3 of the exemplary immunoglobulin proteins.

Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani, et al., *J. Mol. Biol.* 273:927-948 (1997); and Martin, et al., *Proc. Natl. Acad. Sci. USA* 86:9268-9272 (1989). Public databases are also available for identifying CDR sequences within an antibody.

In certain embodiments, the immunoglobulin proteins of the disclosure are antibodies, or antigen-binding fragments thereof, comprising a HCVR and a LCVR, said HCVR comprising an amino acid sequence listed in Table 1 having no more than twelve amino acid substitutions, and/or said LCVR comprising an amino acid sequence listed in Table 1 having no more than ten amino acid substitutions. For example, the present disclosure provides antibodies or antigen-binding fragments thereof comprising a HCVR and a LCVR, said HCVR comprising an amino acid sequence listed in Table 1, said amino acid sequence having one, two, three, four, five, six, seven, eight, nine, ten, eleven or twelve amino acid substitutions. In another example, the present disclosure provides antibodies or antigen-binding fragments thereof comprising a HCVR and a LCVR, said LCVR comprising an amino acid sequence listed in Table 1, said amino acid sequence having one, two, three, four, five, six, seven, eight, nine or ten amino acid substitutions. In one embodiment, the present disclosure provides immunoglobulin proteins or antigen-binding fragments thereof comprising a HCVR and a LCVR, said HCVR comprising an amino acid sequence listed in Table 1, said amino acid sequence having at least one amino acid substitution, and/or said LCVR comprising an amino acid sequence listed in Table 1, said amino acid sequence having at least one amino acid substitution.

In certain embodiments, the immunoglobulin proteins of the disclosure are antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

In certain embodiments, the immunoglobulin proteins of the disclosure are antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present disclosure also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present disclosure also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

In certain embodiments, the immunoglobulin proteins of the disclosure are antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present disclosure provides antibodies, or antigen-binding fragments thereof, comprising an HCDR3/LCDR3 amino acid sequence pair contained within any of the exemplary immunoglobulin proteins listed in Table 1. In certain embodiments, the HCDR3/LCDR3 amino acid sequence pair is selected from the group consisting of SEQ ID NOs: 8/16 and 28/36.

In certain embodiments, the immunoglobulin proteins of the disclosure are antibodies, or antigen-binding fragments thereof, encoded by nucleic acid molecules disclosed herein. For example, the present disclosure provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present disclosure also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present disclosure also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

In certain embodiments, the immunoglobulin proteins of the disclosure are antibodies, or antigen-binding fragments thereof having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield, et al., (2002) JBC 277:26733). In other applications, modification of galactosylation can be made in order to modify complement dependent cytotoxicity (CDC).

In one aspect, the present disclosure provides an immunoglobulin protein comprising: (i) one immunoglobulin variable domain comprising three heavy chain CDRs (HCDR1, HCDR2, and HCDR3) contained within a HCVR, and three light chain CDRs (LCDR1, LCDR2, and LCDR3) contained within a LCVR. In one embodiment, the HCVR of the immunoglobulin protein comprises an amino acid sequence selected from any of the HCVR sequences in Table 1. In one embodiment, the LCVR of the immunoglobulin protein comprises an amino acid sequence selected from any of the LCVR sequences in Table 1. In one embodiment, the HCVR comprises an amino acid sequence selected from the group consisting of SEQ ID NOs: 2 and 22; and the LCVR comprises an amino acid sequence selected from the group consisting of SEQ ID NOs: 10 and 30. In one embodiment, the antibody or antigen-binding fragment thereof comprises three heavy chain complementarity determining regions (CDRs) (HCDR1, HCDR2, and HCDR3) and three light chain CDRs (LCDR1, LCDR2 and LCDR3), wherein HCDR1 comprises an amino acid sequence selected from the group consisting of SEQ ID NOs: 4 and 24; HCDR2 comprises an amino acid sequence selected from the group consisting of SEQ ID NOs: 6 and 26; HCDR3 comprises an amino acid sequence selected from the group consisting of SEQ ID NOs: 8 and 28; LCDR1 comprises an amino acid sequence selected from the group consisting of SEQ ID NOs: 12 and 32; LCDR2 comprises an amino acid sequence selected from the group consisting of SEQ ID NOs: 14 and 34; and LCDR3 comprises an amino acid sequence selected from the group consisting of SEQ ID NOs: 16 and 36. In one embodiment, HCDR1-HCDR2-HCDR3-LCDR1-LCDR2-LCDR3 comprise amino acid sequences selected from (i) SEQ ID NOs: 4, 6, 8, 12, 14 and 16; or (ii) SEQ ID NOs: 24, 26, 28, 32, 34, and 36. In one embodiment, the immunoglobulin protein further comprises a multimerizing component, wherein the multimerizing component comprises at least one Fc fragment. In one embodiment, the Fc fragment is of IgG1 or IgG4 isotype. In one embodiment, the multimerizing component comprises a first Fc fragment and a second Fc fragment, wherein the first Fc fragment or the second Fc fragment, but not both, comprises a modification in the CH3 domain that reduces binding of the immunoglobulin protein to Protein A as compared to an immunoglobulin protein lacking the modification. In one embodiment, the modification comprises a H315R substitution and a Y316F substitution (EU numbering) in a Fc fragment of IgG1 or IgG4 isotype. In one embodiment, the multimerizing component comprises a Fc fragment comprising the amino acid sequence of SEQ ID NO: 46 and a Fc fragment comprising the amino acid sequence of SEQ ID NO: 58.

```
SEQ ID NO: 58:
ESKYGPPCPPCPAPEFLGGPSVFLFPPKPKDTLMISRTPEVTCVVVDV

SQEDPEVQFNVVYVDGVEVHNAKTKPREEQFNSTYRVVSVLTVLHQDW

LNGKEYKCKVSNKGLPSSIEKTISKAKGQPREPQVYTLPPSQEEMTKN

QVSLTCLVKGFYPSDIAVEWESNGQPENNYKTTPPVLDSDGSFFLYSR

LTVDKSRWQEGNVFSCSVMHEALHNRFTQKSLSLSPGK
```

In one embodiment, the immunoglobulin protein comprises a bivalent antibody or antigen-binding fragment thereof. In one embodiment, the immunoglobulin protein comprises a monovalent ('one-armed') antibody or antigen-binding fragment thereof. In one embodiment, the immunoglobulin protein comprises a heavy chain comprising the HCVR and a light chain comprising the LCVR, wherein the heavy chain is of human IgG1 or IgG4 isotype. In one embodiment, the heavy chain comprises a modification in the CH3 domain that reduces binding of the immunoglobulin protein to Protein A as compared to an immunoglobulin protein lacking the modification. In one embodiment, the modification comprises a H315R substitution and a Y316F substitution (EU numbering) in a heavy chain of IgG1 or IgG4 isotype. In one embodiment, the heavy chain has an amino acid sequence selected from the group consisting of SEQ ID NOs: 18 and 38; and the light chain has an amino acid sequence selected from the group consisting of SEQ ID NOs: 20 and 40. In one embodiment, the immunoglobulin protein further comprises a Fc fragment. In one embodiment, the Fc fragment is of IgG1 or IgG4 isotype. In one embodiment, the Fc fragment comprises an amino acid sequence comprising SEQ ID NO: 46.

In one embodiment, the immunoglobulin protein binds specifically to an anti-NPR1 antibody. In one embodiment, the anti-NPR1 antibody is R5381.

In one embodiment, the immunoglobulin protein is REGN9035. In one embodiment, the immunoglobulin protein is REGN9037.

In one aspect, the disclosure provides an isolated polynucleotide molecule comprising a polynucleotide sequence that encodes a heavy chain variable region (HCVR) of an immunoglobulin protein disclosed herein. In another aspect, the disclosure provides an isolated polynucleotide molecule comprising a polynucleotide sequence that encodes a light chain variable region (LCVR) of an immunoglobulin protein disclosed herein. In one aspect, the disclosure provides a vector comprising a polynucleotide molecule disclosed herein. In certain embodiments, the vector is a recombinant expression vector capable of expressing a polypeptide comprising a heavy and/or light chain variable region of an immunoglobulin protein. For example, the present disclosure includes recombinant expression vectors comprising any of the nucleic acid molecules disclosed herein, i.e., nucleic acid molecules encoding any of the HCVR, LCVR, and/or CDR sequences as set forth in Table 2. In another aspect, the disclosure provides a host cell expressing a vector disclosed herein. For example, the present disclosure provides a host cell comprising a first recombinant expression vector capable of expressing a polypeptide comprising a heavy chain variable region of an immunoglobulin protein; and a second expression vector capable of expressing a polypeptide comprising a light chain variable region of an immunoglobulin protein, as disclosed herein. In one embodiment, the present disclosure provides a host cell comprising a first isolated polynucleotide molecule comprising a polynucleotide sequence that encodes a heavy chain variable region (HCVR) of an immunoglobulin protein disclosed herein and a second isolated polynucleotide molecule comprising a polynucleotide sequence that encodes a light chain variable region (LCVR) of an immunoglobulin protein disclosed herein. In certain embodiments, the host cell comprises a mammalian cell or a prokaryotic cell. In certain embodiments, the host cell is a Chinese Hamster Ovary (CHO) cell or an *Escherichia coli* (*E. coli*) cell.

In one aspect, the disclosure provides a method of producing an immunoglobulin protein or fragment thereof that specifically binds to an anti-NPR1 antibody or antigen-binding fragment thereof, comprising growing a host cell disclosed herein under conditions permitting production of the antibody or fragment, and recovering the immunoglobulin protein or fragment so produced. In certain embodiments, the present disclosure provides methods of producing an immunoglobulin protein or fragment thereof of the disclosure, comprising introducing into a host cell an expression vector comprising a nucleic acid sequence encoding a HCVR and/or LCVR of an immunoglobulin protein or fragment thereof of the disclosure operably linked to a promoter; culturing the host cell under conditions favorable for expression of the nucleic acid sequence; and isolating the immunoglobulin protein or fragment thereof from the culture medium and/or host cell. The isolated immunoglobulin protein or fragment thereof may be purified using any of the methods known in prior art. In one embodiment, the immunoglobulin proteins of the present disclosure may be purified using reagents and methods employing differential binding to Protein A, as disclosed elsewhere herein.

In one embodiment, the rescue agent is a vasopressor. In another embodiment, the vasopressor is Midodrine.

In one aspect, the disclosure provides a pharmaceutical composition comprising a rescue agent disclosed herein and a pharmaceutically acceptable carrier or diluent. In one embodiment, the composition comprises a combination of a rescue agent and a second therapeutic agent. In one embodiment, the second therapeutic agent is any agent that is advantageously combined with the rescue agent. Additional combination therapies and co-formulations involving the rescue agents of the present disclosure are disclosed elsewhere herein.

In one aspect, the disclosure provides a method of reversing the hemodynamic effects of an agonist antibody or antigen-binding fragment that binds specifically to natriuretic peptide receptor 1 (NPR1) protein, the method comprising administering a pharmaceutical composition comprising a therapeutically effective amount of a rescue agent disclosed herein to a subject in need thereof.

In another aspect, the disclosure provides a method of reversing a reduction in blood pressure associated with the administration of an agonist antibody or antigen-binding fragment that binds specifically to natriuretic peptide receptor 1 (NPR1) protein, the method comprising administering a pharmaceutical composition comprising a therapeutically effective amount of a rescue agent disclosed herein to a subject in need thereof.

In certain embodiments, the pharmaceutical composition is administered subcutaneously, intravenously, intradermally, intraperitoneally, intramuscularly, or orally to the subject.

In another aspect, the disclosure provides the use of a rescue agent disclosed herein in the manufacture of a medicament for reversing the hemodynamic effects associated with the administration of an anti-NPR1 antibody in a subject need thereof.

In one embodiment, the subject has a NPR1-associated disease or disorder. In one embodiment, the disease or disorder is hypertension, heart failure and/or chronic kidney disease.

In one aspect, the present disclosure provides a composition comprising: (i) an immunoglobulin protein as disclosed herein; and (ii) and an NPR1 agonist. In one embodiment, the NPR1 agonist is an anti-NPR1 antibody (e.g., R5381). In one embodiment, the composition is used in a method for effective regulation of blood pressure in a subject in need thereof. In one embodiment, the subject has a NPR1-associated disease or disorder. In one embodiment, the disease or disorder is hypertension, heart failure and/or chronic kidney failure.

In one aspect, the disclosure provides an antibody or antigen-binding fragment thereof that competes for binding with an immunoglobulin protein disclosed herein.

In another aspect, the disclosure provides an antibody or antigen-binding fragment thereof that binds to the same epitope as an immunoglobulin protein disclosed herein.

Other embodiments will become apparent from a review of the ensuing detailed description.

Animals were then given a single 50 mg/kg subcutaneous injection of an anti-R5381 bivalent mAb or isotype control mAb as described in Table 23. All values are mean pressures over 24 hours for days −3-21±SEM, n=4-5 per group. Statistics—two way ANOVA with Dunnett's; *p<0.05 PBS vs. isotype control mAb; **p<0.01 PBS vs. isotype control mAb; !p<0.05 REGN6580 vs. isotype control mAb; #p<0.05 REGN6581 vs. isotype control.

Figure 8:
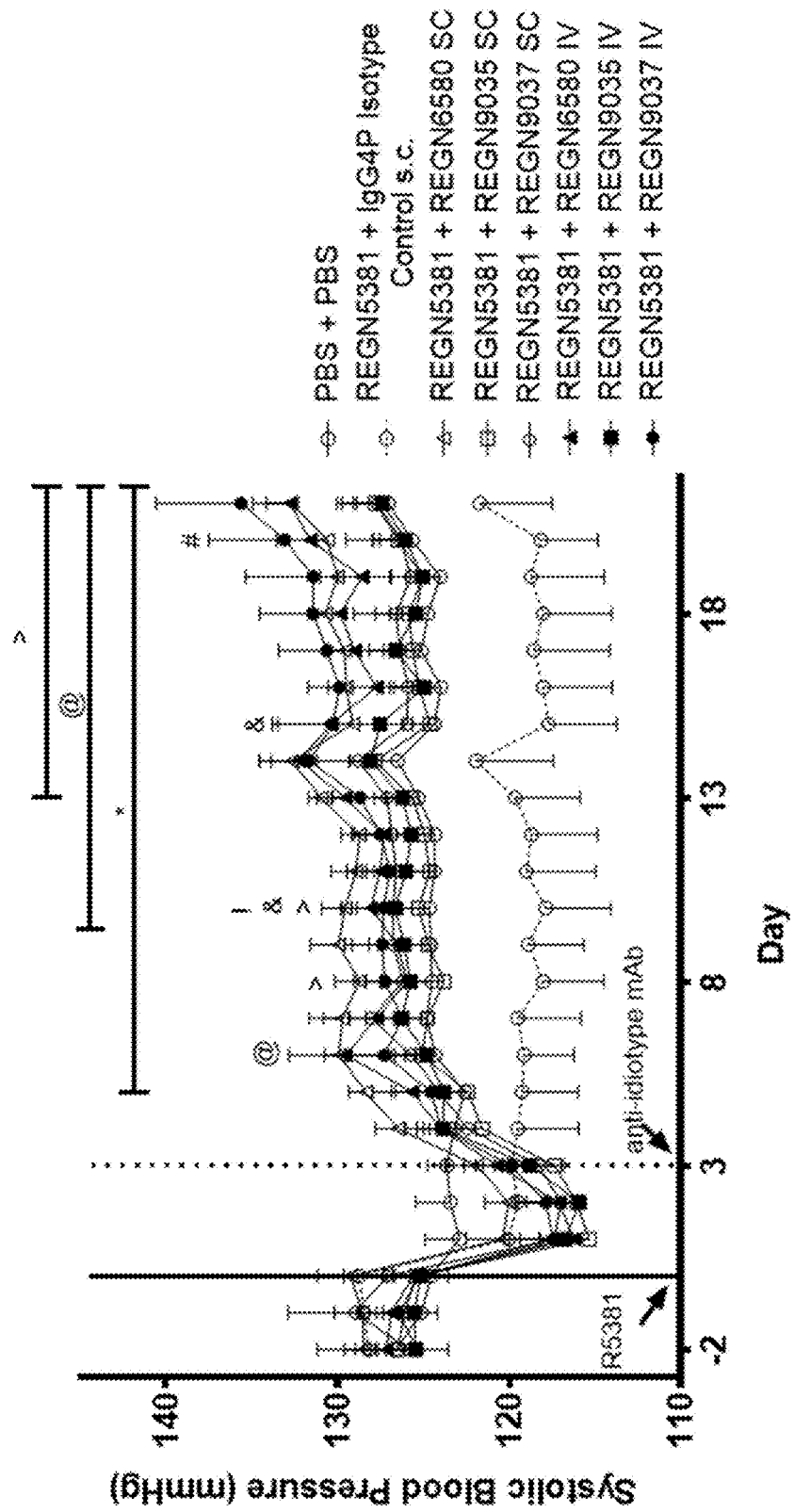

FIG. 8 shows, in line graph form, the effects of monovalent anti-R5381 mAbs on reversing R5381-induced systolic blood pressure-lowering in normotensive NPR1$^{hu/hu}$ mice. Telemetered normotensive NPR1$^{hu/hu}$ mice were randomized into groups based off of body weight. Animals were given a single 5 mg/kg subcutaneous injection of an NPR1 agonist mAb or isotype control mAb as described in Table 28. Animals were then given a single 50 mg/kg intravenous injection of an anti-R5381 bivalent (REGN6580) or monovalent (REGN9035 or REGN9037) mAb or PBS as described in Table 28. All values are mean±SEM, n=4-5 per group. Statistics—two way ANOVA with Dunnett's; *p<0.05 REGN6580 s.c. vs. isotype control mAb; #p<0.05 REGN9035 s.c. vs. isotype control mAb; !p<0.05 REGN9037 s.c. vs. isotype control mAb; @p<0.05 REGN6580 i.v. vs. isotype control mAb; &p<0.05 REGN9035 i.v. vs. isotype control mAb; ˜p<0.05 REGN9037 i.v. vs. isotype control mAb.

Figure 9:
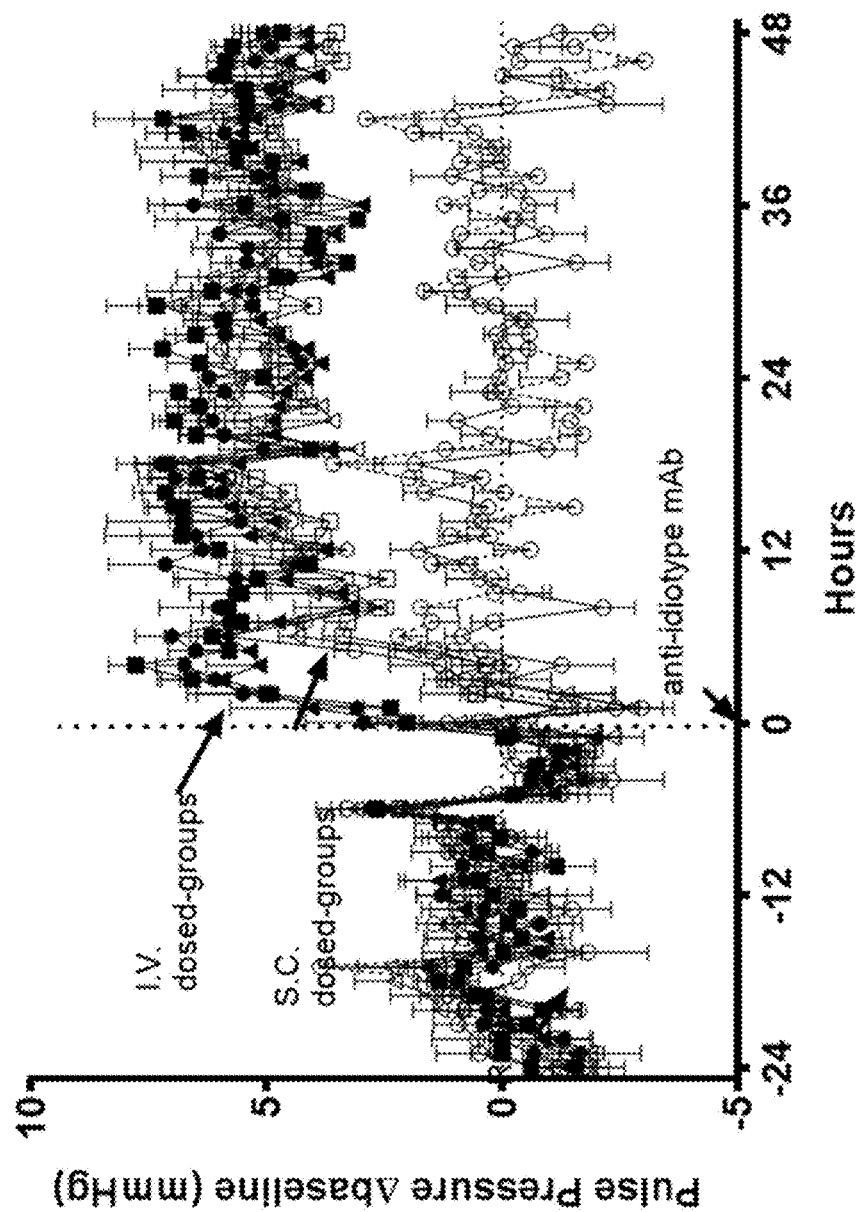

FIG. 9 shows, in line graph form, the acute effects of monovalent and bivalent anti-R5381 mAbs on reversing R5381-induced blood pressure-lowering in normotensive NPR1$^{hu/hu}$ mice. Telemetered normotensive NPR1$^{hu/hu}$ mice were randomized into groups based off of body weight. Animals were given a single 5 mg/kg subcutaneous injection of R5381 or PBS control as described in Table 28. Animals were then given a single 50 mg/kg intravenous injection of an anti-R5381 bivalent (REGN6580) or monovalent (REGN9035 or REGN9037) mAb or isotype control mAb as described in Table 28. All values are mean±SEM, n=4-5 per group.

Figure 10:
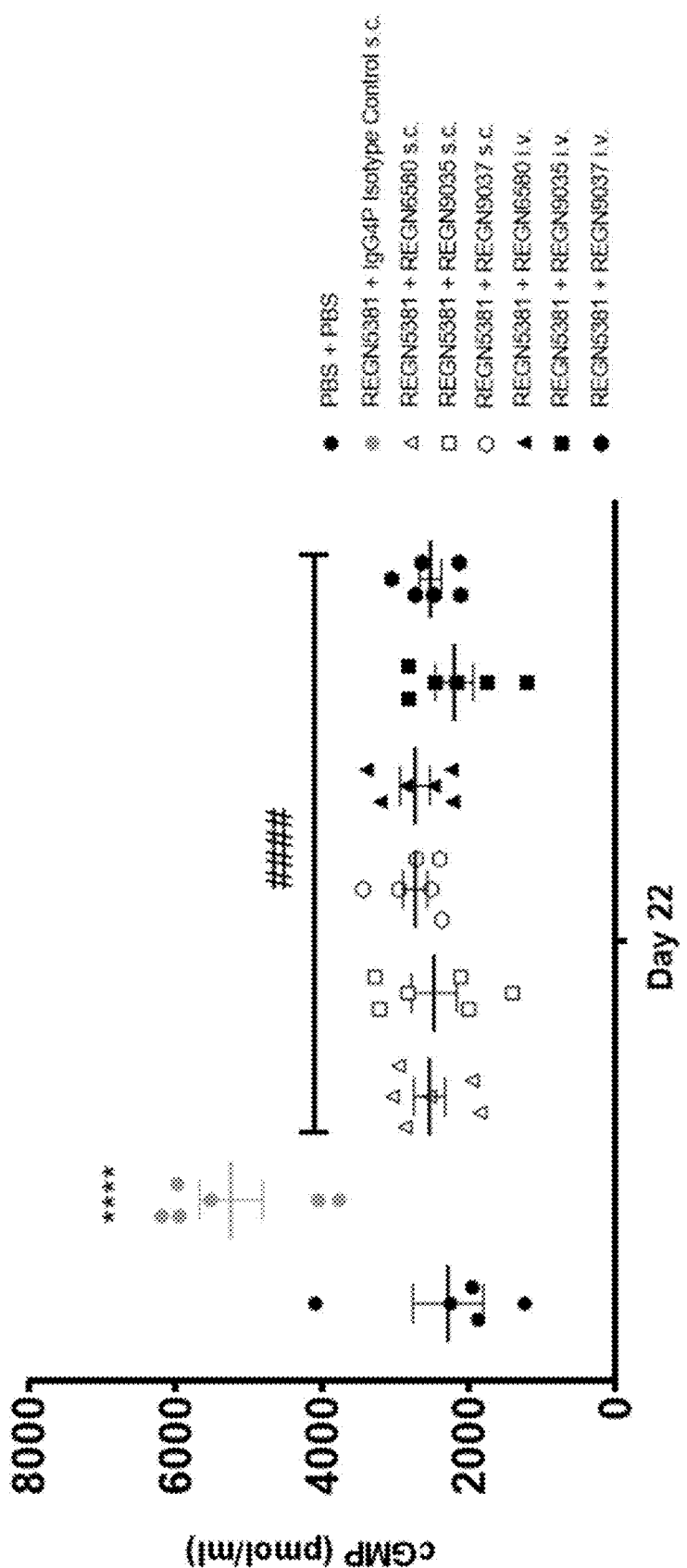

FIG. 10 shows, in line graph form, the effects of monovalent anti-R5381 mAbs on reversing R5381-induced cGMP generation in normotensive NPR1$^{hu/hu}$ mice. Telemetered normotensive NPR1$^{hu/hu}$ mice were randomized into groups based off of body weight. Animals were given a single 5 mg/kg subcutaneous injection of an NPR1 agonist mAb or isotype control mAb as described in Table 28. Animals were then given a single 50 mg/kg intravenous injection of an anti-R5381 bivalent (REGN6580) or monovalent (REGN9035 or REGN9037) mAb or PBS as described in Table 28. Urine was collected overnight from study day 21 to 22. All values are mean±SEM, n=5-6 per group. Statistics—ANOVA with Dunnett's; ****p<0.0001 vs. PBS+PBS; ####p<0.0001 vs. R5381+isotype control mAb.

Figure 11:
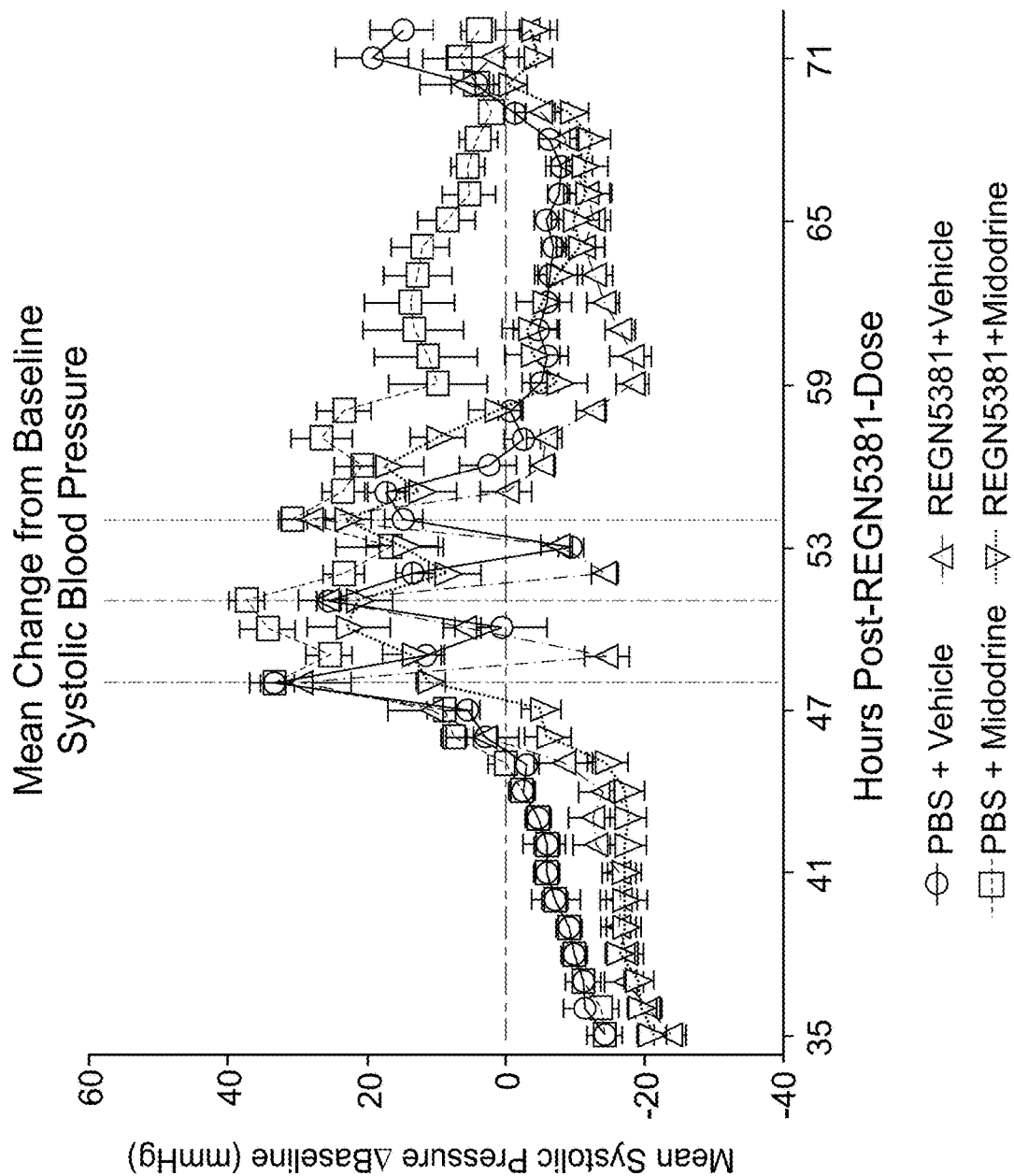

FIG. 11 shows that three doses of 2.5 mg/kg Midodrine administered three days after a single dose of 25 mg/kg R5381 reverse the blood pressure-lowering effects of R5381. Male cynomolgus monkeys weighing 3 to 5 kg were surgically implanted with a radio telemetry transmitter. On Day 0, animals each received a single IV bolus of saline (PBS; n=10) or 25 mg/kg R5381 (n=13). On Day 3, animals each received 3 doses of 2.5 mg/kg/dose midodrine (n=6 for saline group; n=7 for R5381 group) or water/vehicle (n=4 for saline group; n=6 for R5381 group) administered by oral gavage, with each dose spaced 3 to 4 hours apart, as indicated by dotted lines on the x-axis. Blood pressure measurements were collected for each animal pre-dose (for baseline measurements) and during a 4-day post-dose monitoring period. Mean changes from baseline systolic blood pressure for each treatment group between 35 and 72 hours post-R5381-dose are shown. Data are expressed as the group mean±standard error of the mean.

Figure 12:
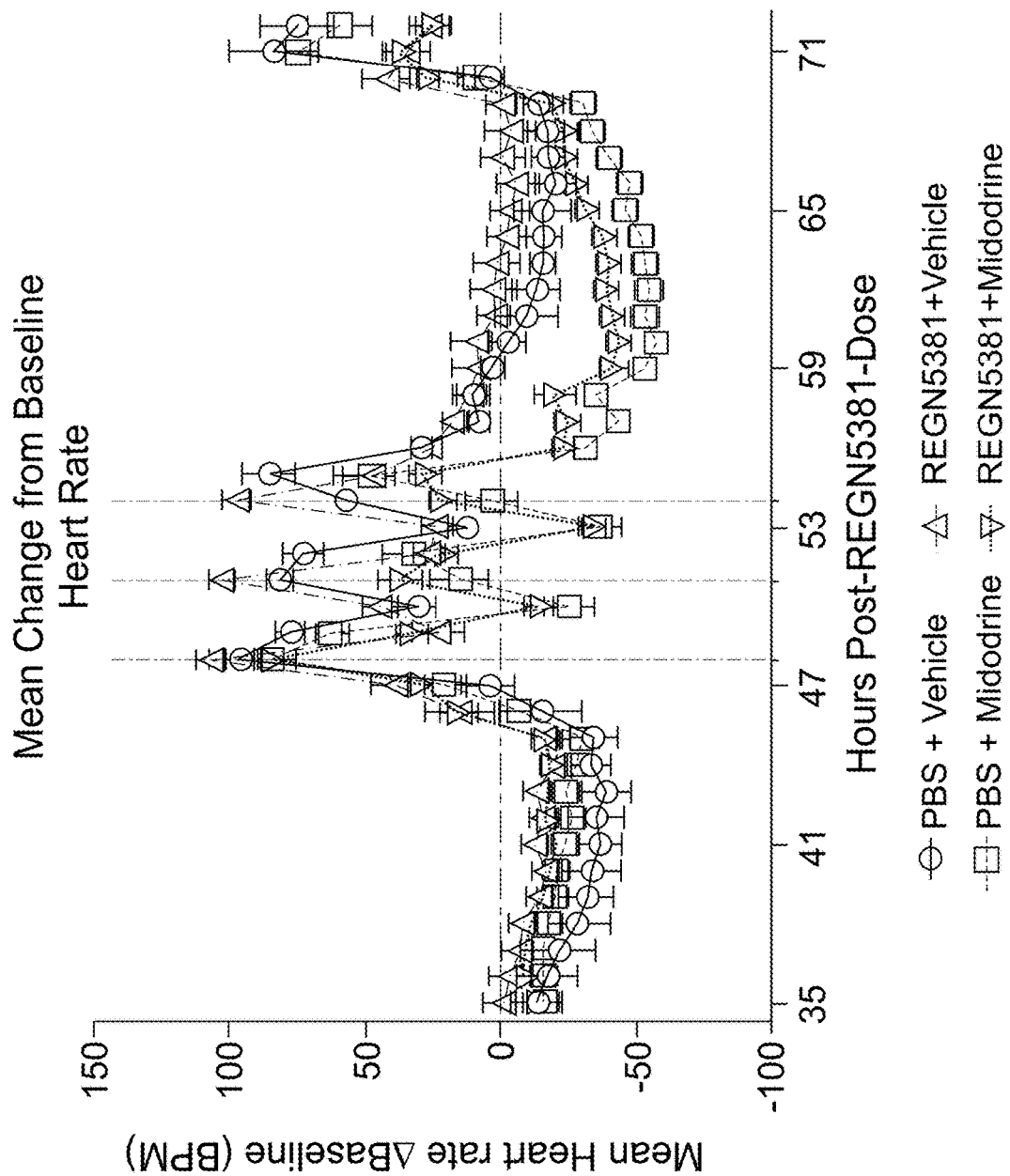

FIG. 12 shows that three doses of 2.5 mg/kg Midodrine administered 3 days after a single dose of 25 mg/kg reverse the R5381-induced heart rate effects. Male cynomolgus monkeys weighing 3 to 5 kg old were surgically implanted with a radio telemetry transmitter. On Day 0, animals each received a single IV bolus of saline (PBS; n=10) or 25 mg/kg R5381 (n=13). On Day 3, animals each received 3 doses of 2.5 mg/kg/dose midodrine (n=6 for saline group; n=7 for R5381 group) or water/vehicle (n=4 for saline group; n=6 for R5381 group) administered by oral gavage, with each dose spaced 3 to 4 hours apart, as indicated by dotted lines on the x-axis. Heart rate measurements were collected for each animal pre-dose (for baseline measurements) and during a 4-day post-dose monitoring period. Mean changes from baseline heart rate for each treatment group between 35 and 72 hours post-R5381-dose are shown. Data are expressed as the group mean±standard error of the mean.

DETAILED DESCRIPTION

Before the present methods are described, it is to be understood that this disclosure is not limited to particular methods, and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, preferred methods and materials are now described. All publications mentioned herein are incorporated herein by reference in their entirety.

Definitions

The term "NPR1", also called "NPRA," refers to natriuretic peptide receptor 1 (also known as natriuretic peptide receptor A). NPR1 is a homodimeric transmembrane guanylate cyclase, an enzyme that catalyzes cGMP synthesis. The protein has 4 distinct regions comprising an extracellular ligand-binding domain, a single transmembrane-spanning region, an intracellular protein kinase-like homology domain, and a guanylyl cyclase catalytic domain. The amino acid sequence of full-length NPR1 protein is exemplified by the amino acid sequence provided in UniProtKB/Swiss-Prot as accession number P16066.1 (SEQ ID NO:59):

```
  1 mpgprrpags rlrlllllll pplllllrgs hagnltvavv lplantsypw swarvgpave
 61 lalaqvkarp dllpgwtvrt vlgssenalg vcsdtaapla avdlkwehnp avflgpgcvy
```

```
-continued
121  aaapvgrfta  hwrvplltag  apalgfgvkd  eyalttragp  syaklgdfva  alhrrlgwer 181  qalmlyayrp  gdeehcfflv  eglfmrvrdr  lnitvdhlef  aeddlshytr  llrtmprkgr 241  viyicsspda  frtlmllale  aglcgedyvf  fhldifgqsl  qggqgpaprr  pwergdgqdv 301  sargafgaak  iitykdpdnp  eyleflkqlk  hlayeqfnft  medglvntip  asfhdgllly 361  iqavtetlah  ggtvtdgeni  tqrmwnrsfq  gvtgylkids  sgdretdfsl  wdmdpengaf 421  rvvlnyngts  qelvaysgrk  lnwplgyppp  dipkcgfdne  dpacnqdhls  tlevlalvgs 481  lsllgilivs  ffiyrkmqle  kelaselwrv  rwedvepssl  erhlrsagsr  ltlsgrgsny 541  gsllttegqf  qvfaktayyk  gnlvavkrvn  rkrieltrkv  lfelkhmrdv  qnehltrfvg 601  actdppnici  lteycprgsl  qdilenesit  ldwmfryslt  ndivkgmlfl  hngaicshgn 661  lkssncvvdg  rfvlkitdyg  lesfrdldpe  qghtvyakkl  wtapellrma  sppvrgsgag 721  dvysfgiilq  eialrsgvfh  vegldlspke  iiervtrgeq  ppfrpslalq  shleelgllm 781  grcwaedpqe  rppfgqirlt  lrkfnrenss  nildnllsrm  eqyannleel  veertqayle 841  ekrkaeally  gilphsvaeg  lkrgetvgae  afdsvtiyfs  divgftalsa  estpmqvvtl 901  lndlytcfda  vidnfdvykv  etigdaymvv  sglpvrngrl  hacevarmal  alldavrsfr 961  irhrpqeqlr  lrigihtgpv  cagvvglkmp  ryclfgdtvn  tasrmesnge  alkihlsset 1021 kavleefggf  elelrgdvem  kgkgkvrtyw  llgergsstr  g
```

The term "NPR1" includes recombinant NPR1 protein or a fragment thereof. The term also encompasses NPR1 protein or a fragment thereof coupled to, for example, histidine tag, mouse or human Fc, or a signal sequence.

The term "NPR1 agonist," as used herein, refers to a molecule that activates, increases or potentiates NPR1 activity or that stabilizes the activated conformation of NPR1. In preferred embodiments, the term "NPR1 agonist" refers to an antibody or antigen-binding fragment thereof that binds specifically to NPR1 and activates or increases at least one biological activity of NPR1. Such an agonist anti-NPR1 antibody may bind to NPR1 either in the presence or absence of a ligand (e.g., ANP or BNP). In certain embodiments, the biological activity includes, but is not limited to, decrease or reduction of blood pressure in a subject upon administration of the agonist anti-NPR1 antibody. In certain embodiments, the biological activity includes hemodynamic changes (e.g., reduction of blood pressure) in a subject having a disease or disorder such as hypertension, heart failure, or chronic kidney disease. The term includes agonist anti-NPR1 antibodies disclosed in, for example, US Publication No: 20200123263. In a specific embodiment, the term refers to an anti-NPR1 antibody comprising a HCVR of SEQ ID NO: 48 and a LCVR of SEQ ID NO: 52. In another specific embodiment, the term refers to R5381 (also known as REGN5381). R5381 is a fully human anti-NPR1 monoclonal antibody comprising a heavy chain that comprises the amino acid sequence of SEQ ID NO: 56 and a light chain that comprises the amino acid sequence of SEQ ID NO: 57.

As used herein, a "reversal agent" or "rescue agent" is an agent that reverses the hemodynamic effects of an NPR1 agonist. The terms "reversal agent" and "rescue agent" are used interchangeably herein. In certain embodiments, the reversal agent, as referred to herein, reverses hemodynamic changes associated with the administration (to a subject) of an agonist antibody or antigen-binding fragment that binds specifically to NPR1. The term "reverses" includes increasing the blood pressure of the subject, whose blood pressure has been reduced as a result of the administration of an NPR1 agonist. The increase in blood pressure can be measured using any standard blood pressure assessment means (e.g., sphygmomanometer) known in the art. The increase may be to its pre-agonist antibody treatment level, or to a level that results in adequate hemodynamic stability. Hemodynamic effects may include indirect effects, effects associated with a drop in blood pressure. These effects can likewise be reversed using the agents disclosed herein. Hemodynamic effects, as referred to herein, may include physiological parameters such as blood pressure and heart rate, or clinical signs such as dizziness, lightheadedness, blurred vision, nausea, fatigue. In certain embodiments, the reversal agent binds specifically to the NPR1 agonist and reverses hemodynamic effects caused by the NPR1 agonist. In specific embodiments, the reversal agent comprises an immunoglobulin protein as disclosed herein.

The term "immunoglobulin protein," as used herein refers to antigen-binding molecules that comprise at least one immunoglobulin variable domain. The at least one variable domain is the antigen-binding domain and comprises a heavy chain variable region and a light chain variable region. In certain embodiments, the variable domain is comprised in a Fab, Fv, single chain Fv, or any other antigen-binding fragment of an antibody, as disclosed elsewhere herein. In some embodiments, the variable domain is comprised in a monovalent or bivalent antibody. The term includes, but is not limited to, antibodies and antigen-binding fragments thereof, monovalent antibodies, bivalent antibodies and antigen-binding fragments thereof. The immunoglobulin protein may also comprise a multimerizing component linked to the variable domain. As disclosed elsewhere herein, the multimerizing component may comprise a Fc fragment of an antibody or a truncated heavy chain of an antibody. For example, an immunoglobulin protein of the present disclosure may comprise a single variable domain within a Fab wherein the Fab is linked to at least one Fc fragment. In certain embodiments, the immunoglobulin protein comprises: (i) a heavy chain comprising a heavy chain constant region and a heavy chain variable region, (ii) a light chain comprising a light chain constant region and a light chain variable region, and (iii) a polypeptide comprising a Fc fragment or a truncated heavy chain. In certain embodiments, the Fc domain polypeptide is a "dummy Fc," which refers to an Fc domain polypeptide that is not linked to an antigen binding domain. The immunoglobulin proteins comprising a single variable domain may be referred to as "one-armed" or "single arm" or "monovalent" antibodies. In the context of the disclosure, the term refers to an antibody or antigen-binding fragment thereof that binds to the variable region of another antibody ("anti-idiotype antibody"). In specific embodiments, the term refers to an antibody (or antigen-binding fragment thereof) that comprises a single variable domain that binds specifically to an anti-NPR1 antibody or antigen-binding fragment thereof. In one embodiment, the antibody or antigen-binding fragment thereof that specifically binds an anti-NPR1 antibody is a competitive binder. The one-armed antibodies of the present disclosure may comprise any of the HCVR/LCVR or CDR amino acid sequences as set forth in Table 1 herein. Exemplary one-armed anti-R5381 antibodies disclosed herein include REGN9035 and REGN9037.

The term "antibody", as used herein, unless specified otherwise, is intended to refer to immunoglobulin molecules comprised of four polypeptide chains, two heavy (H) chains and two light (L) chains inter-connected by disulfide bonds (i.e., "full antibody molecules"), as well as multimers thereof (e.g., IgM) or antigen-binding fragments thereof. In the context of the present disclosure, the term "bivalent antibodies" refers to "full antibody molecules," i.e., comprising 2 heavy chains and 2 light chain. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the disclosure, the FRs of the antibody (or antigen-binding fragment thereof) may be identical to the human germline sequences or may be naturally or artificially modified. An amino acid consensus sequence may be defined based on a side-by-side analysis of two or more CDRs.

In certain embodiments, the term "antibody" or "antigen-binding molecule" includes monovalent antigen binding molecules. A monovalent antigen binding molecule comprises a single antigen binding domain that is formed by a single heavy chain and a single light chain. The monovalent antigen binding molecule further includes a polypeptide comprising at least an Fc domain of a heavy chain. In certain embodiments, the Fc domain polypeptide is a "dummy Fc," which refers to an Fc domain polypeptide that is not linked to an antigen binding domain. In certain embodiments, the monovalent antibody has a complete heavy chain, a complete light chain, and a truncated heavy chain.

"Fc fragment" or "Fc region," as used herein, refers to the fragment crystallizable region of an immunoglobulin, which is the tail region of an antibody that interacts with cell surface receptors called Fc receptors and some proteins of the complement system. This property allows antibodies to activate the immune system. In IgG, IgA, and IgD antibody isotypes, the Fc region or Fc domain is derived from the second and third constant domains (CH2 and CH3) of the antibody's heavy chain; IgM and IgE Fc regions contain three heavy chain constant domains ($C_H$ domains 2-4) in the polypeptide chain. In the context of the present disclosure, the term refers to Fc region derived from human Fc domain, unless specified otherwise. In certain embodiments, the Fc fragment is derived from human IgG1, IgG2, IgG3, or IgG4 isotypes.

As used herein, a "multimerizing component" refers to any macromolecule that has the ability to associate with a second macromolecule of the same or similar structure or constitution. For example, a multimerizing component may be a polypeptide comprising an immunoglobulin $C_H3$ domain. A non-limiting example of a multimerizing component is an Fc portion of an antibody (comprising a $C_H2$-$C_H3$ domain), e.g., an Fc domain of an IgG selected from the isotypes IgG1, IgG2, IgG3, and IgG4, as well as any allotype within each isotype group. In certain embodiments, the immunoglobulin proteins of the present disclosure comprise a multimerizing component that comprises at least one Fc fragment. In certain embodiments, the immunoglobulin proteins comprise two Fc fragments. The first and second Fc fragments may be of the same IgG isotype such as, e.g., IgG1/IgG1, IgG2/IgG2, IgG4/IgG4. Alternatively, the first and second Fc fragments may be of different IgG isotypes such as, e.g., IgG1/IgG2, IgG1/IgG4, IgG2/IgG4, etc. In certain embodiments, the 2 Fc fragments have identical sequence. In certain embodiments, the 2 Fc fragments differ from each other by one or more amino acids. In certain embodiments, the first Fc fragment or the second Fc fragment, but not both Fc fragments, comprises a modification in the CH3 domain that reduces binding of the immunoglobulin protein to Protein A as compared to an immunoglobulin protein lacking the modification. In certain embodiments, the multimerizing component is an Fc fragment or an amino acid sequence of 1 to about 200 amino acids in length containing at least one cysteine residues. In other embodiments, the multimerizing component is a cysteine residue, or a short cysteine-containing peptide. Other multimerizing components include peptides or polypeptides comprising or consisting of a leucine zipper, a helix-loop motif, or a coiled-coil motif. The multimerizing component comprising, e.g., Fc domains, may comprise one or more amino acid changes (e.g., insertions, deletions or substitutions) as compared to the wild-type, naturally occurring version of the Fc domain, as disclosed elsewhere herein.

Substitution of one or more CDR residues or omission of one or more CDRs is also possible. Antibodies have been described in the scientific literature in which one or two CDRs can be dispensed with for binding. Padlan, et al., (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos, et al., 2002 *J Mol Biol* 320:415-428).

CDR residues not contacting antigen can be identified based on previous studies (for example, residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human immunoglobulin proteins (that specifically bind to anti-NPR1 antibodies) disclosed herein may comprise one or more amino acid substitutions, insertions, and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations").

A person of ordinary skill in the art, starting with the heavy and light chain variable region sequences disclosed herein, can easily produce numerous antibodies and antigen-binding fragments that comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic biological properties, reduced immunogenicity, etc. Antibodies and antigen-binding fragments obtained in this general manner are encompassed within the present disclosure.

The present disclosure also includes fully human immunoglobulin proteins (that specifically bind to anti-NPR1 antibodies) comprising variants of any of the HCVR, LCVR, and/or CDR amino acid sequences disclosed herein having one or more conservative substitutions. For example, the present disclosure includes fully human immunoglobulin proteins (that specifically bind to anti-NPR1 antibodies) having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to an anti-NPR1 antibody. An antibody fragment may include a Fab fragment, a $F(ab')_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "human antibody", or "fully human antibody", or "fully human immunoglobulin protein", as used herein, is intended to include antibodies having variable and constant regions derived from human germline immunoglobulin sequences. The human mAbs of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", or "fully human antibody", as used herein, is not intended to include mAbs in which CDR sequences derived from the germline of another mammalian species (e.g., mouse), have been grafted onto human FR sequences. The term includes antibodies that are recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the disclosure created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with, for example, an anti-NPR1 antibody that is relatively stable under physiologic conditions. Specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, that bind specifically to an anti-NPR1 antibody (e.g., R5381). Moreover, multi-specific antibodies that bind to one domain in an anti-NPR1 antibody and one or more additional antigens, or a bi-specific that binds to two different regions of an anti-NPR1 antibody, are nonetheless considered antibodies that "specifically bind", as used herein.

The term "high affinity" antibody refers to those mAbs having a binding affinity to an anti-NPR1 antibody, expressed as $K_D$, of at least $10^{-8}$ M; preferably $10^{-9}$ M; more preferably $10^{-10}$ M, even more preferably $10^{-11}$ M, as measured by surface plasmon resonance, e.g., BIACORE™ or solution-affinity ELISA.

By the term "slow off rate", "Koff" or "kd" is meant an antibody that dissociates from an anti-NPR1 antibody, with a rate constant of $1\times10^{-3}$ s$^{-1}$ or less, preferably $1\times10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The "antigen" of the immunoglobulin proteins described herein is an anti-NPR1 antibody (for example, R5381) or antigen-binding fragment thereof (i.e., fragment of the antibody that binds NPR1). The terms "antigen-binding fragment" of an antibody, or "antibody fragment", as used herein, refers to one or more fragments of an antibody that retain the ability to bind to an anti-NPR1 antibody.

In specific embodiments, antibody or antibody fragments of the disclosure may be conjugated to a moiety such as a ligand or a therapeutic moiety ("immunoconjugate"), a second rescue agent, or any other therapeutic moiety useful for reversing the hemodynamic effects of an anti-NPR1 antibody.

An "isolated antibody", as used herein, is intended to refer to an antibody that is substantially free of other antibodies (Abs) having different antigenic specificities (e.g., an isolated antibody that specifically binds an anti-NPR1 antibody, or a fragment thereof, is substantially free of Abs that specifically bind antigens other than anti-NPR1 antibodies).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction. In the context of the present disclosure, the "antigen" of the immunoglobulin proteins is an anti-NPR1 antibody (for example, R5381) or antigen-binding fragment thereof (i.e., fragment of the antibody that binds NPR1).

The term "epitope" refers to an antigenic determinant that interacts with a specific antigen binding site in the variable region of an antibody molecule known as a paratope. The "antigen" of the immunoglobulin proteins is an anti-NPR1 antibody (for example, R5381) or antigen-binding fragment thereof (i.e., fragment of the antibody that binds NPR1). A single antigen may have more than one epitope. Thus, different immunoglobulin proteins (antibodies) may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The "antigen" of the immunoglobulin proteins is an anti-NPR1 antibody (for example, R5381) or antigen-binding fragment thereof (i.e., fragment of the antibody that binds NPR1). The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies is the same antibody). Cross-competition between 2 antibodies may be expressed, for example, as % binding of the second antibody that is less than the baseline self-self background binding (wherein first and second antibodies is the same antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) *Methods Mol. Biol.* 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet, et al., (1992) *Science* 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul, et al., (1990) *J. Mol. Biol.* 215: 403-410 and (1997) *Nucleic Acids Res.* 25:3389-3402, each of which is herein incorporated by reference.

By the phrase "therapeutically effective amount" is meant an amount that produces the desired effect for which it is administered. The exact amount will depend on the purpose of the treatment and will be ascertainable by one skilled in the art using known techniques (see, for example, Lloyd (1999) The Art, Science and Technology of Pharmaceutical Compounding). For example, a therapeutically effective amount of a rescue agent according to the invention is, in one embodiment, the amount that results in some degree of reversal of the hemodynamic effects of a natriuretic peptide receptor 1 (NPR1) agonist.

As used herein, the term "subject" refers to an animal, preferably a mammal, more preferably a human. In specific embodiments of the disclosure, the subject has experienced, is experiencing, or may experience a drop in blood pressure or alteration in other hemodynamic parameters associated with the administration of an agonist antibody or antigen-binding fragment thereof that specifically binds NPR1.

As used herein, the terms "treat", "treating", or "treatment" refer to the reduction or amelioration of the severity of at least one symptom or indication of a disease or disorder due to the administration of a therapeutic agent such as an immunoglobulin protein described herein to a subject in need thereof. The terms include inhibition of progression of disease or of worsening of a symptom/indication. The terms also include positive prognosis of disease, i.e., the subject may be free of disease or may have reduced disease upon administration of a therapeutic agent such as an antibody of the present disclosure. The therapeutic agent may be administered at a therapeutic dose to the subject.

The terms "prevent", "preventing" or "prevention" refer to inhibition of manifestation of a disease or disorder or any symptoms or indications of such a disease or disorder upon administration of a therapeutic agent.

Preparation of Human Immunoglobulin Proteins

Immunoglobulin variable (antigen-binding) domains specific for particular antigens can be prepared by any antibody-generating technology known in the art. Once obtained, they can be appropriately arranged to produce an immunoglobulin protein molecule of the present disclosure using routine methods. (A discussion of exemplary immunoglobulin protein components and formats that can be used to construct the immunoglobulin protein molecules of the present disclosure is provided elsewhere herein.) In certain embodiments, one or more of the individual components (e.g., heavy and light variable regions) of the proteins of the disclosure are derived from chimeric, humanized, or fully human antibodies. Methods for making such antibodies are well known in the art. For example, human antibodies can be generated in transgenic mice.

Any such known methods can be used in the context of the present disclosure to make human antibodies that specifically bind to an anti-NPR1 antibody. In one embodiment, the anti-NPR1 antibody is R5381.

An immunogen comprising any one of the following can be used to generate antibodies to an anti-NPR1 antibody. In certain embodiments, the immunoglobulin proteins (antibodies) of the disclosure are obtained from mice immunized with a full length anti-NPR1 antibody (e.g., R5381) or with DNA encoding the protein or fragment thereof. Alternatively, the protein or a fragment thereof may be produced using standard biochemical techniques and modified and used as immunogen.

In some embodiments, the immunogen may be a recombinant anti-NPR1 antibody or antigen-binding fragment thereof expressed in *E. coli* or in any other eukaryotic or mammalian cells such as Chinese hamster ovary (CHO) cells.

One or more of the heavy and/or light chains of the immunoglobulin proteins of the present disclosure can be prepared using VELOCIMMUNE® technology (see, for example, U.S. Pat. No. 6,596,541, Regeneron Pharmaceuticals, VELOCIMMUNE®) or any other known method for generating monoclonal antibodies. Using VELOCIMMUNE® technology, high affinity chimeric antibodies to an anti-NPR1 antibody (e.g., R5381) are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

As in the experimental section below, the antibodies are characterized and selected for desirable characteristics, including affinity, selectivity, epitope, etc. The mouse constant regions are replaced with a desired human constant region to generate the fully human antibody of the disclosure, for example wild-type or modified IgG1 or IgG4. While the constant region selected may vary according to specific use, high affinity antigen binding and target specificity characteristics reside in the variable region.

Bioequivalents

The immunoglobulin proteins of the present disclosure encompass proteins having amino acid sequences that vary from those of the described antibodies, but that retain the ability to bind an anti-NPR1 antibody, for example, R5381. Such variant proteins comprise one or more additions, deletions, or substitutions of amino acids when compared to parent sequence but exhibit biological activity that is essentially equivalent to that of the described proteins (e.g., antibodies). Likewise, the immunoglobulin proteins' (e.g., antibody-encoding) DNA sequences encompass sequences that comprise one or more additions, deletions, or substitutions of nucleotides when compared to the disclosed sequence, but that encode an antibody or antibody fragment that is essentially bioequivalent to an immunoglobulin protein (e.g., antibody or antibody fragment) of the disclosure.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives, if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two immunoglobulin proteins are bioequivalent, if there are no clinically meaningful differences in their safety, purity, or potency.

In one embodiment, two immunoglobulin proteins are bioequivalent, if a patient can be switched one or more times between the reference product and the biological product without an expected increase in the risk of adverse effects, including a clinically significant change in immunogenicity, or diminished effectiveness, as compared to continued therapy without such switching.

In one embodiment, two immunoglobulin proteins are bioequivalent, if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the immunoglobulin protein or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the immunoglobulin protein (e.g., antibody (or its target)) is measured as a function of time; and (d) in a well-controlled clinical trial that establishes safety, efficacy, or bioavailability or bioequivalence of an immunoglobulin protein.

Bioequivalent variants of the immunoglobulin proteins (e.g., antibodies) of the disclosure may be constructed by, for example, making various substitutions of residues or sequences or deleting terminal or internal residues or sequences not needed for biological activity. The "biological activity" of the immunoglobulin proteins of the disclosure (for example, antibody or antibody fragment that specifically binds R5381) includes, but is not limited to, specifically binding the antigen (e.g., the anti-NPR1 antibody R5381), reversing the hemodynamic effects of the anti-NPR1 antibody, and increasing the blood pressure, which has dropped as a result of the administration of an anti-NPR1 antibody. Blood flow, cardiac loading, and/or heart rate are also positively affected in certain embodiments. For example, cysteine residues not essential for biological activity can be deleted or replaced with other amino acids to prevent formation of unnecessary or incorrect intramolecular disulfide bridges upon renaturation. In other contexts, bioequivalent immunoglobulin proteins may include antibody variants comprising amino acid changes, which modify the glycosylation characteristics of the antibodies, e.g., mutations that eliminate or remove glycosylation.

Immunoglobulin Proteins Comprising Fc Variants

According to certain embodiments of the present disclosure, immunoglobulin proteins are provided comprising an Fc domain comprising one or more mutations that enhance or diminish antibody binding to the FcRn receptor, e.g., at acidic pH as compared to neutral pH. For example, the present disclosure includes immunoglobulin proteins that bind anti-NPR1 antibodies and that comprise a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the immunoglobulin protein when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present disclosure includes immunoglobulin proteins that comprise an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations and other mutations within the antibody variable domains disclosed herein, are contemplated within the scope of the present disclosure.

The present disclosure also includes immunoglobulin proteins comprising a first $C_H3$ domain and a second Ig $C_H3$ domain, wherein the first and second Ig $C_H3$ domains differ from one another by at least one amino acid, and wherein at least one amino acid difference reduces binding of the immunoglobulin protein to Protein A as compared to a protein lacking the amino acid difference. In one embodiment, the first Ig $C_H3$ domain binds Protein A, and the second Ig $C_H3$ domain contains a mutation that reduces or abolishes Protein A binding such as an H315R by EU numbering. The second $C_H3$ may further comprise a Y316F by EU numbering. In one embodiment, the first Ig $C_H3$ domain binds Protein A, and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). See, for example, U.S. Pat. No. 8,586,713. Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies The present disclosure also includes immunoglobulin proteins that bind anti-NPR1 antibodies and that comprise a chimeric heavy chain constant ($C_H$) region, wherein the chimeric $C_H$ region comprises segments derived from the $C_H$ regions of more than one immunoglobulin isotype. For example, the immunoglobulin proteins of the disclosure may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the disclosure comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Patent Application Publication 2014/0243504, the disclosure of which is hereby incorporated by reference in its entirety).

Biological Characteristics of the Immunoglobulin Proteins

In general, the immunoglobulin proteins of the present disclosure function by binding to a NPR1 agonist (such as an anti-NPR1 antibody) and reversing its hemodynamic effects. For example, the present disclosure includes antibodies and antigen-binding fragments of antibodies that bind (the parental hybridoma of) an anti-NPR1 antibody with a $K_D$ of less than about 3 nM at 25° C. and less than about 7 nm at 37° C., as measured by surface plasmon resonance, e.g., using the assay format as defined in Example 3 herein. In certain embodiments, the antibodies or antigen-binding fragments thereof bind the parental hybridoma of an anti-NPR1 antibody with a $K_D$ of less than about 25 nM, less than about 10 nM, less than about 7 nM, less than about 6 nM, less than about 5 nM, less than about 4 nM, less than about 3 nM, less than about 2 nM, less than about 1 nM, less than about 0.75 nM, or less than about 0.5 nM, as measured by surface plasmon resonance, e.g., using the assay format as defined in Example 3 herein, or a substantially similar assay.

The present disclosure also includes immunoglobulin proteins and fragments thereof that bind to a NPR1 agonist in a pH-sensitive manner. For example, the $k_d$ and dissociative half-life (t½) of REGN9035 and REGN9037 vary in pH 7.4, pH 6.5, pH 6.0, and pH 5.0 buffers, as shown in Example 5 herein. For REGN9035, the dissociative half-life (t½) decreases significantly with decreasing pH, from about 12 minutes to about 0.6 minutes; for REGN9037, the dissociative half-life (t½) varies slightly with decreasing pH, between about 13 and about 17 minutes. The $k_d$ for each likewise varies, for REGN9035, between about 9.96E-04 and 1.97E-02, and for REGN9037, between about 8.67E-04 and about 6.64E-04.

The present disclosure also includes immunoglobulin proteins and fragments thereof that inhibit activation of hNPR1 that has been induced by an anti-NPR1 antibody. For example, bivalent and monovalent anti-R5381 antibodies and antigen-binding fragments thereof block R5381-induced activation of hNPR1 in the presence and absence of endogenous ligands (e.g., ANP, BNP). Maximum inhibition (about 97% to about 106%) of R5381-induced activation of NPR1 was measured by cGMP accumulation, e.g., using the assay format as defined in Example 6 herein, or a substantially similar assay. In certain embodiments, the antibodies or antigen-binding fragments of the disclosure inhibit at least about 50%, at least about 60%, at least about 70%, at least about 80%, at least about 90%, at least about 95%, at least about 96%, at least about 97%, at least about 98%, at least about 99%, at least about 100%, at least about 101%, at least about 102%, at least about 103%, at least about 104%, or at least about 105%, at least about 106% anti-NPR1 antibody-induced activation of hNPR1.

The present disclosure also includes immunoglobulin proteins and fragments thereof that block anti-NPR1 antibody binding to hNPR1. For example, bivalent and monovalent anti-R5381 antibodies and antigen-binding fragments thereof block biotin-R5381 from binding to human NPR1, as assessed using blocking ELISA, as described in Example 7, or a substantially similar assay. About 99% and about 100% blocking were assessed for the monovalent/one-armed and bivalent anti-R5381 antibodies, respectively. In certain embodiments, the antibodies or antigen-binding fragments of the disclosure block about 75%, about 80%, about 85%, about 90%, about 95%, about 96%, about 97%, about 98%, about 99%, or about 100% anti-NPR1 antibody binding to hNPR1.

The present disclosure also includes immunoglobulin proteins and fragments thereof that form minimal to none circulating immune complexes (CIC) with an agonist anti-NPR1 antibody. For example, bivalent and monovalent anti-R5381 antibodies and antigen-binding fragments thereof do not form detectable CICs with R5381, as assessed using Clq-CIC assay, as described in Example 8, or a substantially similar assay. In certain embodiments, the antibodies or antigen-binding fragments of the disclosure do not form CICs with anti-NPR1 antibodies. The presence of CICs in the circulation statistically correlates with disease activity.

The present disclosure also includes immunoglobulin proteins and fragments thereof that reverse the hemodynamic effects of an anti-NPR1 antibody. For example, bivalent anti-R5381 antibodies and antigen-binding fragments thereof were able to clear R5381 from mice faster and more effectively than isotype control, as assessed via immunoassay, as described in Example 10, or a substantially similar assay. Serum concentrations of R5381 were significantly lower at day 7 and undetectable at day 22. As another example, bivalent and monovalent anti-R5381 antibodies and antigen-binding fragments thereof rapidly and persistently reversed the blood pressure-lowering effects of R5381, as assessed collecting systolic pressure, diastolic pressure, pulse pressure, and mean arterial pressure, as well as heart rate, as described in Examples 11 and 12, or a substantially similar assay. The bivalent and monovalent anti-R5381 antibodies and antigen-binding fragments thereof also inhibited NPR1-induced cGMP production, as assessed in urine using ELISA, as described in Examples 11 and 12, or a substantially similar assay. In certain embodiments, the antibodies or antigen-binding fragments of the disclosure increase blood pressure back to baseline levels (i.e., back to levels before drop in blood pressure due to administration of an anti-NPR1 antibody).

In one embodiment, the present disclosure provides an isolated recombinant immunoglobulin protein or antigen-binding fragment thereof that binds specifically to an anti-NPR1 antibody (such as R5381), wherein the immunoglobulin protein exhibits one or more of the following characteristics: (a) comprises a fully human monoclonal antibody; (b) comprises a fully human monovalent or one-armed antibody; (c) comprises a single immunoglobulin domain and a multimerizing component comprising at least one Fc fragment; (d) binds to an anti-NPR1 antibody at 25° C. and at 37° C. with a dissociation constant ($K_D$) of less than 7 nM, as measured in a surface plasmon resonance assay; (e) shows pH-dependent dissociation; (f) inhibits about 97% to about 106% of an anti-NPR1 antibody-induced activation of NPR1; (g) blocks at least about biotin-anti-NPR1-agonist antibody from binding to human NPR1; (h) does not form detectable CICs with an anti-NPR1 antibody; (i) clears an anti-NPR1 antibody from serum faster than isotype control; (j) reverses the blood pressure-lowering effects of an anti-NPR1 antibody; and (k) comprises a HCVR comprising an amino acid sequence selected from the group consisting of HCVR sequences listed in Table 1 and a LCVR comprising an amino acid sequence selected from the group consisting of LCVR sequences listed in Table 1.

The immunoglobulin proteins of the present disclosure may possess one or more of the afore-mentioned biological characteristics, or any combinations thereof. Other biological characteristics of the immunoglobulin proteins of the present disclosure will be evident to a person of ordinary skill in the art from a review of the present disclosure including the working Examples herein.

Epitope Mapping and Related Technologies

The present disclosure includes immunoglobulin proteins that interact with one or more amino acids found within one or more regions of the anti-NPR1 antibody molecule. The epitope to which the immunoglobulin proteins bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the anti-NPR1 antibody molecule (e.g. a linear epitope in a domain). Alternatively, the epitope may consist of a plurality of non-contiguous amino acids (or amino acid sequences) located within either or both of the afore-mentioned domains of the antibody molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, NY). Other methods include alanine scanning mutational analysis, peptide blot analysis (Reineke, (2004) *Methods Mol. Biol.* 248: 443-63), peptide cleavage analysis crystallographic studies and NMR analysis. In addition, methods such as epitope excision, epitope extraction and chemical modification of antigens can be employed (Tomer, (2000) *Prot. Sci.* 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring, (1999) *Analytical Biochemistry* 267: 252-259; Engen and Smith, (2001) *Anal. Chem.* 73: 256A-265A.

The term "epitope" refers to a site on an antigen to which B and/or T cells respond. In the context of the present disclosure, the antigen is an anti-NPR1 antibody. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

In certain embodiments, the present disclosure includes immunoglobulin proteins and fragments thereof that interact with one or more epitopes found within the extracellular domain of an anti-NPR1 antibody. The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within the extracellular domain of an anti-NPR1 antibody. Alternatively, the epitope may consist of a plurality of non-contiguous amino acids (or amino acid sequences) located within an anti-NPR1 antibody.

The present disclosure includes antibodies that bind to the same epitope, or a portion of the epitope, as any of the specific exemplary immunoglobulin proteins listed in Table 1. Likewise, the present disclosure also includes antibodies that compete for binding to an anti-NPR1 antibody or a fragment thereof with any of the specific exemplary immunoglobulin proteins listed in Table 1. For example, the present disclosure includes antibodies that cross-compete for binding to an anti-NPR1 antibody or a fragment thereof with one or more antibodies listed in Table 1.

One can easily determine whether an antibody binds to the same epitope as, or competes for binding with, a reference immunoglobulin protein by using routine methods known in the art. For example, to determine if a test antibody binds to the same epitope as a reference immunoglobulin protein of the disclosure, the reference antibody is allowed to bind to an anti-NPR1 antibody protein or peptide under saturating conditions. Next, the ability of a test antibody to bind to the anti-NPR1 antibody protein molecule is assessed. If the test antibody is able to bind to an anti-NPR1 antibody following saturation binding with the reference immunoglobulin protein, it can be concluded that the test antibody binds to a different epitope than the reference immunoglobulin protein. On the other hand, if the test antibody is not able to bind to an anti-NPR1 antibody protein following saturation binding with the reference immunoglobulin protein, then the test antibody may bind to the same epitope as the epitope bound by the reference immunoglobulin protein of the disclosure.

To determine if an antibody competes for binding with a reference immunoglobulin protein, the above-described binding methodology is performed in two orientations: in a first orientation, the reference antibody is allowed to bind to an anti-NPR1 antibody protein under saturating conditions followed by assessment of binding of the test antibody to the anti-NPR1 antibody molecule. In a second orientation, the test antibody is allowed to bind to an anti-NPR1 antibody molecule under saturating conditions followed by assessment of binding of the reference antibody to the anti-NPR1 antibody molecule. If, in both orientations, only the first (saturating) antibody is capable of binding to the anti-NPR1 antibody molecule, then it is concluded that the test antibody and the reference antibody compete for binding to the anti-NPR1 antibody. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope, if each competitively inhibits (blocks) binding of the other to the antigen. The antigen is an anti-NPR1 antibody. That is, a 1-, 5-, 10-, 20-, or 100-fold excess of one antibody inhibits binding of the other by at least 50%, but preferably 75%, 90%, or even 99% as measured in a competitive binding assay (see, e.g., Junghans, et al., *Cancer Res.* 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The disclosure further encompasses a human immunoglobulin protein conjugated to a therapeutic moiety ("immunoconjugate"), to treat a NPR1-associated disease or disorder (e.g., hypertension) and/or to ameliorate the hemodynamic effects associated with the therapeutic use of an anti-NPR1 antibody. As used herein, the term "immunoconjugate" refers to an immunoglobulin protein that is chemically or biologically linked to a radioactive agent, a cytokine, an interferon, a target or reporter moiety, an enzyme, a peptide or protein, or a therapeutic agent. The said protein may be linked to the radioactive agent, cytokine, interferon, target or reporter moiety, enzyme, peptide, or therapeutic agent at any location along the molecule, so long as it is able to bind its target, an anti-NPR1 antibody. Examples of immunoconjugates include antibody-drug conjugates and antibody-toxin fusion proteins. In one embodiment, the agent may be a second different antibody to NPR1 protein. The type of therapeutic moiety that may be conjugated to the rescue agent will take into account the condition to be treated and the desired therapeutic effect to be achieved. Examples of suitable agents for forming immunoconjugates are known in the art; see for example, WO 05/103081.

Therapeutic Administration and Formulations

The disclosure provides therapeutic compositions comprising immunoglobulin proteins of the present disclosure. Therapeutic compositions in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semisolid gels, and semi-solid mixtures containing carbowax. See also Powell, et al., "Compendium of excipients for parenteral formulations", PDA (1998) *J Pharm Sci Technol* 52:238-311.

The dose of immunoglobulin protein may vary depending upon the age and the size of a subject to be administered, conditions, route of administration, and the like. When a protein of the present disclosure is used for reversing the hemodynamic effects of an anti-NPR1 antibody in an adult patient, or for preventing such hemodynamic effects, it is advantageous to administer the immunoglobulin protein of the present disclosure normally at a single dose of about 0.1 to about 100 mg/kg body weight. Depending on the severity of the condition, the frequency and the duration of the treatment can be adjusted. In certain embodiments, the immunoglobulin proteins of the disclosure can be administered as an initial dose of at least about 0.1 mg to about 800 mg, about 1 to about 600 mg, about 5 to about 500 mg, or about 10 to about 400 mg. In certain embodiments, the initial dose may be followed by administration of a second or a plurality of subsequent doses of the immunoglobulin protein or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu, et al., (1987) *J. Biol. Chem.* 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) *Science* 249: 1527-1533).

The use of nanoparticles to deliver the immunoglobulin proteins of the present disclosure is also contemplated herein. Antibody-conjugated nanoparticles may be used both for therapeutic and diagnostic applications. Antibody-conjugated nanoparticles and methods of preparation and use are described in detail by Arruebo, M., et al., 2009 ("Antibody-conjugated nanoparticles for biomedical applications" in *J. Nanomat*. Volume 2009, Article ID 439389, 24 pages, doi: 10.1155/2009/439389), incorporated herein by reference. Nanoparticles may be developed and conjugated to antibodies contained in pharmaceutical compositions to target cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracranial, intraperitoneal and intramuscular injections, drip infusions, etc. These injectable preparations may be prepared by methods publicly known.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the immunoglobulin protein contained is generally about 5 to about 500 mg per dosage form in a unit dose; especially in the form of injection, it is preferred that the immunoglobulin protein is contained in about 5 to about 300 mg and in about 10 to about 300 mg for the other dosage forms.

Therapeutic Uses of the Immunoglobulin Proteins

The present disclosure includes methods comprising administering to a subject in need thereof a therapeutic composition comprising an immunoglobulin protein. The therapeutic composition can comprise any of the immunoglobulin proteins as disclosed herein and a pharmaceutically acceptable carrier or diluent. As used herein, the expression "a subject in need thereof" means a human or non-human animal that would benefit from an increase in blood pressure or a reversal of an effect due to an administration of a NPR1 agonist.

The immunoglobulin proteins of the disclosure (and therapeutic compositions comprising the same) are useful, inter alia, for treating any disease or disorder in which an increase in blood pressure would be beneficial. In particular, the immunoglobulin proteins of the present disclosure may be used for the treatment, prevention, and/or amelioration of any disease or disorder associated with or mediated by NPR1 expression or activity. The mechanism of action by which the therapeutic methods of the disclosure are achieved include binding to an agonist anti-NPR1 antibody and removal/clearance of the agonist antibody. Removal of the agonist anti-NPR1 antibody results in an increase in blood pressure.

The immunoglobulin proteins of the present disclosure may be used to treat, e.g., any NPR1-associated disease or disorder in a subject that has been administered an NPR1 agonist, and wherein a reversal of the hemodynamic effects of the NPR1 agonist is desired. Examples of NPR1-associated disease or disorder include, but are not limited to, hypertension, heart failure, obesity, renal failure, chronic kidney disease, macular edema, glaucoma, stroke, lung disorders, pulmonary fibrosis, inflammation, asthma, skeletal growth disorders, bone fractures, diabetes, and cancer. Administration of a therapeutic composition comprising an immunoglobulin protein of the present disclosure may lead to prevention of one or more adverse effects related to lowered blood pressure. Potential adverse events associated with the lowered blood pressure may include persistent, symptomatic hypotension, reflex tachycardia from compensatory sympathetic nervous system responses (possibly increasing the risk for myocardial infarction, stroke, arrhythmias, heart failure), and decreased cardiac output and end-organ perfusion in subjects with normal (low) venous pressures.

In one embodiment, the immunoglobulin proteins of the disclosure are used for the preparation of a pharmaceutical composition or medicament for treating patients having hypotension as a result of administration of an anti-NPR1 antibody. In another embodiment, the immunoglobulin proteins are used as adjunct therapy with any other agent, or any other therapy known to those skilled in the art useful for increasing blood pressure and/or addressing symptoms associated with a drop in blood pressure.

The present disclosure also provides a composition comprising: (i) a therapeutic amount of an immunoglobulin protein as disclosed herein; and (ii) an agonist anti-NPR1 antibody for use in a method for effective regulation of blood pressure and/or hemodynamic changes in a subject wherein the subject suffers from a NPR1-associated disease or disorder.

Non-Immunoglobulin Protein Reversal Agents

In certain embodiments of the disclosure, the agent for use in reversing the hemodynamic effects of an anti-NPR1 antibody or antigen-binding fragment thereof (i.e., the reversal agent) is selected from the group consisting of a vasopressor, an alpha-adrenoreceptor agonist, a steroid, an antidiuretic hormone, a vascular endothelial growth factor (VEGF) antagonist/an angiogenesis inhibitor, and a small molecule agent that increases blood pressure.

A vasopressor is an agent that constricts the blood vessels, increasing blood pressure. An alpha-adrenoreceptor agonist ($\alpha$-agonist) binds to $\alpha$-receptors on vascular smooth muscle and induces smooth contraction and vasoconstriction, increasing blood pressure. An antidiuretic hormone is a hormone released by the posterior pituitary, which acts on the kidneys to increase the re-absorption of water, causing vasoconstriction in the cardiovascular system. Vasopressors and antidiuretic hormones are known in the art.

In another embodiment, the reversal agent is a medication for the treatment of anti-NPR1 antibody-induced hemodynamic effects, selected from the group consisting of, but not limited to, midodrine, Levophed, norepinephrine, phenylephrine, fludrocortisone, Orvaten, Northera, ephedrine, Vazculep, droxidopa, Akovaz, Biorphen, Corphedra, and Emerphed.

Thus, the present disclosure includes reversal agents other than immunoglobulin proteins (including antibodies) that can reverse the hemodynamic effects of anti-NPR1 antibody therapy. For example, the al-adrenergic receptor agonist, Midodrine can reverse the blood pressure and heart rate effects of R5381, as described herein in Example 14.

Combination Therapies

In certain embodiments, it is contemplated to use the immunoglobulin proteins and other reversal agents of the present disclosure in combination with one or more other known hypotensive therapies to manage a subject's blood pressure. In specific embodiments, the immunoglobulin proteins of the disclosure are used in combination with NPR1 agonists, preferably with anti-NPR1 antibodies. In one specific embodiment, the immunoglobulin proteins of the present disclosure are used in combination with R5381 for effective management of blood pressure in a subject in need thereof.

Combination therapies may include an immunoglobulin protein of the disclosure and any additional therapeutic agent that may be advantageously combined with an immunoglobulin protein of the disclosure, or with a biologically active fragment of an immunoglobulin protein of the disclosure. The immunoglobulin proteins of the present disclosure may be combined synergistically with one or more drugs or therapy used to increase blood pressure or address effects associated with a drop in blood pressure.

As used herein, the term "in combination with" means that additional therapeutically active component(s) may be administered prior to, concurrent with, or after the administration of the immunoglobulin protein or other reversal agent of the present disclosure. The term "in combination with" also includes sequential or concomitant administration of an immunoglobulin protein or other reversal agent and a second therapeutic agent.

In specific embodiments, the immunoglobulin proteins of the disclosure are administered to a subject in combination with NPR1 agonists, e.g., R5381. In further embodiments, the immunoglobulin proteins of the disclosure and the NPR1 agonists, e.g., R5381, are administered to a subject concurrently (at the same time), either together in one composition or separately in more than one composition. In still further embodiments, the immunoglobulin proteins of the disclosure and the NPR1 agonists, e.g., R5381, are administered to a subject sequentially, the NPR1 agonists, e.g., R5381, followed by the immunoglobulin proteins of the disclosure.

The additional therapeutically active component(s) may be administered to a subject prior to administration of an immunoglobulin protein or other reversal agent of the present disclosure. For example, a first component may be deemed to be administered "prior to" a second component, if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, or less than 30 minutes before administration of the second component. In other embodiments, the additional therapeutically active component(s) may be administered to a subject after administration of an immunoglobulin protein or other reversal agent of the present disclosure. For example, a first component may be deemed to be administered "after" a second component, if the first component is administered 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after or more after administration of the second component. In yet other embodiments, the additional therapeutically active component(s) may be administered to a subject concurrent with administration of an immunoglobulin protein or other reversal agent of the present disclosure.

"Concurrent" administration, for purposes of the present disclosure, includes, e.g., administration of an immunoglobulin protein or other reversal agent and an additional therapeutically active component to a subject in a single dosage form, or in separate dosage forms administered to the subject within about 30 minutes or less of each other. If administered in separate dosage forms, each dosage form may be administered via the same route (e.g., both the immunoglobulin protein or other reversal agent and the additional therapeutically active component may be administered intravenously, etc.); alternatively, each dosage form may be administered via a different route (e.g., the immunoglobulin protein or other reversal agent may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an immunoglobulin protein or other reversal agent "prior to", "concurrent with," or "after" (as those terms are defined herein above) administration of an additional therapeutically active component is considered administration of an immunoglobulin protein or other reversal agent "in combination with" an additional therapeutically active component.

The present disclosure includes pharmaceutical compositions in which an immunoglobulin protein or other reversal agent of the present disclosure is co-formulated with one or more of the additional therapeutically active component(s) as described elsewhere herein.

Diagnostic Uses of the Immunoglobulin Proteins

The rescue agents of the present disclosure may be used to detect and/or measure anti-NPR1 antibody in a sample, e.g., for diagnostic purposes. Exemplary diagnostic assays for an anti-NPR1 antibody may comprise, e.g., contacting a sample obtained from a patient with a rescue agent of the disclosure, wherein the rescue agent is labeled with a detectable label or reporter molecule or used as a capture ligand to selectively isolate the anti-NPR1 antibody from patient samples. Alternatively, an unlabeled rescue agent can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure anti-NPR1 antibody in a sample include enzyme-linked immunosorbent assay (ELISA), radioimmunoassay (RIA), and fluorescence-activated cell sorting (FACS).

Samples that can be used in anti-NPR1 antibody diagnostic assays according to the present disclosure include any tissue or fluid sample obtainable from a patient, which contains detectable quantities of either anti-NPR1 antibody protein, or fragments thereof, after administration of the same to a subject. Generally, levels of anti-NPR1 antibody protein in a particular sample obtained from a healthy patient (e.g., a patient who has not received anti-NPR1 antibody) will be measured to initially establish a baseline, or standard, level of anti-NPR1 antibody. This baseline level of anti-NPR1 antibody can then be compared against the levels of anti-NPR1 antibody measured in samples obtained from individuals suspected of having been administered an anti-NPR1 antibody.

The immunoglobulin proteins specific for anti-NPR1 antibody protein may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions of the disclosure, and are not intended to limit the scope of what the inventors regard as their invention. Efforts have been made to ensure accuracy with respect to numbers used (e.g., amounts, temperature, etc.), but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1

Generation of Human Antibodies to Agonist Antibodies that Specifically Bind Natriuretic Peptide Receptor 1 (NPR1)

Generation of Anti-R5381 Antibodies

Human antibodies to anti-NPR1 antibody protein were generated in a VELOCIMMUNE® mouse comprising DNA encoding human Immunoglobulin heavy and kappa light chain variable regions. The mice were immunized with anti-NPR1 antibody R5381 (described elsewhere herein).

The antibody immune response was monitored by an anti-R5381-specific immunoassay. When a desired immune response was achieved, splenocytes were harvested and fused with mouse myeloma cells to preserve their viability and form hybridoma cell lines. The hybridoma cell lines were screened and selected to identify cell lines that produce anti-R5381-specific antibodies. The cell lines were used to obtain several anti-R5381 chimeric antibodies (i.e., antibodies possessing human variable domains and mouse constant domains).

Anti-R5381 antibodies were also isolated directly from antigen-positive mouse B cells without fusion to myeloma cells, as described in U.S. Pat. No. 7,582,298, herein specifically incorporated by reference in its entirety. Using this method, several fully human anti-R5381 antibodies (i.e., antibodies possessing human variable domains and human constant domains) were obtained.

Exemplary antibodies generated as disclosed above were designated as mAb36312 and mAb36313.

Generation of 'One-Armed' Anti-R5381 Antibodies

Selected antibodies as generated above were used to produce monovalent or 'one-armed' antibodies or antigen-binding molecules. Such monovalent antigen-binding molecules include a single R5381-binding portion comprising a HCVR and LCVR. Monovalent antibodies comprising a full-length heavy chain, a full-length light chain and an additional Fc domain polypeptide were constructed using standard methodologies (see WO2010151792), wherein the heavy chain constant region differs from the Fc domain polypeptide by at least two amino acids. Such modifications are useful in purification of the monovalent antibodies (see WO2010151792).

Exemplified one-armed antibodies were manufactured having an IgG4 Fc domain and were designated as REGN9035 and REGN9037.

The biological properties of the exemplary antibodies generated in accordance with the methods of this Example are described in detail in the Examples set forth below.

Example 2

Heavy and Light Chain Variable Region Amino Acid and Nucleotide Sequences

Table 1 sets forth the amino acid sequence identifiers of the heavy and light chain variable regions and CDRs of selected anti-R5381 antibodies of the disclosure.

TABLE 1

| Antibody | Amino Acid Sequence Identifiers | | | | | | | |
|---|---|---|---|---|---|---|---|---|
| | SEQ ID NOs: | | | | | | | |
| Designation | HCVR | HCDR1 | HCDR2 | HCDR3 | LCVR | LCDR1 | LCDR2 | LCDR3 |
| mAb36312 | 2 | 4 | 6 | 8 | 10 | 12 | 14 | 16 |
| mAb36313 | 22 | 24 | 26 | 28 | 30 | 32 | 34 | 36 |

The corresponding nucleic acid sequence identifiers are set forth in Table 2.

TABLE 2

| Antibody | Nucleic Acid Sequence Identifiers | | | | | | | |
|---|---|---|---|---|---|---|---|---|
| | SEQ ID NOs: | | | | | | | |
| Designation | HCVR | HCDR1 | HCDR2 | HCDR3 | LCVR | LCDR1 | LCDR2 | LCDR3 |
| mAb36312 | 1 | 3 | 5 | 7 | 9 | 11 | 13 | 15 |
| mAb36313 | 21 | 23 | 25 | 27 | 29 | 31 | 33 | 35 |

Antibodies referred to herein typically have fully human variable region(s) but may have human or mouse constant regions. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 2—will remain the same, and the binding properties to antigen are expected to be identical or substantially similar regardless of the nature of the Fc domain. In certain embodiments, selected antibodies with a mouse IgG1 Fc are converted to antibodies with human IgG4 Fc. In one embodiment, the IgG4 Fc domain comprises 2 or more amino acid changes as disclosed in US20100331527. In one embodiment, the human IgG4 Fc comprises a serine to proline mutation in the hinge region (S108P) to promote dimer stabilization. Unless indicated otherwise, all antibodies used in the following examples comprise a human IgG4 isotype.

An exemplary bivalent antibody comprising the HCVR/LCVR amino acid sequence pair of SEQ ID NOs: 2/10 is REGN6580. REGN6580 comprises a heavy chain comprising the amino acid sequence of SEQ ID NO: 18 and a light chain comprising the amino acid sequence of SEQ ID NO: 20.

An exemplary bivalent antibody comprising the HCVR/LCVR amino acid sequence pair of SEQ ID NOs: 22/30 is REGN6581. REGN6581 comprises a heavy chain comprising the amino acid sequence of SEQ ID NO: 38 and a light chain comprising the amino acid sequence of SEQ ID NO: 40.

Selected anti-R5381 antibodies were used in the construction of one-armed antibodies which comprise an anti-R5381 binding arm and an additional Fc polypeptide (or truncated heavy chain). In certain embodiments, the anti-R5381 binding arm comprises a heavy chain constant region of IgG1, IgG2, IgG3, IgG4 isotypes or a variant thereof. In one embodiment, the additional Fc polypeptide is of IgG1 isotype or a variant thereof. In one embodiment, the additional Fc polypeptide is of IgG4 isotype of a variant thereof.

Tables 3A, 3B, and 3C list the HCVR, LCVR, CDRs and heavy chain and light sequence identifiers of selected one-armed antibodies.

TABLE 3A

Amino acid sequences of variable regions and CDRs of selected antibodies

| Antibody Identifier | HCVR | HCDR1 | HCDR2 | HCDR3 | LCVR | LCDR1 | LCDR2 | LCDR3 |
|---|---|---|---|---|---|---|---|---|
| REGN9035 | 2 | 4 | 6 | 8 | 10 | 12 | 14 | 16 |
| REGN9037 | 22 | 24 | 26 | 28 | 30 | 32 | 34 | 36 |

TABLE 3B

Heavy chain and light chain amino acid sequence identifiers of selected antibodies

| Antibody Identifier | Anti-R5381 Heavy Chain | Truncated Heavy Chain | Light Chain |
|---|---|---|---|
| REGN9035 | SEQ ID NO: 42 | SEQ ID NO: 46 | SEQ ID NO: 20 |
| REGN9037 | SEQ ID NO: 44 | SEQ ID NO: 46 | SEQ ID NO: 40 |

TABLE 3C

Heavy chain and light chain nucleic acid sequence identifiers of selected antibodies

| Antibody Identifier | Anti-R5381 Heavy Chain | Truncated Heavy Chain | Light Chain |
|---|---|---|---|
| REGN9035 | SEQ ID NO: 41 | SEQ ID NO: 45 | SEQ ID NO: 19 |
| REGN9037 | SEQ ID NO: 43 | SEQ ID NO: 45 | SEQ ID NO: 39 |

Unless indicated otherwise, all antibodies used in the following examples comprise a human IgG4 isotype.

Example 3

Biacore Binding Kinetics of Selected Antibodies

Equilibrium dissociation constants ($K_D$) for binding of selected anti-R5381 antibodies (mAbs) to H2aM22033N (parental hybridoma of R5381) were determined using a real-time surface plasmon resonance (SPR) based Biacore T200 biosensor. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM5 sensor chip surface was first derivatized by amine coupling with anti-mouse Fc specific antibody (GE Healthcare, #BR100838) to capture H2aM22033N. Different concentrations of mAbs (100 nM-3.7 nM, 3-fold serial dilution) prepared in HBS-ET running buffer were injected at a flow rate of 50 µL/min for 3 minutes. The dissociation of different mAbs bound to H2aM22033N was monitored for 10 minutes in HBS-ET running buffer. At the end of each cycle, the H2aM22033N capture surface was regenerated using a 60 sec injection of 10 mM Glycine-HCl, pH 1.5. The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\min) = \frac{\ln(2)}{60 * kd}$$

Binding kinetics parameters for different mAbs binding to H2aM22033N of the disclosure at 25° C. and 37° C. are shown in Table 4 and Table 5, below, respectively.

TABLE 4

Binding kinetics parameters of different mAbs binding to H2aM22033N at 25° C.

| mAb Captured | Injected Analyte | Construct details of Injected Analyte | mAb Capture Level (RU) | 100 nM Ag Bound (RU) | $k_a$ (1/Ms) | $k_d$ (1/s) | $K_D$ (M) | $t_{1/2}$ (min) |
|---|---|---|---|---|---|---|---|---|
| H2aM22033N | REGN6580 | Bivalent hIgG4 | 179 ± 1.4 | 110 | 1.78E+05 | 9.42E−05 | 5.28E−10 | 123 |
| | REGN9035 | Monovalent hIgG4 | 148 ± 0.7 | 47 | 7.51E+04 | 1.32E−04 | 1.76E−09 | 87 |
| | REGN6712 | Fab | 174 ± 0.3 | 60 | 8.50E+04 | 2.47E−04 | 2.90E−09 | 47 |
| | REGN6581 | Bivalent hIgG4 | 177 ± 0.5 | 65 | 1.27E+05 | 7.11E−05 | 5.61E−10 | 163 |
| | REGN9037 | One-arm hIgG4 | 144 ± 0.5 | 31 | 6.51E+04 | 9.89E−05 | 1.52E−09 | 117 |
| | REGN6713 | Fab | 173 ± 0.5 | 39 | 5.91E+04 | 1.66E−04 | 2.81E−09 | 70 |

TABLE 5

Binding kinetics parameters of different mAbs binding to H2aM22033N at 37° C.

| mAb Captured | Injected Analyte | Construct details of Injected Analyte | mAb Capture Level (RU) | 100 nM Ag Bound (RU) | $k_a$ (1/Ms) | $k_d$ (1/s) | $K_D$ (M) | $t_{1/2}$ (min) |
|---|---|---|---|---|---|---|---|---|
| H2aM22033N | REGN6580 | Bivalent hIgG4 | 217 ± 0.7 | 160 | 4.64E+05 | 4.24E−04 | 9.14E−10 | 27 |
| | REGN9035 | Monovalent hIgG4 | 166 ± 1.6 | 81 | 1.49E+05 | 8.60E−04 | 5.78E−09 | 13 |
| | REGN6712 | Fab | 210 ± 0.4 | 85 | 2.18E+05 | 1.09E−03 | 5.02E−09 | 11 |
| | REGN6581 | Bivalent hIgG4 | 215 ± 0.6 | 104 | 3.17E+05 | 3.67E−04 | 1.16E−09 | 31 |
| | REGN9037 | One-arm hIgG4 | 158 ± 0.6 | 55 | 1.10E+05 | 7.38E−04 | 6.71E−09 | 16 |
| | REGN6713 | Fab | 209 ± 0.5 | 66 | 1.64E+05 | 8.09E−04 | 4.95E−09 | 14 |

Example 4

Cross-Competition Between Different Anti-R5381 Antibodies

Binding competition between anti-R5381 antibodies (mAbs) was determined using a real time, label-free biolayer interferometry (BLI) assay on the Octet HTX biosensor platform (Pall ForteBio Corp.). The entire experiment was performed at 25° C. in 10 mM HEPES, 150 mM NaCl, 3 mM EDTA, and 0.05% v/v Surfactant Tween-20, 1 mg/mL BSA, pH 7.4 (HBS-EBT) buffer with the plate shaking at a speed of 1000 rpm. To assess whether 2 mAbs are able to compete with one another for binding to their respective epitopes on R5381, ~0.47 nm of R5381 was first captured onto anti-human antibody (AHC) coated Octet biosensor tips (Fortebio Inc, #18-5064) by submerging the biosensor tips for 1 minute in wells containing 1.7 µg/mL solution of R5381. The R5381 captured biosensor tips were then saturated with the first anti-R5381 mAb (subsequently referred to as mAb-1) by dipping into wells containing 50 µg/mL solution of mAb-1 for 4 minutes. The biosensor tips were then subsequently dipped into wells containing 50 µg/mL solution of second anti-R5381 mAb (subsequently referred to as mAb-2) for 2 minutes. The biosensor tips were washed in HBS-ETB buffer in between every step of the experiment. The real-time binding response was monitored during the entire course of the experiment and the binding response at the end of every step was recorded. The response of mAb-2 binding to R5381 pre-complexed with mAb-1 was compared, and competitive/non-competitive behavior of different anti-R5381 mAbs was determined. There was cross-competition between the anti-R5381 mAbs.

Example 5 pH Sensitivity of Anti-R5381 Antibody Binding to R5381

The dissociation rate constants ($k_d$) for different anti-R5381 mAbs in pH 7.4, pH 6.5, pH 6.0, and pH 5.0 buffers were determined using a real-time surface plasmon resonance (SPR) based Biacore 4000 biosensor. All binding studies were performed at 37° C. using four running buffers, (i) PBS, 0.05% v/v Surfactant Tween-20, pH 7.4 (PBS-T-pH 7.4), (ii) PBS, 0.05% v/v Surfactant Tween-20, pH 6.5 (PBS-T-pH 6.5), (iii) PBS, 0.05% v/v Surfactant Tween-20, pH 6.0 (PBS-T-pH 6.0), and (iv) PBS, 0.05% v/v Surfactant Tween-20, pH 5.0 (PBS-T-pH 5.0). The Biacore CM5 sensor chip surface was first derivatized by amine coupling with anti-mouse Fc specific antibody (GE Healthcare, #BR100838) to capture H2aM22033N (parental hybridoma of R5381). Different concentrations of anti-R5381 mAbs (100 nM-11.11 nM, 3-fold serial dilution) prepared in PBS-T-pH7.4 buffer were injected at a flow rate of 30 µL/min for 3 minutes followed by the dissociation of bound anti-R5381 mAb in PBS-T-pH 7.4, PBS-T-pH 6.5, PBS-T-pH 6.0 or PBS-T PBS-T-pH 5.0 running buffers for 10 minutes.

The dissociation rate constants ($k_d$) in four pH running buffers were determined by fitting the real-time binding sensorgrams to a 1:1 binding model using Scrubber 2.0c curve-fitting software. The dissociative half-life (t½) was calculated from the $k_d$ values as:

$$t1/2(\text{min}) = \frac{\ln(2)}{60 * kd}$$

The $k_d$ and t½ values for selected anti-R5381 mAbs binding to H2aM22033N in PBS-T, pH 7.4 followed by dissociation in PBS-T-pH 7.4, PBS-T-pH 6.5, PBS-T-pH 6.0 or PBS-T-pH 5.0 of the disclosure at 37° C. are shown in Table 6, Table 7, Table 8, and Table 9, respectively.

TABLE 6

Binding of selected anti-R5381 mAbs to H2aM22033N in PBS-T-pH 7.4 buffer and the dissociation in PBS-T-pH 7.4 buffer at 37° C.

| mAb Captured | Injected Analyte | mAb Capture Level (RU) | 100 nM Ag Bound (RU) | $k_d$ (1/s) | $t_{1/2}$ (min) |
|---|---|---|---|---|---|
| H2aM22033N | REGN9035 | 159 ± 0.9 | 84 | 9.96E−04 | 12 |
|  | REGN9037 | 155 ± 1 | 55 | 8.67E−04 | 13 |

TABLE 7

Binding of selected anti-R5381 mAbs to H2aM22033N in PBS-T-pH 7.4 buffer and the dissociation in PBS-T-pH 6.5 buffer at 37° C.

| mAb Captured | Injected Analyte | mAb Capture Level (RU) | 100 nM Ag Bound (RU) | $k_d$ (1/s) | $t_{1/2}$ (min) |
|---|---|---|---|---|---|
| H2aM22033N | REGN9035 | 173 ± 0.4 | 97 | 1.42E−03 | 8 |
|  | REGN9037 | 172 ± 0.3 | 63 | 7.92E−04 | 15 |

TABLE 8

Binding of selected anti-R5381 mAbs to H2aM22033N in PBS-T-pH 7.4 buffer and the dissociation in PBS-T-pH 6.0 buffer at 37° C.

| mAb Captured | Injected Analyte | mAb Capture Level (RU) | 100 nM Ag Bound (RU) | $k_d$ (1/s) | $t_{1/2}$ (min) |
|---|---|---|---|---|---|
| H2aM22033N | REGN9035 | 171 ± 0.8 | 95 | 2.94E−03 | 3.9 |
|  | REGN9037 | 168 ± 0.4 | 61 | 8.11E−04 | 14 |

TABLE 9

Binding of selected anti-R5381 mAbs to H2aM22033N in PBS-T-pH 7.4 buffer and the dissociation in PBS-T-pH 5.0 buffer at 37° C.

| mAb Captured | Injected Analyte | mAb Capture Level (RU) | 100nM Ag Bound (RU) | $k_d$ (1/s) | t½ (min) |
|---|---|---|---|---|---|
| H2aM22033N | REGN9035 | 165 ± 0.5 | 84 | 1.97E−02 | 0.6 |
|  | REGN9037 | 162 ± 0.3 | 54 | 6.64E−04 | 17 |

Figure 1:
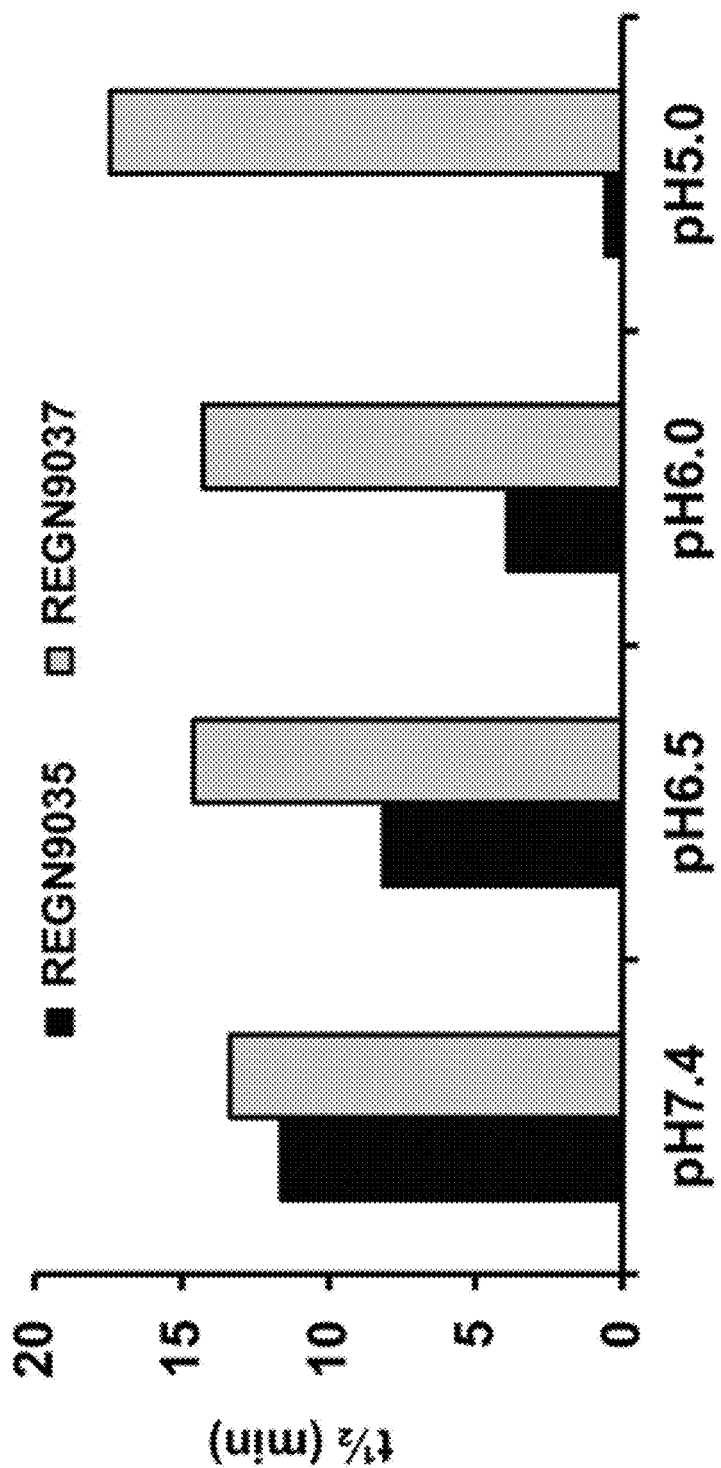
FIG. 1 provides, in bar graph form, a comparison of the dissociative half-life (t½) of anti-R5381 antibodies REGN9035 and REGN9037 in pH 7.4, pH 6.5, pH 6.0, and pH 5.0 buffers.

A comparison of the dissociative half-life (t½) of R5381 anti-idiotype monoclonal antibodies REGN9035 and REGN9037 in pH 7.4, pH 6.5, pH 6.0, and pH 5.0 buffers is shown in FIG. 1.

Example 6

Inhibition of R5381-Induced NPR1 Activation

In order to assess the regulation of human NPR1 (hNPR1), a stable HEK293 cell line stably expressing hNPR1 with a C-term myc and FLAG tag was developed. The cell line was sorted for high expression of hNPR1, HEK293/hNPR1.MycDDK HS or abbreviated as HEK29/hNPR1, and maintained in DMEM containing 10% FBS, NEAA, pen/strep/glut, and 500 µg/mL G418 sulfate. Binding of ligand to NPR1 activates the receptor's guanylate cyclase domain, which catalyzes the production of cGMP from GTP (Zois, et al., 2014 Nature 11(7):403-412). A homogeneous time-resolved fluorescence (HTRF) assay that measures cGMP levels was used to assess NPR1 activity.

For the cGMP assay, HEK293/hNPR1 cells were plated in 96-well half-area plates at 20,000 cells/well with 50 µl of complete growth media and cultured overnight. The next day, activation of hNPR1 was induced by replacing the media with 10 µl of dilution buffer (OptiMEM with 0.1% FBS) followed by the addition of 10 µl of 2× agonist at a range of concentrations including a sample without any agonist (see Table 10, below) made in dilution buffer. To evaluate the reversal of R5381-induced hNPR1 activation, cells were treated with 10 µl of 2× anti-R5381 at a range of concentrations (see Table 10) made in dilution buffer followed by the addition of 10 µl of 70 nM R5381 made in dilution buffer alone or containing 40 pM ANP or 80 pM BNP. The treated cells were incubated at 37° C. for 30 min. HTRF assay was performed using a cGMP HTRF kit from Cisbio according to manufacturer's protocol (#62GM2PEH). Briefly, 20 µl of 1×cGMP series dilution was added to empty wells for cGMP standard curve. For measuring cGMP concentration in samples with test articles, 10 µl of cGMP-d2 and 10 µl of anti-cGMP antibody conjugated with cryptate diluted in lysis buffer were added in order to each well for 60 min at RT in dark. The fluorescence intensity was detected using an EnVision multilabel plate reader (excitation=320 nm, emission=620 nm/665 nm, Perkin Elmer), and the fluorescence resonance energy transfer (FRET) ratio was calculated using the equation described below:

$$FRET \text{ ratio} = \frac{\text{Signal at 665 nm}}{\text{Signal at 620 nm}} \times 10\wedge 4$$

The FRET ratios were converted to cGMP concentrations according to the cGMP standard curve and analyzed using a 4-parameter logistic equation over an 11 point dose-response curve to obtain the half maximal effective concentration ($EC_{50}$) values for the tested agonists and the half maximal inhibitory concentration ($IC_{50}$) values for the tested antagonists using GraphPad Prism 8. The maximum inhibition was calculated with the equation described below:

% Maximum inhibition =

$$\frac{[cGMP, nM]_{70nM\ REGN5381} - [cGMP, nM]_{test\ antibody}}{[cGMP, nM]_{70nM\ REGN5381} - [cGMP, nM]_{baseline}} \times 100\%$$

In this equation, $[cGMP, nM]_{baseline}$, $[cGMP, nM]_{test\ antibody}$ and $[cGMP, nM]_{70nM\ R5381}$ are the cGMP concentration values from the cells treated with dilution buffer, the highest concentration of the anti-R5381 antibody, and 70 nM R5381 with or without 40 pM ANP or 80 pM BNP, respectively.

TABLE 10

Concentration of reagents used in NPR1 cGMP assay

| NPR1 agonist | Concentration Range [nM] |
|---|---|
| ANP | 2–0.0020 |
| BNP | 4–0.0039 |
| R5381 | 300–0.29 |
| Anti-R5381 (±R5381, ±ANP or ±BNP) | 300–0.29 |

TABLE 11

One-armed and bivalent anti-R5381 antibodies significantly inhibited R5381-induced human NPR1 activation as measured by cGMP accumulation in the presence or absence of endogenous ligand

| R5381 ± ligand, EC50 [M] | No Ligand 3.12E−08 | | 40 pM ANP 2.07E−08 | | 80 pM BNP 1.78E−09 | |
|---|---|---|---|---|---|---|
| Anti-R5381 @70 nM | No Ligand | | 40 pM ANP | | 80 pM BNP | |
| | IC50 [M] | Max Inh. (%) | IC50 [M] | Max Inh. (%) | IC50 [M] | Max Inh. (%) |
| REGN6580 | 1.55E−08 | 99 | 2.23E−08 | 102 | 3.32E−08 | 99 |
| REGN6581 | 1.80E−08 | 100 | 2.06E−08 | 104 | 3.50E−08 | 99 |
| REGN9035 | 4.60E−08 | 100 | 2.66E−08 | 104 | 4.13E−08 | 97 |
| REGN9037 | 3.63E−08 | 99 | 1.76E−08 | 101 | 3.81E−08 | 97 |
| Isotype control | ND | 27 | ND | 28 | ND | 6 |

ND: not determined;
Max Inh.: maximum inhibition.

Anti-R5381 antibodies were found to inhibit R5381-induced hNPR1 activation in the absence of endogenous ligand or in the presence of 40 pM ANP, or 80 pM BNP. Cells were incubated with increasing concentrations of ANP, BNP, R5381 or Isotype control (REGN1945) alone, or 70 nM R5381 in the presence or absence of constant concentration of ANP or BNP. The fluorescence intensity was detected using an EnVision (excitation=320 nm, emission=620 nm/665 nm) and the FRET ratio and cGMP concentration were calculated as described in the experimental procedure.

Example 7

Blocking ELISA Assay hNPR1.ecto.mmh (of which amino acids 1-441: human NPR1 amino acid G32-E473 from translation of NM_000906.3, and amino acids 442-469: Myc-Myc-hexahistidine tag; SEQ ID NO: 47), at 10 μg/mL in PBS, was coated on 96-well microtiter plates and incubated overnight at 4° C. Nonspecific binding sites were subsequently blocked using a 0.5% (w/v) solution of BSA in PBS (assay Results R5381 activated hNPR1 expressed in HEK293/hNPR1 cells to stimulate cGMP accumulation with EC50 values of 1.78-31.2 nM in the presence or absence of ANP or BNP, where the basal levels of cGMP without antibody were increased due to the constant amount of ANP or BNP (Table 11, below). Isotype control, REGN1945, did not show any measurable activation in dilution buffer. The EC50 values for ANP and BNP were not calculated due to the limit of quantitation at high concentration compared to the cGMP standard curve in this assay.

All the one-armed and bivalent anti-R5381 antibodies blocked 70 nM R5381-induced hNPR1 activation in the presence or absence of 40 pM ANP or 80 pM BNP with IC50 values of 15.5-57.5 nM and maximum inhibition of 97%-106% (Table 11). Isotype control, REGN1945, did not show any significant inhibition of 70 nM R5381-induced hNPR1 activation in the presence or absence of ANP or BNP (Table 11).

Taken together, all the anti-R5381 antibodies showed significant inhibition of R5381-induced hNPR1 activation in the presence or absence of endogenous ligand as measured by cGMP accumulation.

buffer). Anti-R5381 mAbs and isotype control mAb, were three-fold serially diluted from 500 nM to 8.46 pM in assay buffer. In a 96-well dilution plate, 285 pM Biotin-R5381 was mixed with the three-fold serially diluted antibodies and allowed to pre-bind at room temperature (RT) for 1 hour. The final concentrations of anti-R5381 and isotype control mAbs ranged from 333.33 nM to 5.64 pM and the final concentration of Biotin-R5381 was 95 pM. After 1 hour, incubation at RT, the pre-bind reaction mix was transferred to microtiter plates coated with hNPR1.ecto.mmh. The microtiter plates were incubated at RT for 1 hour and then washed with plate washing solution. Biotin-R5381 binding was detected using Poly-HRP Streptavidin protein. The plates were incubated with detection protein for 1 hour at RT and then washed with plate washing solution. The assay plates were developed with TMB colorimetric substrates according to the manufacturer's recommended procedure.

The absorbance at 450 nm for each well was recorded and plotted as the function of the concentration of antibody. Data was analyzed in GraphPad Prism software using a four-parameter logistic equation over an 11-point dose response curve and $IC_{50}$ values were calculated. The calculated $IC_{50}$ value, defined as the concentration of antibody required to reduce 50% binding of Biotin-R5381 to immobilized hNPR1.ecto.mmh, was used as an indicator of blocking potency. Percent blocking at highest anti-R5381 concentration was calculated as an indicator of the ability of the antibodies to block binding of Biotin-R5381 to NPR1 relative to the baseline of the assay. The baseline signal of the assay, defined as 0% binding of Biotin-R5381, was determined from OD450 nm readings from Poly-HRP Streptavidin binding in wells with assay buffer alone. Binding signal of 95 pM Biotin-R5381 in absence of the anti-R5381 was defined as 100% binding or 0% blocking.

Results

The ability of anti-R5381 antibodies to block Biotin-R5381 binding to human NPR1 was assessed using a blocking ELISA assay. The blocking results are summarized in Table 12, below. The percent blockade calculated at highest antibody concentration (333.33 nM) tested, is reported for all antibodies. REGN9035 blocked binding of 95 pM Biotin-R5381 with $IC_{50}[M]$ of 2.04 nM and demonstrated 99.29% blockade at highest tested concentration. REGN9037 blocked binding of 95 pM Biotin-R5381 with $IC_{50}[M]$ of 2.40 nM and demonstrated 99.05% blockade at highest tested concentration.

Anti-R5381 bivalent antibodies REGN6580 and REGN6581, blocked 95 pM Biotin-R5381 binding with $IC_{50}[M]$ values of 381 pM and 543 pM respectively and both mAbs demonstrated 100% blockade at highest concentration. The isotype control mAb (REGN1945), did not show any blocking of Biotin-R5381, under identical assay conditions.

TABLE 12

Summary of IC50[M] values for selected anti-R5381 antibodies blocking 95 pM Biotin-R5381 binding to hNPR1.ecto.mmh (REGN3037)

| REGN# | $IC_{50}[M]$ | Anti-R5381 (single arm and bivalent) mAbs blocking 95pM Biotin-R5381 binding to ELISA plate-coated 1ug/ml hNPR1.ecto.mmh % Blocking with 333.33 nM antibody |
|---|---|---|
| REGN9035 | 2.04E−09 | 99.29 |
| REGN6580 | 3.81E−10 | 100 |
| REGN9037 | 2.40E−09 | 99.05 |
| REGN6581 | 5.43E−10 | 100 |
| Isotype control | not calculated | No blocking |

100% Blocking=$OD_{450nm}$ value of wells with HRP-conjugated secondary protein in assay buffer alone (no Biotin-R5381 binding)

0% Blocking=$OD_{450nm}$ value of wells with HRP-conjugated secondary protein in assay buffer in presence of constant amount of Biotin-R5381 (without Anti-R5381).

Maximum % Blocking =

$$100 - \frac{\left[\text{Experimental Signal}_{(Anti-REGN5381+Biotin-REGN5381)} - \text{Background Signal}_{(buffer\ only)}\right]}{\left[\text{Maximum Signal}_{(Biotin-REGN5381\ Alone)} - \text{Background Signal}_{(buffer\ only)}\right]}$$

Experimental Signal=$OD_{450}$ of Biotin-R5381 binding observed at tested Anti-R5381 concentration Maximum Signal=$OD_{450}$ of 95 pM Biotin-R5381 binding in absence of Anti-R5381

Background Signal=$OD_{450}$ of Poly-HRP Streptavidin binding in assay buffer only control ELISA-based methods were used to assess the blocking of Biotin-R5381 binding to ELISA plate coated hNPR1.ecto.mmh (SEQ ID NO: 47) in presence of a range of concentrations of one armed anti-R5381 mAbs, REGN9035 and REGN9037. As controls, respective bivalent mAbs REGN6580 and REGN6581, and isotype control mAb were also tested. Percent blocking at highest mAb concentration (333.33 nM) and blocking $IC_{50}[M]$ values of the mAbs are tabulated in Table 12, above. Molarity [M] indicates antibody concentration for mAbs.

Example 8

Circulating Immune Complex Formation Between R5381 and Anti-R5381

The potential to form circulating immune complexes (CIC) between R5381 and anti-R5381 antibodies was tested using Microvue C1q-CIC kit developed by Quidel. This assay was performed according to the manufacturer's instructions. Antigen and antibody samples were combined at either 1:1 or 1:10 ratios and incubated at 37° C. for 30 minutes to initiate complex formation. The antibody-antigen samples, as well as positive and negative heat aggregated gamma globin (HAGG) controls, were then diluted 1:50 into C1q coated test plates. Kit standards were added directly into C1q coated test plates. Test plates were then incubated at RT for 1 hour. Unbound antibodies, antigens or complexes were washed from the plates using a 1× wash buffer. An HRP-conjugated detection antibody was added to test plates and incubated at RT for 30 minutes after which unbound HRP-conjugated detection antibody was washed from plates using 1× wash buffer. HRP substrate was added to the test plates and incubated at RT for 30 minutes. An acidic stopping solution was then applied to inactivate the HRP enzyme. The plates were then read on a Perkin Elmer Victor X5 plate reader at 405 nM.

The raw data was background subtracted, and MicroVue C1q-CIC kit standards were used to plot a linear standard curve that was analyzed by linear regression. The sample and HAGG standards values (μg Eq/mL) were then calculated using a linear regression equation.

Results

HAGG High and low controls were included on each plate. According to the manufacturer's instructions any sample with a value lower than 4.0 μg Eq/mL is considered negative. The potential for R5381 to form CICs with anti-R5381 antibodies was investigated using the MicroVue C1q-CIC kit. The results are summarized in Tables 13A and 13B, below. The final value and presence of CIC is indicated. No CIC was detected in any of the experimental tested conditions.

TABLE 13A

Clq-ClC assay Plate 1

| Antibody (REGN#) | Antigen (REGN#) | Final Value (ug Eq/mL) | Result (Pos/Neg) |
|---|---|---|---|
| 1 µM REGN6580 | 100 nM R5381 | 0.20 | Neg |
| 100 nM REGN6580 | 100 nM R5381 | 0.22 | Neg |
| 1 µM REGN9035 | 100 nM R5381 | 0.29 | Neg |
| 100 nM REGN9035 | 100 nM R5381 | 0.18 | Neg |
| 1 µM Isotype control | 100 nM R5381 | 0.30 | Neg |
| 100 nM Isotype control | 100 nM R5381 | 0.31 | Neg |
| 1 µM REGN6580 | 100 nM Isotype control | 0.16 | Neg |
| 100 nM REGN6580 | 100 nM Isotype control | 0.11 | Neg |
| 1 µM REGN9035 | 100 nM Isotype control | 0.20 | Neg |
| 100 nM REGN9035 | 100 nM Isotype control | 0.15 | Neg |
| 1 µM Isotype control | 100 nM Isotype control | 0.17 | Neg |
| 100 nM Isotype control | 100 nM Isotype control | 0.16 | Neg |
| — | 100 nM R5381 | 0.08 | Neg |
| — | 100 nM Isotype control | 0.18 | Neg |
| 1 µM REGN6580 | — | 0.21 | Neg |
| 100 nM REGN6580 | — | 0.22 | Neg |
| 1 µM REGN9035 | — | 0.25 | Neg |
| 100 nM REGN9035 | — | 0.16 | Neg |
| 1 µM Isotype control | — | 0.25 | Neg |
| 100 nM Isotype control | — | 0.20 | Neg |
| High HAGG control | — | 23.9 | |
| Low HAGG control | — | 1.81 | |

TABLE 13B

Clq-ClC assay Plate 2

| Antibody (REGN#) | Antigen (REGN#) | Final Value (ug Eq/mL) | Result (Pos/Neg) |
|---|---|---|---|
| 1 µM REGN6581 | 100 nM R5381 | 0.53 | Neg |
| 100 nM REGN6581 | 100 nM R5381 | 0.65 | Neg |
| 1 µM REGN9037 | 100 nM R5381 | 0.42 | Neg |
| 100 nM REGN9037 | 100 nM R5381 | 0.64 | Neg |
| 1 µM Isotype control | 100 nM R5381 | 0.46 | Neg |
| 100 nM Isotype control | 100 nM R5381 | 0.55 | Neg |
| 1 µM REGN6581 | 100 nM Isotype control | 0.30 | Neg |
| 100 nM REGN6581 | 100 nM Isotype control | 0.35 | Neg |
| 1 µM REGN9037 | 100 nM Isotype control | 0.55 | Neg |
| 100 nM REGN9037 | 100 nM Isotype control | 0.37 | Neg |
| 1 µM Isotype control | 100 nM Isotype control | 0.36 | Neg |
| 100 nM Isotype control | 100 nM Isotype control | 0.41 | Neg |
| — | 100 nM R5381 | 0.39 | Neg |
| — | 100 nM Isotype control | 0.36 | Neg |
| 1 µM REGN6581 | — | 0.62 | Neg |
| 100 nM REGN6581 | — | 0.37 | Neg |
| 1 µM REGN9037 | — | 0.38 | Neg |
| 100 nM REGN9037 | — | 0.58 | Neg |
| 1 µM Isotype control | — | 0.41 | Neg |
| 100 nM Isotype control | — | 0.43 | Neg |
| High HAGG control | — | 21.2 | |
| Low HAGG control | — | 1.92 | |

Example 9

Pharmacokinetic Assessment of Anti-R5381 Antibodies in NPR1$^{hu/hu}$ Mice

Evaluation of the pharmacokinetics of two one-armed anti-R5381 antibodies, REGN9035 and REGN9037 and their respective bivalent parental counterparts, REGN6580 and REGN6581, were conducted in humanized NPR1 mice (mice homozygous for the humanized NPR1 allele, NPR1$^{hu/hu}$). Cohorts contained 5 mice per tested antibody. Mice dosed with REGN6580 and REGN6581 received a single sub-cutaneous (SC) 1 mg/kg dose. Mice dosed with REGN9035 and REGN9037 received a single normalized SC dose based on molar equivalence (0.67 mg/kg) to their parental counterparts. Blood samples were collected at 6 hours and 1, 2, 3, 7, 10, 14, 21 and 30-days post dosing. Blood was processed into serum and frozen at −80° C. until analyzed. The total and functional hIgG serum concentrations of REGN9035, REGN9037, REGN6580 and REGN6581 were measured using the GyroLab xPlore platform (Gyros).

Gyros technology uses an affinity flow-through format for automated immunoassays with laser-induced fluorescence detection. Samples are loaded onto a compact disc (CD) which contains multiple radially arranged nanoliter-scale affinity capture columns. Liquid flow is controlled by centrifugal and capillary forces.

For the measurement of total and functional REGN9035, REGN9037, REGN6580 and REGN6581 concentrations in serum, a test article-specific biotinylated capture reagent (Table 14, below) was added onto a Gyrolab Bioaffy 200 CD containing affinity columns preloaded with streptavidin-coated beads (Dynospheres). The standards used for calibration (Table 14) were run at concentrations ranging from 0.488-2000 ng/mL. Serial dilutions of serum samples were prepared in phosphate buffered saline (PBS) containing 0.5% bovine serum albumin (BSA). Serial dilutions of standards were prepared in PBS+0.5% BSA containing 2% normal mouse serum (NMS). Singlets of serum samples diluted at 1:50 and duplicates of standards were added onto the capture reagent-coated affinity columns at room temperature. Captured human IgG was detected using Alexa-647-conjugated mouse anti-human IgG1/hIgG4 monoclonal antibody (@ 0.5 µg/mL) diluted in Rexxip F buffer (Gyros); the resultant fluorescent signal was recorded in response units (RU) by the GyroLab xPlore instrument. The respective assay's lower limit of quantitation (LLOQ) of 0.05 µg/mL was defined as the lowest concentration on the standard curve for which a Quality Control (QC) sample was determined to consistently deviate less than 25% from the expected concentration (Table 14). Sample concentrations were determined by interpolation from a standard curve that was constructed using a 4-parameter logistic curve fit in Gyrolab Evaluator Software. Average concentrations from 2 replicate experiments were used to calculate final concentrations.

TABLE 14

Assay Conditions For Gyros ImmunoAssays for Human IgG

| Detected human IgG | Capture Reagent | Concentration of Capture Reagent | Standard |
|---|---|---|---|
| REGN9035 (Total) | Biotin-conjugated mouse anti-human kappa light chain constant region mAb | 20 µg/mL | REGN9035 |
| REGN9037 (Total) | | | REGN9037 |
| REGN6580 (Total) | | | REGN6580 |
| REGN6581 (Total) | | | REGN6581 |
| REGN9035 (Functional) | Biotin-conjugated Fab of R5381 | 75 µg/mL | REGN9035 |
| REGN9037 (Functional) | | | REGN9037 |
| REGN6580 (Functional) | | | REGN6580 |
| REGN6581 (Functional) | | | REGN6581 |

Fab, antibody binding fragment

PK parameters were determined by non-compartmental analysis (NCA) using Phoenix® WinNonlin® software Version 6.3 (Certara, L.P., Princeton, NJ) and an extravascular dosing model. Using the respective mean concentration values (total hIgG) for each antibody, all PK parameters including observed maximum concentration in serum ($C_{max}$), estimated half-life observed ($t_{1/2}$), area under the concentration curve versus time up to the last measurable concentration ($AUC_{last}$), and antibody clearance rates (Cl) were determined using a linear trapezoidal rule with linear interpolation and uniform weighting.

Results

Following 1 mg/kg (or dose equivalent) SC administration of the anti-R5381 Abs in NPR1$^{hu/hu}$ mice, REGN9035, REGN9037, REGN6580, and REGN6581 exhibited similar dose normalized maximum concentrations of total hIgG in serum ($C_{max/D}$=10.3, 9.23, 9.3, and 11.4 mg/mL, respectively). In addition, REGN9035, REGN9037, REGN6580, and REGN6581 also exhibited similar half-life values ($T_{1/2}$=18.1, 17.1, 16.1, and 15.4 days, respectively), dose normalized drug exposure values ($AUC_{last/D}$=204, 174, 165, and 205 (d*mg/mL)/(mg/kg), respectively) and clearance rates (Cl=5.0, 6.1, 4.9, and 3.7 mL/day/kg, respectively). Furthermore, total and functional human IgG concentrations of REGN9035, REGN9037, REGN6580, and REGN6581 were comparable over all measured timepoints. No measurable differences were seen in the PK profiles of the one-armed antibodies, REGN9035 and REGN9037 in comparison to their bivalent counterparts, REGN6580 and REGN6581 in NPR1$^{hu/hu}$ mice.

Figure 2:
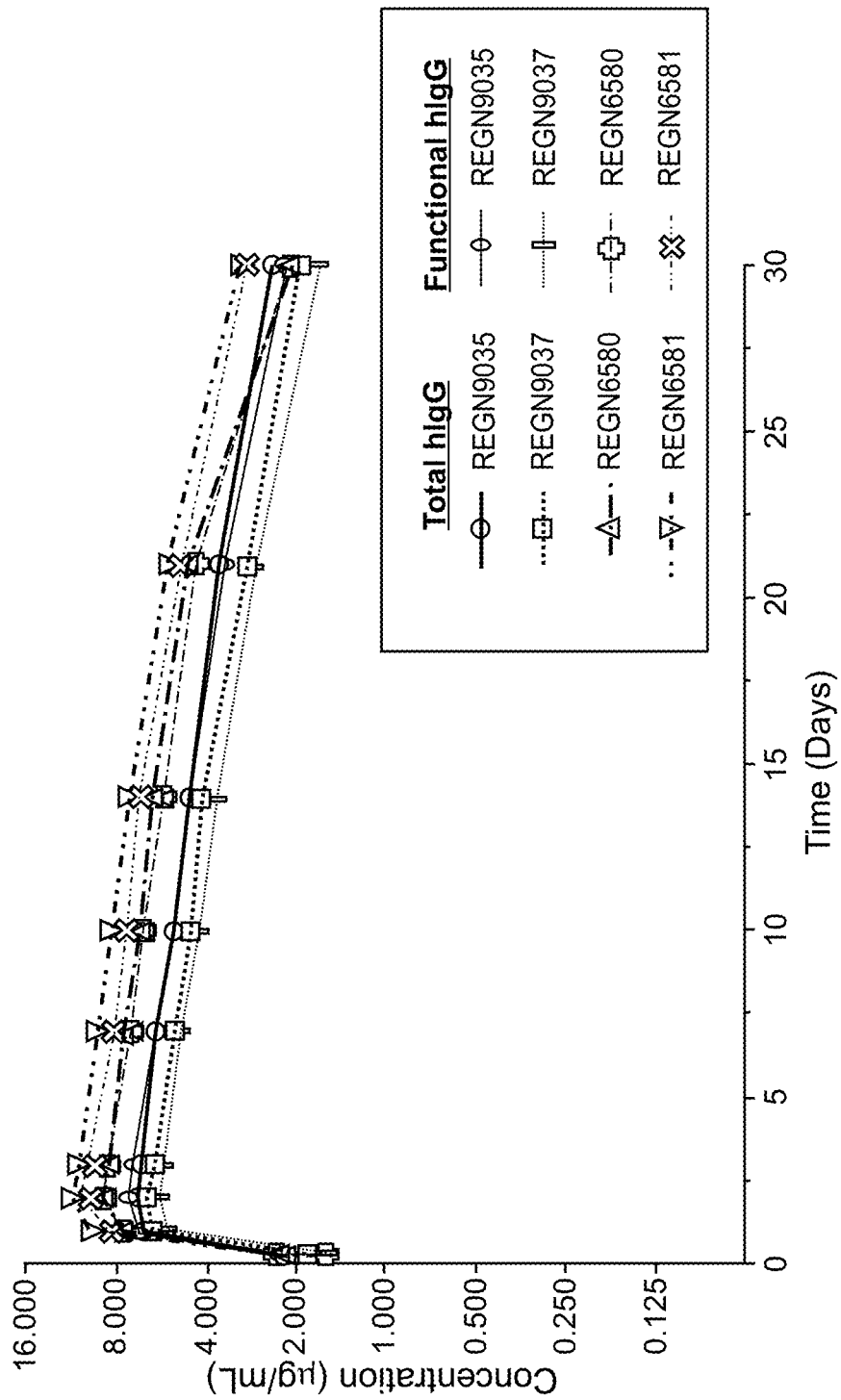
FIG. 2 provides, in line graph form, the pharmacokinetic profiles of anti-R5381 antibodies REGN9035, REGN9037, REGN6580, and REGN6581 in NPR1$^{hu/hu}$ mice.

A summary of the data for total and functional antibody concentrations are summarized in Table 15, below, mean PK parameters are described in Table 16, below, and mean total antibody concentrations versus time are shown in FIG. 2.

TABLE 15

Mean Serum Concentrations (±SEM) of Total and Functional hIgG Following a Single 1 mg/kg (or Dose Equivalent) Subcutaneous Injection of REGN9035, REGN9037, REGN6580 or REGN6581 Antibodies in NPR1$^{hu/hu}$ Mice Over Time

| | | Total hIgG Concentration | | Functional hIgG Concentration | |
|---|---|---|---|---|---|
| | | 1 mg/kg (0.67 mg/kg, dose normalized) | | | |
| Antibody | Time (d) | Mean (µ/mL) | +/− SEM | Mean (µ/mL) | +/− SEM |
| REGN9035 | 0.25 | 2.2 | 0.18 | 2.2 | 0.17 |
| | 1 | 6.5 | 0.25 | 6.3 | 0.24 |
| | 2 | 6.8 | 0.23 | 7.4 | 0.29 |
| | 3 | 6.7 | 0.17 | 7.0 | 0.24 |
| | 7 | 5.9 | 0.27 | 5.9 | 0.25 |
| | 10 | 5.2 | 0.26 | 5.1 | 0.26 |
| | 14 | 3.9 | 0.71 | 3.8 | 0.76 |
| | 21 | 2.9 | 0.70 | 2.8 | 0.70 |
| | 30 | 1.9 | 0.49 | 1.8 | 0.44 |
| REGN9037 | 0.25 | 1.8 | 0.18 | 1.7 | 0.16 |
| | 1 | 6.2 | 0.26 | 5.5 | 0.13 |
| | 2 | 6.2 | 0.14 | 5.7 | 0.08 |
| | 3 | 5.9 | 0.32 | 5.5 | 0.21 |
| | 7 | 5.1 | 0.15 | 4.8 | 0.05 |
| | 10 | 4.5 | 0.05 | 4.2 | 0.09 |
| | 14 | 4.2 | 0.18 | 3.7 | 0.10 |
| | 21 | 3.0 | 0.10 | 2.8 | 0.10 |
| | 30 | 2.0 | 0.14 | 1.7 | 0.13 |
| REGN6580 | 0.25 | 1.6 | 0.20 | 1.7 | 0.21 |
| | 1 | 7.5 | 0.30 | 7.8 | 0.56 |
| | 2 | 9.0 | 0.45 | 8.6 | 0.40 |
| | 3 | 8.6 | 0.53 | 8.4 | 0.48 |
| | 7 | 7.5 | 0.52 | 7.0 | 0.50 |
| | 10 | 6.7 | 0.56 | 6.4 | 0.53 |
| | 14 | 6.1 | 0.56 | 5.6 | 0.50 |
| | 21 | 4.6 | 0.57 | 4.3 | 0.55 |
| | 30 | 2.2 | 0.57 | 2.1 | 0.55 |
| REGN6581 | 0.25 | 2.4 | 0.38 | 2.4 | 0.36 |
| | 1 | 9.7 | 0.68 | 9.4 | 0.60 |
| | 2 | 11.2 | 0.66 | 10.7 | 0.39 |
| | 3 | 10.6 | 0.47 | 9.9 | 0.53 |
| | 7 | 9.3 | 0.56 | 8.1 | 0.52 |
| | 10 | 8.4 | 0.37 | 7.4 | 0.45 |
| | 14 | 7.2 | 0.38 | 6.6 | 0.37 |
| | 21 | 5.3 | 0.39 | 4.8 | 0.31 |
| | 30 | 3.0 | 0.32 | 2.9 | 0.32 |

Abbreviations:
Time = Time in days post single-dose injection;
d = Day of study;
SEM = Standard Error of the Mean PK parameters were derived from mean concentration versus time profiles of total hIgG concentrations.
$T_{1/2}$ and $AUC_{last}$ are based on concentrations out to day 30. The mean ± SEM value for each PK parameter is shown for all dose groups.

TABLE 16

Summary of Pharmacokinetic Parameters

| | | 1 mg/kg (0.67 mg/kg dose normalized) | | | |
|---|---|---|---|---|---|
| Parameter | Units | REGN9035 | REGN9037 | REGN6580 | REGN6581 |
| $C_{max}$ | µg/mL | 6.9 ± 0.2 | 6.5 ± 0.2 | 9.3 ± 0.5 | 11.4 ± 0.7 |
| $C_{max/D}$ | µg/mL/mg/kg | 10.3 ± 0.3 | 9.23 ± 0.5 | 9.3 ± 0.5 | 11.4 ± 0.7 |

TABLE 16-continued

Summary of Pharmacokinetic Parameters

| | | 1 mg/kg (0.67 mg/kg dose normalized) | | | |
|---|---|---|---|---|---|
| Parameter | Units | REGN9035 | REGN9037 | REGN6580 | REGN6581 |
| $T_{1/2}$ | d | 18.1 ± 1.1 | 17.1 ± 1.2 | 16.1 ± 2.3 | 15.4 ± 1.1 |
| $AUC_{last}$ | d * µg/mL | 136 ± 4 | 117 ± 3.1 | 165 ± 19 | 205 ± 11 |
| $AUC_{last/D}$ | (d * µg/mL)/(mg/kg) | 204 ± 5.9 | 174 ± 4.6 | 165 ± 19 | 205 ± 11 |
| Cl | mL/day/kg | 5.0 ± 0.3 | 6.1 ± 0.3 | 4.9 ± 1.0 | 3.7 ± 0.3 |

Abbreviations:
$AUC_{last}$ = area under the curve from the time of dosing to the last measuable concentration;
$AUC_{last/D}$ = AUC last dose normalized to 1 mg/kg dosing;
$t_{1/2}$ = terminal half-life of elimination;
$C_{max}$ = peak concentration;
$C_{max/D}$ = Cmax dose normalized to 1 mg/kg dosing;
Cl = clearance rate of antibody overtime.;
SEM = standard error of the mean.

Example 10

Serum Concentration Analysis of Total R5381 (Anti-NPR1 mAb) after Rescue by Anti-R5381 Antibodies Sample concentration analysis of serum from an in vivo study evaluating the effectiveness of bivalent anti-R5381 mAbs, REGN6580 and REGN6581 in comparison to an isotype control antibody, REGN1945, at reversing the blood pressure lowering effects of R5381. The study was performed in telemetered normotensive humanized NPR1 (mice homozygous for the humanized NPR1 allele, NPR1$^{hu/hu}$) mice. In short, cohorts contained 5 mice per tested antibody. All mice were dosed with a single subcutaneous (SC) 5 mg/kg dose of R5381. Three days later, mice received either a single intravenous (IV) 50 mg/kg dose of REGN6580, REGN6581 or isotype control, REGN1945. Blood samples were collected at 7 and 22-days post initial R5381 dosing. Blood was processed into serum and frozen at −80° C. until analyzed. The serum concentrations of total R5381 were measured using the GyroLab xPlore platform (Gyros).

Gyros technology uses an affinity flow-through format for automated immunoassays with laser-induced fluorescence detection. Samples are loaded onto a compact disc (CD) which contains multiple radially arranged nanoliter-scale affinity capture columns. Liquid flow is controlled by centrifugal and capillary forces.

For the measurement of total R5381 in serum, an immunoassay was run. Mice dosed with R5381 followed by dosing with an anti-R5381 mAb are presumed to form antibody: anti-idiotype complexes in serum. (R5381: REGN6580 or R5381: REGN6581). In order to accurately measure the total R5381 antibody concentrations of these samples, a dissociation step was performed at the start of the assay. Briefly, to measure total R5381, a test article-specific biotinylated capture reagent, REGN6712 at a concentration of 75 µg/mL, was pre-incubated for 4 hours at 37° C. with serum samples diluted at 1:250 or standards diluted at concentrations ranging from 0.244 to 1000 ng/mL. Dilutions of serum samples were prepared in phosphate buffered saline (PBS) containing 0.5% bovine serum albumin (BSA) (+capture reagent), and serial dilutions of standards (R5381) were prepared in PBS+0.5% BSA containing 0.4% normal mouse serum (NMS) (+capture reagent). Following a 4-hour 37° C. pre-incubation of capture reagents with samples or standards, diluted singlets of serum samples (+capture reagent) and diluted duplicates of standards (+capture reagent) were added onto a Gyrolab Bioaffy 200 CD containing affinity columns preloaded with streptavidin-coated beads (Dynospheres). Captured human IgG was detected using 0.5 µg/mL Alexa-647-conjugated mouse anti-human IgG1/hIgG4 monoclonal antibody diluted in Rexxip F buffer (Gyros); the resultant fluorescent signal was recorded in response units (RU) by the GyroLab xPlore instrument. The respective assay's lower limit of quantitation (LLOQ) of 0.1 µg/mL was defined as the lowest concentration on the standard curve for which a pre-complexed Quality control (QC) (R5381: REGN6580, R5381: REGN6581) sample was determined to consistently deviate less than 25% from the expected concentration.

For the measurement of total R5381 concentrations in serum from mice dosed with R5381 followed by a non-binding control antibody (REGN1945), a dissociation step was not necessary. Total R5381 concentrations were measured as follows. Briefly, a test article-specific biotinylated capture reagent, mAb36313 at 50 µg/mL was added onto the Gyrolab Bioaffy 200 CD containing affinity columns preloaded with streptavidin-coated beads (Dynospheres) at room temperature. The standard (R5381) used for calibration in this assay was diluted at concentrations ranging from 0.488 to 2000 ng/mL. Serial dilutions of standards were prepared in PBS+0.5% BSA containing 1% normal mouse serum (NMS). Singlets of serum samples diluted at 1:100 and duplicates of standards were added onto the capture reagent coated affinity columns at room temperature. Captured human IgG was detected using 0.5 µg/mL Alexa-647-conjugated mouse anti-human IgG1/hIgG4 monoclonal antibody diluted in Rexxip F buffer (Gyros); the resultant fluorescent signal was recorded in RU by the GyroLab xPlore instrument. The respective assay's LLOQ of 0.05 µg/mL was defined as the lowest concentration on the standard curve for which a QC sample was determined to consistently deviate less than 25% from the expected concentration.

Sample concentrations were determined by interpolation from a standard curve that was constructed using a 4-parameter logistic curve fit in Gyrolab Evaluator Software. Average concentrations from 2 replicate experiments were used to calculate final concentrations.

Calculation of Mean Concentrations

Individual and mean concentrations below the LLOQ (<LLOQ) are reported as below the limit of quantitation (BLQ). If >50% of the individual values are BLQ, the mean value for that time point is reported as BLQ. If ≤50% of the individual values within a treatment group are BLQ and, using zero as the BLQ value, the mean value is arithmetically BLQ, then the mean value is reported as BLQ. If ≤50% of the individual values within a treatment group are BLQ and, using zero as the BLQ value, the mean value is arithmetically ≥LLOQ, then this arithmetic value is reported.

Results

Seven days post 5 mg/kg dosing of R5381 in NPR1$^{hu/hu}$ mice followed three days later by administration of 50 mg/kg of rescue reagents REGN6580, REGN6581, or isotype control mAb (REGN1945), resulted in lower average serum concentrations of total R5381 in mice receiving the anti-idiotype antibodies as compared to mice receiving a dose of isotype control. This indicates that anti-idiotype antibodies, REGN6580 and REGN6581, were responsible for the faster clearance of R5381 seen in mice when given these anti-idiotype mAbs as compared to mice dosed with isotype control.

Mice dosed with R5381 and followed three days later (7 days post initial R5381 dosing) by a dose of REGN6580 or REGN6581 had total R5381 concentrations of 3.6 or 7.4 μg/mL, respectively. In comparison, mice dosed 3 days later with Isotype control resulted in total R5381 concentrations of 30.5 μg/mL. Analysis of serum taken 22 days post R5381 dosing followed by dosing of the anti-idiotype antibodies, resulted in undetectable concentrations of total R5381, whereas serum concentrations of total R5381 in the Isotype control dosed group were still approximately 6 μg/mL.

A summary of the data for total R5381 serum concentrations in mice rescued by IV dosing of REGN6580, REGN6581, or isotype control, REGN1945, are found in Table 17, below.

TABLE 17

Mean Serum Concentrations (±SEM) of Total IgG Following a Single 5 mg/kg Subcutaneous Injection of R5381 Followed Three Days Later by a Single 50 mg/kg Intravenous Injection of REGN6580 or REGN6581 Anti-Idiotype Antibodies or Isotype Control in NPR1hu/hu Mice at Days 7 and 22

| | | Total hIgG Concentration Total R5381 | |
|---|---|---|---|
| Antibody Group | Time (d) | Mean (μg/mL) | +/− SEM |
| R5381 + REGN6580 | 7 | 3.6 | 0.4 |
| | 22 | BLQ | NA |
| R5381 + REGN6581 | 7 | 7.4 | 2.7 |
| | 22 | BLQ | NA |
| R5381 + Isotype control | 7 | 30.5 | 3 |
| | 22 | 5.9 | 2.8 |

Abbreviations:
Time, Time in days post single-dose injection;
d, Day of study;
BLQ, Below the limit of quantitation;
NA, not applicable;
SEM = Standard Error of the Mean

Example 11

Evaluation of Reversal of R5381-Induced Blood Pressure Lowering Using a Single 50 mg/kg Intravenous Dose of Bivalent Anti-R5381 mAbs in Normotensive NPR1$^{hu/hu}$ Mice In order to assess the effects of bivalent anti-R5381 antibodies at reversing the blood pressure lowering induced by R5381 in telemetered normotensive NPR1$^{hu/hu}$ mice, male NPR1$^{hu/hu}$ mice (n=20) aged ~18-20 weeks were implanted with PA-C10 telemeters (DSI, St. Paul, MN) and allowed to recover for at least 7 days. Animals were stratified into groups (Groups 1-4) based on pre-study systolic blood pressures and body weight. Animals were individually housed under standard conditions (Temperatures of 64° F. to 84° F. (18° C. to 29° C.); relative humidity of 30% to 70%) and a 12-hour light/12-hour dark cycle was maintained. Food (Research Diets Standard pellet chow) and water were provided ad libitum.

The test proteins were administered to the appropriate animals by single subcutaneous injection on Day 0. The rescue agents were administered to the appropriate animals by single intravenous injection on Day 3. The dose volume for each animal was based on the most recent body weight measurement.

TABLE 18

Summary of Doses and Dose Groups

| Group No. | Test Article | Dose (mg/kg s.c.) | Rescue Article | Dose (mg/kg i.v.) | Number of Animals Males |
|---|---|---|---|---|---|
| 1 | PBS | 0 | PBS | 0 | 5 |
| 2 | REGN5381 | 5 | IgG4P isotype control mAb | 50 | 5 |
| 3 | | | REGN6580 | | 5 |
| 4 | | | REGN6581 | | 5 |

Systolic pressure, diastolic pressure, pulse pressure, mean arterial pressure and heart rate were collected for 10 seconds every 10 minutes for the duration of the testing period. Data were binned and assessed accordingly for acute (hourly bins) and chronic (24-hr bins) reversal of R5381-induced blood pressure lowering. Day 21/22 cyclic guanosine monophosphate (cGMP) concentrations in urine were assessed by ELISA. Gross absolute and relative heart weights were collected at necropsy. All data are presented as mean±SEM.

Results

Figure 3:
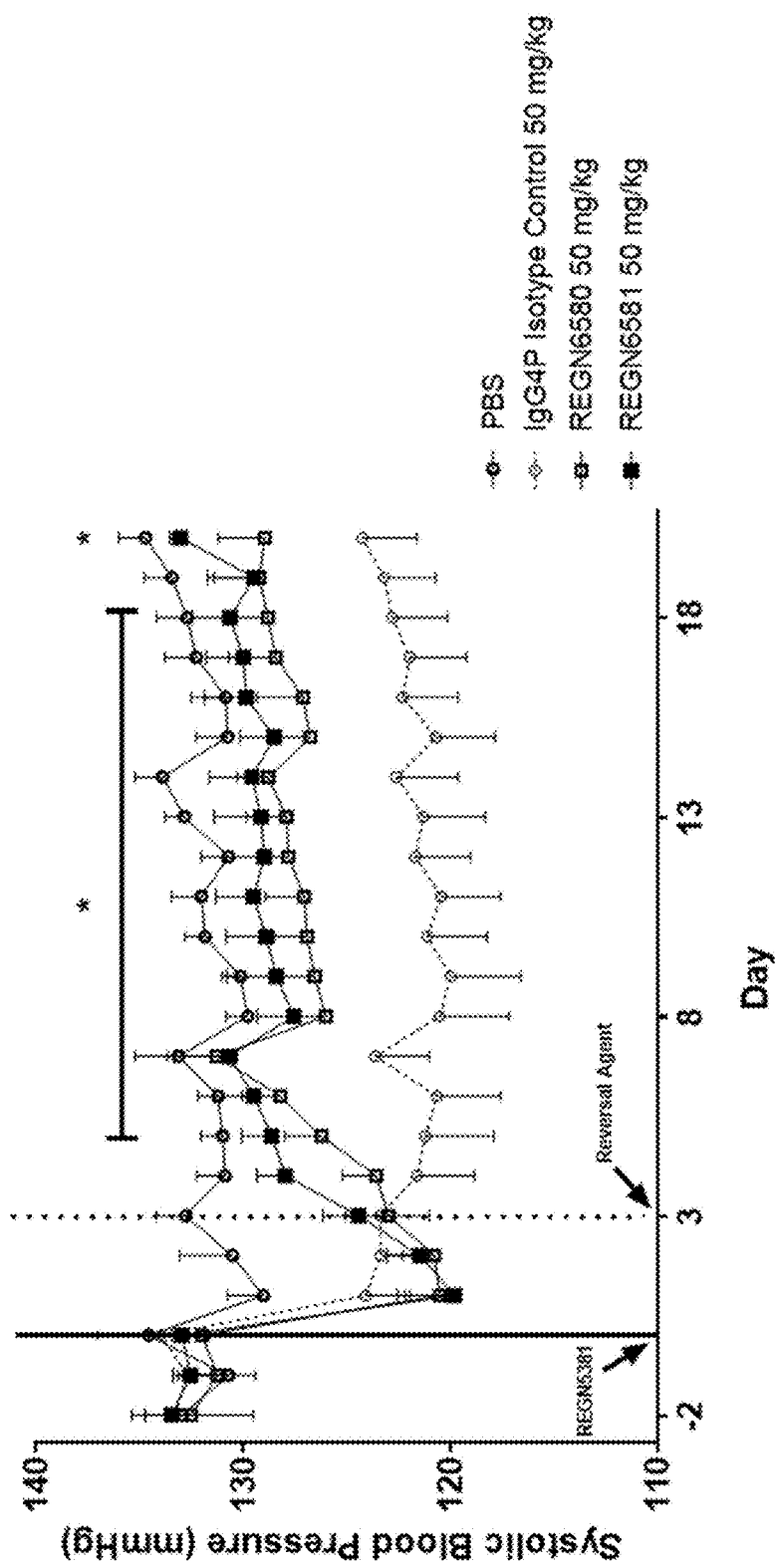
FIG. 3 shows, in line graph form, the effects of bivalent anti-R5381 mAbs on reversing R5381-induced systolic blood pressure-lowering in normotensive NPR1$^{hu/hu}$ mice. Telemetered normotensive NPR1$^{hu/hu}$ mice were randomized into groups based off of systolic blood pressures and body weight. Animals were given a single 5 mg/kg subcutaneous injection of R5381 or PBS as described in Table 18. Animals were then given a single 50 mg/kg intravenous injection of an anti-R5381 bivalent mAb or PBS as described in Table 18. All values are mean pressures over 24 hours for days −2-20±SEM, n=4-5 per group. Statistics— two-way ANOVA with Dunnett's; *$p<0.05$ vs. isotype control mAb.
Figure 4:
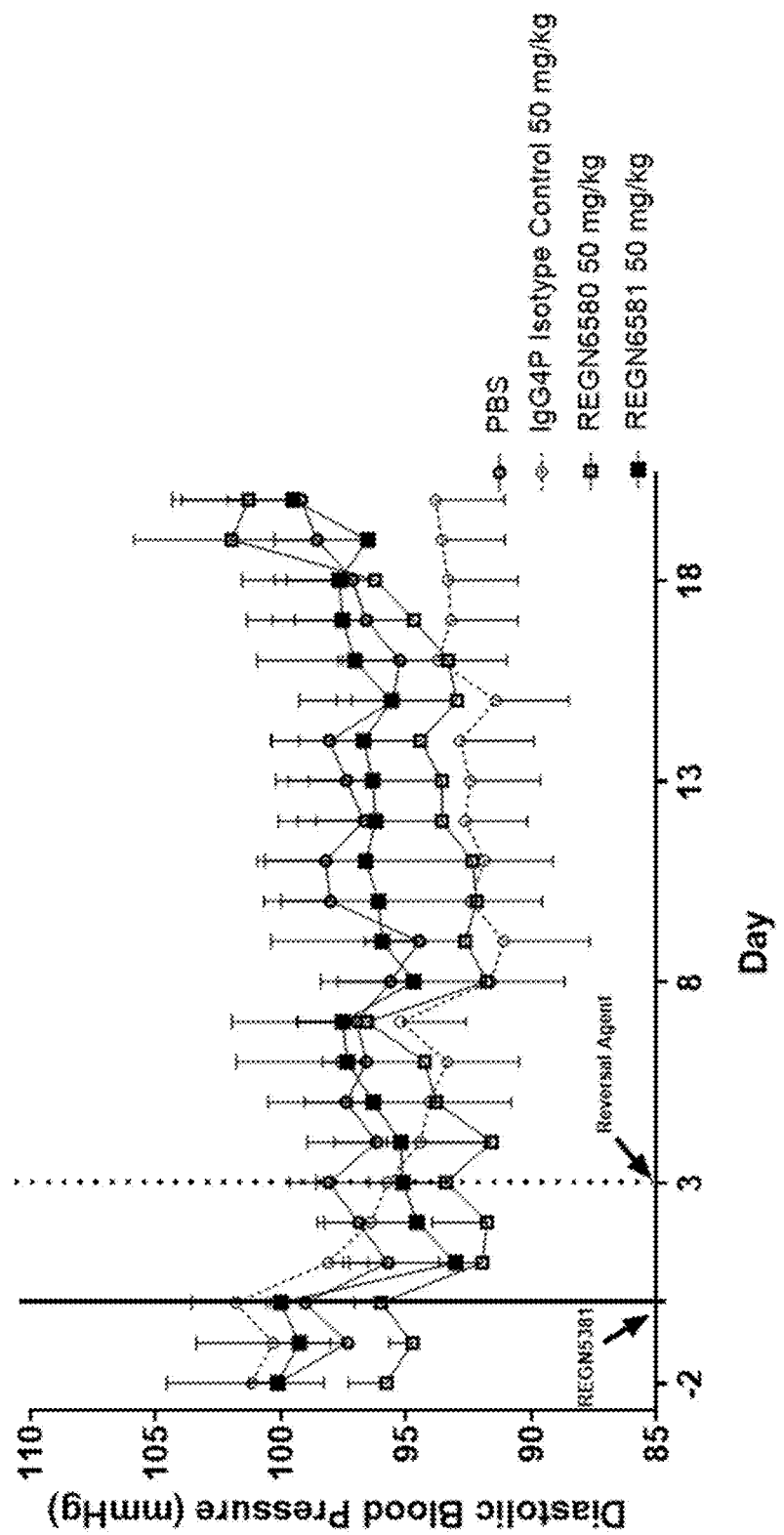
FIG. 4 shows, in line graph form, the effects of bivalent anti-R5381 mAbs on reversing R5381-induced diastolic blood pressure-lowering in normotensive NPR1$^{hu/hu}$ mice. Telemetered normotensive NPR1$^{hu/hu}$ mice were randomized into groups based off of systolic blood pressures and body weight. Animals were given a single 5 mg/kg subcutaneous injection of R5381 or PBS as described in Table 18. Animals were then given a single 50 mg/kg intravenous injection of an anti-R5381 bivalent mAb or PBS as described in Table 18. All values are mean pressures over 24 hours for days −2-20±SEM, n=4-5 per group. Statistics— two-way ANOVA with Dunnett's; *$p<0.05$ vs. isotype control mAb.
Figure 5:
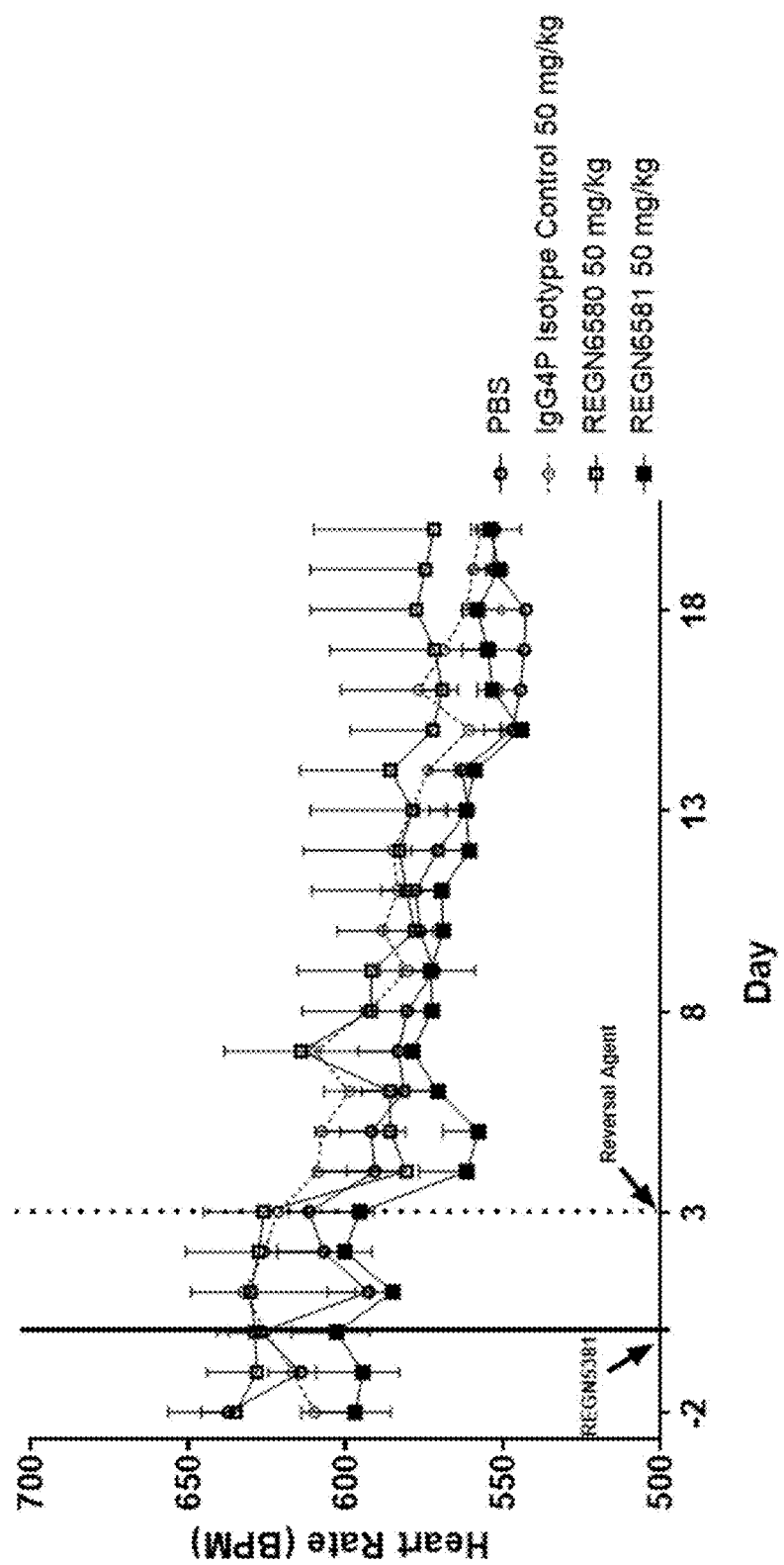
FIG. 5 shows, in line graph form, the effects of bivalent anti-R5381 mAbs on reversing R5381 mAb-induced heart rate effects in normotensive NPR1$^{hu/hu}$ mice. Telemetered normotensive NPR1$^{hu/hu}$ mice were randomized into groups based off of systolic blood pressures and body weight. Animals were given a single 5 mg/kg subcutaneous injection of R5381 or PBS as described in Table 18. Animals were then given a single 50 mg/kg intravenous injection of an anti-R5381 bivalent mAb or PBS as described in Table 18. All values are mean heart rates over 24 hours for days −2-20±SEM, n=4-5 per group. Statistics—two-way ANOVA with Dunnett's.
Figure 6:
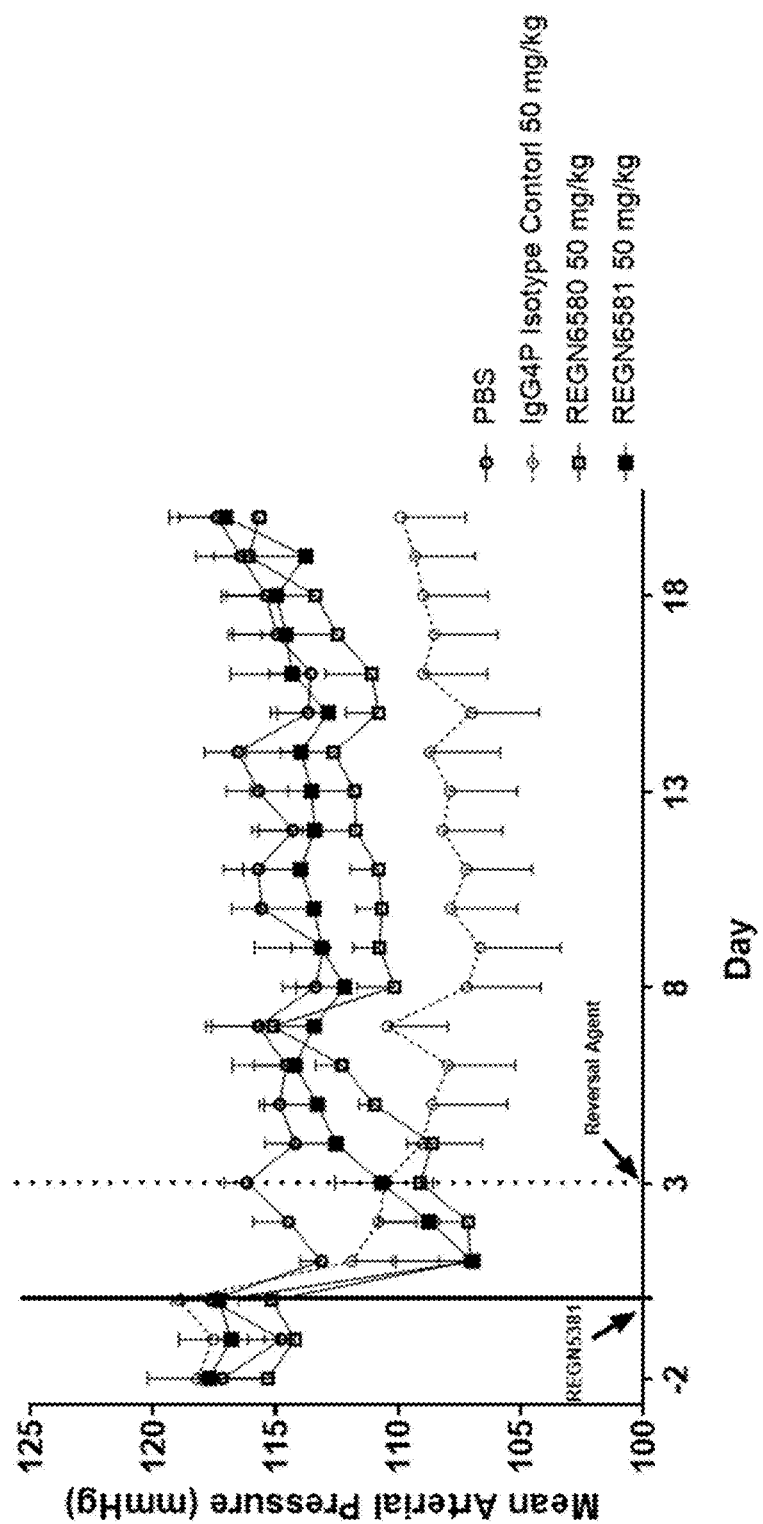
FIG. 6 shows, in line graph form, the effects of bivalent anti-R5381 mAbs on reversing R5381 mAb-induced mean arterial blood pressure-lowering in normotensive NPR1$^{hu/hu}$ mice. Telemetered normotensive NPR1$^{hu/hu}$ mice were randomized into groups based off of systolic blood pressures and body weight. Animals were given a single 5 mg/kg subcutaneous injection of R5381 or PBS as described in Table 18. Animals were then given a single 50 mg/kg intravenous injection of an anti-R5381 bivalent mAb or PBS as described in Table 18. All values are mean pressures over 24 hours for days −2-20±SEM, n=4-5 per group. Statistics— two-way ANOVA with Dunnett's; *$p<0.05$ vs. isotype control mAb.

The in vivo screen of bivalent anti-R5381 antibodies REGN6580 and REGN6581 demonstrated rapid and persistent reversal of the blood pressure lowering effects of R5381 (FIG. 3). Both REGN6580 and REGN6581, when administered intravenously 3 days after initial dosing of R5381, were able to increase pressures back to baseline levels. The initial drop in pressure of 6-8 mmHg (Table 19, below) compared to time-matched controls was reversed within 3 days following administration of either REGN6580 or REGN6581 (FIG. 3).

TABLE 19

Day 1-2 - Mean Blood Pressures and Heart Rates Prior to Administration of Rescue Agent

| Group | Test Article | Systolic (mmHg) | Diastolic (mmHg) | Pulse Pressure (mmHg) | Mean Arterial (mmHg) | Heart Rate (BPM) |
|---|---|---|---|---|---|---|
| 1 | PBS | 129 ± 1 | 96 ± 1 | 33 ± 0 | 114 ± 1 | 600 ± 7 |
| 2 | R5381 | 123 ± 0** | 97 ± 1 | 26 ± 0*** | 111 ± 1 | 629 ± 3* |
| 3 | | 121 ± 0*** | 92 ± 0* | 28 ± 0*** | 107 ± 0** | 629 ± 1* |
| 4 | | 121 ± 1*** | 94 ± 1 | 27 ± 0*** | 108 ± 1** | 593 ± 8 |

Telemetered normotensve NPR1$^{hu/hu}$ mice were randomized into groups based on systolic blood pressures and body weight. Animals were given a single 5 mg/kg subcutaneous injection of NPR1 agonist mAb R5381 or PBS as described in Table 18. All values are mean ± SEM, n = 4-5 per group. Statistics - one-way ANOVA with Dunnett's; *p < 0.05 vs. PBS; p < 0.01 vs. PBS; *p < 0.001 vs. PBS.

The durability of reversal was maintained for the 22-day duration of the study, with statistically significant differences in all hemodynamic parameters for animals dosed with REGN6580 or REGN6581 when compared to animals administered R5381 and isotype control mAb (Table 20, below).

TABLE 20

Day 4-20 Mean Blood Pressures and Heart Rates Following Administration of Rescue Agent

| Group | Test Article | Rescue Article | Systolic (mmHg) | Diastolic (mmHg) | Pulse Pressure (mmHg) | Mean Arterial (mmHg) | Heart Rate (BPM) |
|---|---|---|---|---|---|---|---|
| 1 | PBS | PBS | 132 ± 0**** | 97 ± 0**** | 35 ± 0**** | 115 ± 0**** | 567 ± 4** |
| 2 | R5381 | isotype control mAb | 122 ± 0 | 93 ± 0 | 29 ± 0 | 108 ± 0 | 582 ± 4 |
| 3 | | REGN6580 | 128 ± 0**** | 95 ± 1* | 33 ± 1**** | 112 ± 0**** | 582 ± 3 |
| 4 | | REGN6581 | 129 ± 0**** | 97 ± 0**** | 33 ± 0**** | 114 ± 0**** | 562 ± 2*** |

Telemetered normotensive NPR1$^{hu/hu}$ mice were randomized into groups based on systolic blood pressures and body weight. Animals were given a single 5 mg/kg subcutaneous injection of NPR1 agonist mAb R5381 or PBS on study day 0 followed by either isotype control mAb or anti-R5381 on study day 3 as described in Table 18. All values are mean ± SEM, n = 4-5 per group. Statistics - one way ANOVA with Dunnett's; *p < 0.05 vs. Isotype control; p < 0.01 vs. Isotype Control; *p < 0.001 vs. Isotype Control; ****p < 0.0001 vs. Isotype Control.

When compared to PBS control animals, no statistically significant differences were noted (Table 20, FIGS. 3-6) following administration of either REGN6580 or REGN6581, indicating full and persistent reversal of R5381-induced blood pressure lowering effects.

Both bivalent anti-R5381 antibodies REGN6580 and REGN6581 attenuated the reduction in relative heart weight as indicated by no statistically significant difference in heart weight to tibia weight in either reversal agent-dosed group compared to PBS-dosed animals (Table 21, below).

TABLR 21

Gross and Relative Heart Weight Following Administration of Reversal Agent

| Group | Heart Weight (mg) | Brain Weight (mg) | Tibia Length (mm) | Heart Weight: Brain Weight | Heart Weight: Tibia Length |
|---|---|---|---|---|---|
| PBS + PBS | 148 ± 4 | 493 ± 11 | 17.6 ± 0.2 | 300 ± 10 | 8.4 ± 0.1 |
| R5381 + isotype control mAb | 133 ± 4 | 473 ± 20 | 18.2 ± 0.2 | 280 ± 9 | 7.3 ± 0.2** |
| R5381 + REGN6580 | 137 ± 2 | 463 ± 5 | 17.4 ± 0.2 | 296 ± 5 | 7.9 ± 0.1 |
| R5381 + REGN6581 | 138 ± 4 | 458 ± 12 | 17.8 ± 00.2 | 302 ± 12 | 7.8 ± 0.2 |

Telemetered normotensive NPR1$^{hu/hu}$ mice were randomized into groups based on systolic blood pressures and body weight. Animals were given a single 5 mg/kg subcutaneous injection of NPR1 agonist mAb R5381 or PBS on study day 0 followed by either isotype control mAb or anti-R5381 on study day 3 as described in TABLE 18. All values are mean ± SEM, n = 4-5 per group. Statistics - one-way ANOVA with Tukey's; **p < 0.01 vs. PBS.

No effect on urine volume was noted with any of the test or rescue articles that were delivered (Table 22, below).

TABLE 22

Day 22 Urine Volumes and Urinary cGMP Levels

| Group | Test Article: | Reversal Agent | Urine Volume (mL/day)g) | Urinary cGMP (pmol/mL) | Urinary cGMP (pmol/day) |
|---|---|---|---|---|---|
| 1 | PBS | PBS | 2.1 ± 0.1* | 6568 ± 1143 | 13474 ± 2678 |
| 2 | R5381 (5 mg/kg) | Isotype Control (50 mg/kg) | 1.0 ± 0.2 | 6855 ± 937 | 6809 ± 457 |
| 3 | | REGN6580 (50 mg/kg) | 1.4 ± 0.2 | 6389 ± 1824 | 9009 ± 3548 |
| 4 | | REGN6581 (50 mg/kg) | 1.4 ± 0.3 | 4715 ± 907 | 7341 ± 2549 |

Telemetered normotensive NPR1$^{hu/hu}$ mice were randomized into four groups of equal body weight and given a single subcutaneous injection of R5381 followed by a dose of a reversal agent at the doses listed in Table 18. Urine was collected overnight beginning on study day 21 and ending on study day 22. All values are mean ± SEM, n = 3-5 per group. Statistics - one-way ANOVA with Dunnett's; *p < 0.05 vs. Group 2 R5381 + Isotype Control).

cGMP production was not affected by administration of the reversal agents when assessed in the urine at day 22 (Table 22).

Both bivalent anti-R5381 antibodies REGN6580 and REGN6581 rapidly and persistently reversed the blood pressure-lowering effects of R5381 through study day 21 following the single intravenous injection on study day 3 to normotensive NPR1$^{hu/hu}$ mice that had received a single dose of R5381.

Example 12

Evaluation of Reversal of R5381-Induced Blood Pressure Lowering Using a Single 50 mg/kg Subcutaneous Dose of Bivalent Anti-R5381 mAbs in Normotensive NPR1$^{hu/hu}$ Mice In order to assess the effects of bivalent anti-R5381 antibodies at reversing the blood pressure lowering induced by R5381 in telemetered normotensive NPR1$^{hu/hu}$ mice, male NPR1$^{hu/hu}$ (n=20) mice aged ~10-12 weeks were implanted with PA-C10 telemeters (DSI, St. Paul, MN) and allowed to recover for at least 7 days. Animals were stratified into groups (Groups 1-4) based on pre-study systolic blood pressures and body weight. Animals were individually housed under standard conditions (Temperatures of 64° F. to 84° F. (18° C. to 29° C.); relative humidity of 30% to 70%) and a 12-hour light/12-hour dark cycle was maintained. Food (Research Diets Standard pellet chow) and water were provided ad libitum.

The test proteins were administered to the appropriate animals by single subcutaneous injection on Day 0. The rescue agents were administered to the appropriate animals by single subcutaneous injection on Day 3. The dose volume for each animal was based on the most recent body weight measurement.

TABLE 23

Summary of Doses and Dose Groups

| Group No. | Test Article | Dose (mg/kg s.c.) | Rescue Article | Dose (mg/kg s.c.) | Number of Animals Males |
|---|---|---|---|---|---|
| 1 | PBS | 0 | PBS | 0 | 5 |
| 2 | REGN5381 | 5 | IgG4P isotype control mAb | 50 | 5 |
| 3 | | | REGN6580 | 5 | |
| 4 | | | REGN6581 | 5 | |

Systolic pressure, diastolic pressure, pulse pressure, mean arterial pressure and heart rate were collected for 10 seconds every 10 minutes for the duration of the testing period. Data were binned and assessed accordingly for acute (hourly bins) and chronic (24-hr bins) reversal of R5381-induced blood pressure lowering. Day 21/22 cyclic guanosine monophosphate (cGMP) concentrations in urine were assessed by ELISA. All data are presented as mean±SEM.

Results

Figure 7:
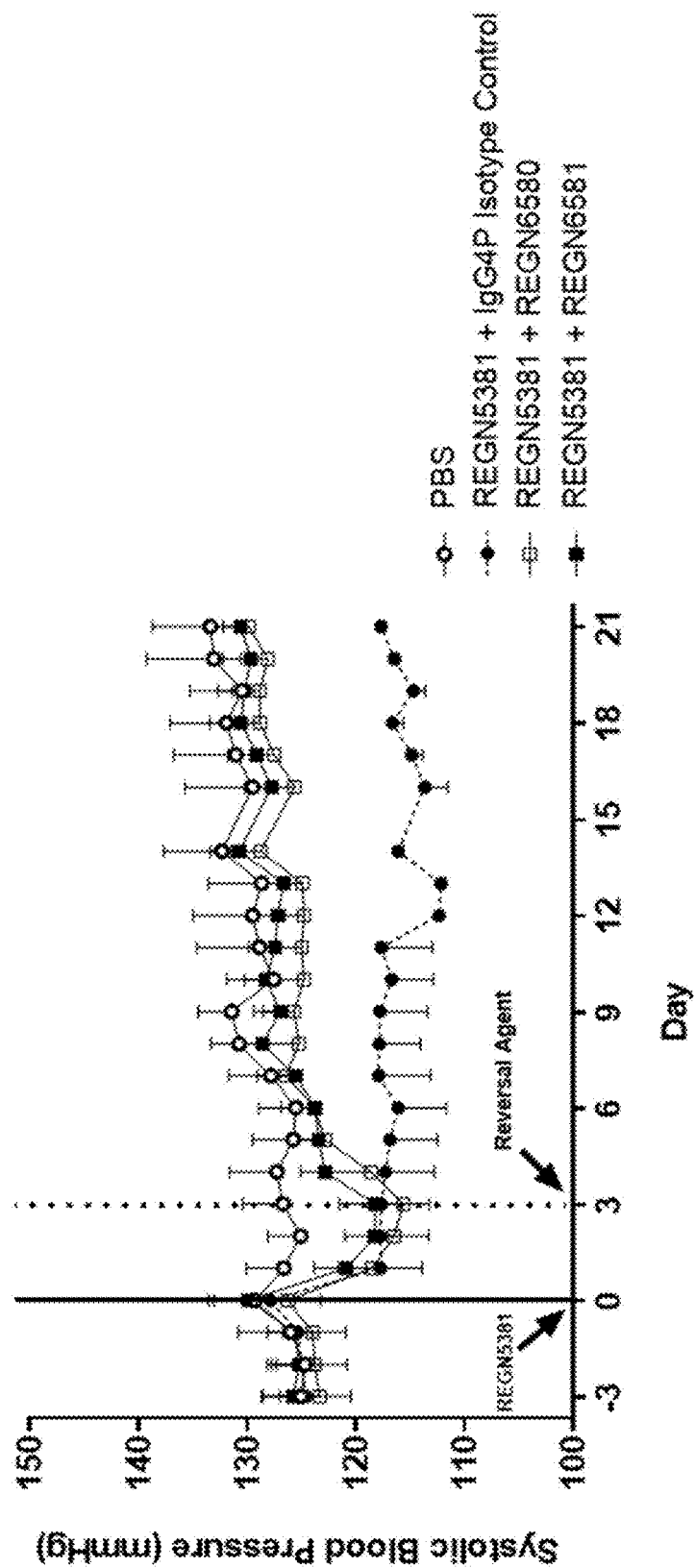
FIG. 7 shows, in line graph form, the effects of bivalent anti-R5381 mAbs on reversing R5381-induced systolic blood pressure-lowering in normotensive NPR1$^{hu/hu}$ mice. Telemetered normotensive NPR1$^{hu/hu}$ mice were randomized into groups based off of systolic blood pressures and body weight. Animals were given a single 5 mg/kg subcutaneous injection of R5381 as described in Table 23.

The in vivo screen of bivalent anti-R5381 antibodies demonstrated persistent reversal of the blood pressure lowering effects of R5381 (FIG. 7 and Table 24, below).

TABLE 24

Day 1-2 - Mean Blood Pressures and Heart Rates Prior to Administration of Rescue Agent

| Group | Test Article: | Systolic (mmHg) | Diastolic (mmHg) | Pulse Pressure (mmHg) | Mean Arterial (mmHg) | Heart Rate (BPM) |
|---|---|---|---|---|---|---|
| 1 | PBS | 126 ± 1 | 91 ± 0 | 34 ± 1 | 109 ± 1 | 522 ± 5 |
| 2 | R5381 | 118 ± 0** | 90 ± 0 | 28 ± 0** | 104 ± 0 | 538 ± 7 |
| 3 | | 118 ± 1** | 91 ± 1 | 27 ± 1*** | 105 ± 1 | 539 ± 10 |
| 4 | | 119 ± 1* | 92 ± 2 | 28 ± 0** | 106 ± 1 | 521 ± 11 |

Telemetered normotensive NPR1$^{hu/hu}$ mice were randomized into groups based on systolic blood pressures and body weight. Animals were given a single 5 mg/kg subcutaneous injection of NPR1 agonist mAb R5381 or PBS as described in Table 23. All values are mean ± SEM, n = 4-5 per group. Statistics - one-way ANOVA with Dunnett's; *p < 0.05 vs. PBS; p < 0.01 vs. PBS; *p < 0.001 vs. PBS.

Both REGN6580 and REGN6581, when administered subcutaneously 3 days after initial dosing of R5381, were able to increase pressures back to baseline levels (FIG. 7 and Table 25, below).

TABLE 25

Day 4-20 Mean Blood Pressures and Heart Rates Following Administration of Rescue Agent

| Group | Test Article: | Rescue Article | Systolic (mmHg) | Diastolic (mmHg) | Pulse Pressure (mmHg) | Mean Arterial (mmHg) | Heart Rate (BPM) |
|---|---|---|---|---|---|---|---|
| 1 | PBS | PBS | 130 ± 1**** | 95 ± 0**** | 35 ± 0**** | 113 ± 1**** | 523 ± 4 |
| 2 | R5381 | isotype control mAb | 116 ± 0 | 88 ± 0 | 28 ± 0 | 102 ± 0 | 524 ± 3 |
| 3 | | REGN6580 | 126 ± 1**** | 92 ± 0**** | 34 ± 0**** | 109 ± 1**** | 501 ± 3**** |
| 4 | | REGN6581 | 127 ± 1**** | 93 ± 1**** | 34 ± 0**** | 111 ± 1**** | 494 ± 4**** |

Telemetered normotensive NPR1$^{hu/hu}$ mice were randomized into groups based on systolic blood pressures and body weight. Animals were given a single 5 mg/kg subcutaneous injection of NPR1 agonist mAb R5381 or isotype control mAb as described in Table 23. All values are mean ± SEM, n = 4-5 per group. Statistics - one-way ANOVA with Dunnett's; ****p < 0.0001 vs. Isotype Control.

The durability of reversal was maintained for the 22-day duration of the study, with statistically significant differences in all hemodynamic parameters for animals dosed with REGN6580 or REGN6581 when compared to animals administered R5381 and isotype control mAb (FIG. 7 and Table 25). When compared to PBS control animals, no statistically significant differences were noted (Table 25, FIG. 7) following administration of either REGN6580 or REGN6581, indicating full and persistent reversal of R5381-induced blood pressure-lowering effects.

Both REGN6580 and REGN6581 demonstrated attenuation of NPR1 signaling as indicated by the statistically significant reduction of cGMP levels in the urine following subcutaneous administration of either REGN6580 or REGN6581 22 days later (Table 26, below).

TABLE 26

Day 22 Urine Volumes and Urinary cGMP Levels

| Group | Test Article: | Reversal Agent | Urine Volume (mL/day)g) | Urinary cGMP (pmol/mL) | Urinary cGMP (pmol/day) |
|---|---|---|---|---|---|
| 1 | PBS | PBS | 1.3 ± 0.2 | 2699 ± 223* | 3844 ± 969* |
| 2 | R5381 (5 mg/kg) | Isotype Control (50 mg/kg) | 1.7 ± 0.2 | 6781 ± 2079 | 11500 ± 3795 |
| 3 | | REGN6580 (50 mg/kg) | 1.1 ± 0.1 | 2932 ± 435* | 3312 ± 738* |
| 4 | | REGN6581 (50 mg/kg) | 1.9 ± 0.5 | 3165 ± 370** | 6305 ± 2367 |

Telemetered normotensive NPR1$^{hu/hu}$ mice were randomized into four groups of equal body weight and given a single subcutaneous injection of R5381 followed by a subcutaneous dose of a reversal agent at the doses listed in TABLE 23. Urine was collected overnight beginning on study day 21 and ending on study day 22. All values are mean ± SEM, n = 3-5 per group. Statistics - one-way ANOVA with Dunnett's; *p < 0.05 vs. Group 2 R5381 + Isotype Control).

A trending non-statistically significant reduction in absolute and relative heart weight was observed with administration of R5381 and isotype control (Table 27, below).

TABLE 27

Gross and Relative Heart Weight Following Administration of Reversal Agent

| Group | Heart Weight (mg) | Brain Weight (mg) | Tibia Length (mm) | Heart Weight: Brain Weight | Heart Weight: Tibia Length |
|---|---|---|---|---|---|
| PBS + PBS | 126 ± 8 | 427 ± 7 | 17.6 ± 0.2 | 0.294 ± 0.015 | 0.007 ± 0.0004 |
| R5381 + isotype control mAb | 120 ± 15 | 442 ± 3 | 18.0 ± 0.1 | 0.271 ± 0.032 | 0.007 ± 0.0009 |
| R5381 + REGN6580 | 126 ± 8 | 437 ± 4 | 17.8 ± 0.2 | 0.288 ± 0.018 | 0.007 ± 0.0004 |
| R5381 + REGN6581 | 126 ± 6 | 452 ± 7 | 17.9 ± 0.2 | 0.280 ± 0.012 | 0.007 ± 0.0004 |

Telemetered normotensive NPR1$^{hu/hu}$ mice were randomized into groups based on systolic blood pressures and body weight. Animals were given a single 5 mg/kg subcutaneous injection of NPR1 agonist mAb R5381 or isotype control as described in TABLE 23. All values are mean ± SEM, n = 4-5 per group. Statistics - one-way ANOVA with Dunnett's.

This change is likely attributed to the hemodynamic effects of R5381. Although not significant, animals that received R5381 followed by either REGN6580 or REGN6581 had absolute and relative heart weights closer to control animals, aligned with mitigation of R5381-induced hemodynamic effects.

Following a single subcutaneous injection on study day 3, both bivalent anti-R5381 antibodies, REGN6580 and REGN6581, rapidly and persistently reversed the blood pressure-lowering effects of R5381 as assessed in telemetered normotensive NPR1$^{hu/hu}$ mice. Both agents also functioned to inhibit NPR1-induced cGMP production through study day 22.

Example 13

Evaluation of Reversal of R5381-Induced Blood Pressure Lowering Using a Single 50 mg/kg Dose of Monovalent Anti-R5381 mAbs in Normotensive NPR1$^{hu/hu}$ Mice In an effort to assess the effects of monovalent anti-R5381 antibodies at reversing the blood pressure lowering induced by R5381 in telemetered normotensive NPR1$^{hu/hu}$ mice, male NPR1$^{hu/hu}$ (n=48) mice aged ~13-14 weeks were implanted with PA-C10 telemeters (DSI, St. Paul, MN) and allowed to recover for at least 7 days. Animals were stratified into groups (Table 28, below) (Groups 1-8) based on pre-study systolic blood pressures and body weight (Table 29, below).

TABLE 28

Summary of Doses and Dose Groups

| Group No. | Test Article | Dose (mg/kg s.c.) | Rescue Article | Rescue Dose (mg/kg) | Rescue Dose Route | Number of Animals Males |
|---|---|---|---|---|---|---|
| 1 | PBS | 0 | PBS | 0 | i.v. | 6 |
| 2 | REGN5381 | 5 | IgG4P isotype control mAb | 50 | s.c. | 6 |
| 3 | | | REGN6580 | | | 6 |
| 4 | | | REGN9035 | | | 6 |
| 5 | | | REGN9037 | | i.v. | 6 |
| 6 | | | REGN6580 | | | 6 |
| 7 | | | REGN9035 | | | 6 |
| 8 | | | REGN9037 | | | 6 |

TABLE 29

Day 1-2 - Mean Blood Pressures and Heart Rates Prior to Administration of Rescue Agent

| Group | Test Article: | Systolic (mmHg) | Diastolic (mmHg) | Pulse Pressure (mmHg) | Mean Arterial (mmHg) | Heart Rate (BPM) |
|---|---|---|---|---|---|---|
| 1 | PBS | 123 ± 0 | 89 ± 0 | 34 ± 0 | 107 ± 0 | 545 ± 5 |
| 2 | R5381 | 120 ± 0*** | 90 ± 0 | 30 ± 0*** | 106 ± 0* | 582 ± 2**** |
| 3 | | 120 ± 0*** | 91 ± 1 | 29 ± 0*** | 106 ± 0 | 556 ± 3* |
| 4 | | 116 ± 0**** | 88 ± 0 | 28 ± 0**** | 103 ± 0**** | 574 ± 0*** |
| 5 | | 117 ± 0**** | 89 ± 0 | 28 ± 0**** | 104 ± 0*** | 565 ± 2** |
| 6 | | 117 ± 0**** | 88 ± 0 | 28 ± 1**** | 104 ± 0**** | 565 ± 1** |
| 7 | | 116 ± 0**** | 89 ± 1 | 28 ± 0**** | 104 ± 0*** | 555 ± 1 |
| 8 | | 118 ± 0**** | 88 ± 0 | 29 ± 1*** | 104 ± 0*** | 543 ± 2 |

Telemetered normotensive NPR1$^{hu/hu}$ mice were randomized into groups based on systolic blood pressures and body weight. Animals were given a single 5 mg/kg subcutaneous injection of NPR1 agonist mAb R5381 or PBS as described in Table 28. All values are mean ± SEM, n = 4-5 per group. Statistics - one-way ANOVA with Dunnett's; *p < 0.05 vs. PBS; p < 0.01 vs. PBS; *p < 0.001 vs. PBS; ****p < 0.0001 vs. PBS.

Animals were individually housed under standard conditions (Temperatures of 64° F. to 84° F. (18° C. to 29° C.); relative humidity of 30% to 70%) and a 12-hour light/12-hour dark cycle was maintained. Food (Research Diets Standard pellet chow) and water were provided ad libitum.

Test proteins were administered to the appropriate animals by single subcutaneous injection on Day 0. The rescue agents were administered to the appropriate animals by single subcutaneous or intravenous injection on Day 3. The dose volume for each animal was based on the most recent body weight measurement. Overnight collection of urine was performed on study days 20 and 21.

Systolic pressure, diastolic pressure, pulse pressure, mean arterial pressure and heart rate were collected for 10 seconds every 10 minutes for the duration of the testing period. Data were binned and assessed accordingly for acute (hourly bins) and chronic (24-hr bins) reversal of R5381-induced blood pressure lowering. Day 21/22 cyclic guanosine monophosphate (cGMP) concentrations in urine were assessed by ELISA. All data are presented as mean±SEM.

Results

The in vivo screen of monovalent anti-R5381 antibodies demonstrated rapid and persistent reversal of the blood pressure-lowering effects of R5381 (Table 30, below; FIG. 8 and FIG. 9).

TABLE 30

Day 4-20 Mean Blood Pressures and Heart Rates Following Administration of Rescue Agent

| Group | Test Article: | Rescue Article | Rescue Dose Route | Systolic (mmHg) | Diastolic (mmHg) | Pulse Pressure (mmHg) | Mean Arterial (mmHg) | Heart Rate (BPM) |
|---|---|---|---|---|---|---|---|---|
| 1 | PBS | PBS | i.v. | 125 ± 0**** | 90 ± 0** | 34 ± 0**** | 109 ± 0**** | 534 ± 2**** |
| 2 | R5381 | isotype control mAb | s.c. | 119 ± 0 | 88 ± 0 | 31 ± 0 | 105 ± 0 | 550 ± 3 |
| 3 | | REGN6580 | | 130 ± 0**** | 94 ± 0**** | 36 ± 0**** | 113 ± 0**** | 522 ± 2**** |
| 4 | | REGN9035 | | 125 ± 0**** | 91 ± 0**** | 34 ± 0**** | 109 ± 0**** | 550 ± 2 |
| 5 | | REGN9037 | | 126 ± 0**** | 92 ± 0**** | 35 ± 0**** | 110 ± 0**** | 531 ± 2**** |
| 6 | | REGN6580 | i.v. | 129 ± 1**** | 94 ± 1**** | 34 ± 0**** | 113 ± 1**** | 524 ± 2**** |

TABLE 30-continued

Day 4-20 Mean Blood Pressures and Heart Rates Following Administration of Rescue Agent

| Group | Test Article: | Rescue Article | Rescue Dose Route | Systolic (mmHg) | Diastolic (mmHg) | Pulse Pressure (mmHg) | Mean Arterial (mmHg) | Heart Rate (BPM) |
|---|---|---|---|---|---|---|---|---|
| 7 | | REGN9035 | | 126 ± 0**** | 92 ± 0**** | 34 ± 0**** | 110 ± 0**** | 528 ± 2**** |
| 8 | | REGN9037 | | 129 ± 1**** | 92 ± 1**** | 37 ± 0**** | 111 ± 1**** | 514 ± 2**** |

Telemetered normotensive NPR1$^{hu/hu}$ mice were randomized into groups based on systolic blood pressures and body weight. Animals were given a single 5 mg/kg subcutaneous injection of NPR1 agonist mAb R5381 or PBS as described in Table 28. All values are mean ± SEM, n = 4-5 per group. Statistics - one way ANOVA with Dunnett's; *p < 0.05 vs. Isotype Control; p < 0.01 vs. Isotype Control; *p < 0.001 vs. Isotype Control; ****p < 0.0001 vs. Isotype Control.

Both REGN9035 and REGN9037, when administered intravenously or subcutaneously 3 days after initial dosing of R5381, were able to increase pressures back to baseline levels (Table 30; FIG. 8 and FIG. 9). The initial drop in absolute pressure of 3-6 mmHg (Table 29) and relative pressure of ~10 mmHg (FIG. 8) compared to time-matched controls was reversed within hours following intravenous dosing of REGN9035, REGN9037 or REGN6580 (FIG. 9). Subcutaneous delivery of REGN9035, REGN9037 or REGN6580 achieved full reversal within 24 hours following reversal agent administration (FIG. 9). The durability of reversal was maintained for the 20-day duration of the study, with statistically significant differences in all hemodynamic parameters for animals dosed with REGN9035 or REGN9037 when compared to animals administered R5381 and isotype control mAb (Table 30, FIG. 8). When compared to PBS control animals, no statistically significant difference was noted (Table 30, FIG. 8) following administration of either REGN9035, REGN9037, or REGN6580 indicating full and persistent reversal of R5381-induced blood pressure lowering effects. The reduced pressures induced by R5381 resulted in smaller heart weights (Table 31, below), likely the result of reduced left ventricular afterload induced by NPR1 agonism.

TABLE 31

Absolute and Relative Heart Weights

| Group | Test Article: | Rescue Article | Rescue Dose Route | Heart Weight (mg) | Brain Weight (mg) | Tibia Length (mm) | Heart Weight: Brain Weight | Heart Weight: Tibia Length |
|---|---|---|---|---|---|---|---|---|
| 1 | PBS | PBS | i.v. | 126 ± 0 | 482 ± 0 | 17.4 ± 0 | 0.26 ± 0 | 7.2 ± 0 |
| 2 | R5381 | isotype control mAb | s.c. | 112 ± 0 | 481 ± 0 | 17.8 ± 0 | 0.23 ± 0 | 6.3 ± 0 |
| 3 | | REGN6580 | | 128 ± 0 | 476 ± 0 | 17.6 ± 0 | 0.27 ± 0* | 7.3 ± 0* |
| 4 | | REGN9035 | | 126 ± 0 | 463 ± 0 | 17.6 ± 0 | 0.27 ± 0* | 7.1 ± 0 |
| 5 | | REGN9037 | | 133 ± 0* | 468 ± 0 | 17.8 ± 0 | 0.28 ± 0** | 7.5 ± 0** |
| 6 | | REGN6580 | i.v. | 120 ± 0 | 472 ± 1 | 17.7 ± 0 | 0.25 ± 1 | 6.8 ± 0 |
| 7 | | REGN9035 | | 125 ± 0 | 476 ± 0 | 17.8 ± 0 | 0.26 ± 0 | 7.0 ± 0 |
| 8 | | REGN9037 | | 125 ± 0 | 463 ± 1 | 17.4 ± 0 | 0.27 ± 1* | 7.2 ± 0 |

Telemetered normotensive NPR1$^{hu/hu}$ mice were randomized into groups based on systolic blood pressures and body weight. Animals were given a single 5 mg/kg subcutaneous injection of NPR1 agonist mAb R5381 or PBS as described in Table 28. All values are mean ± SEM, n = 4-5 per group. Statistics - one-way ANOVA with Dunnett's; *p < 0.05 vs. Isotype Control; **p < 0.01 vs. vs. Isotype Control.

The myocardial structural changes were ameliorated (Table 31) following administration of any of the reversal agents, REGN9035, REGN9037 or REGN6580. Finally, all anti-R5381 mAbs demonstrated attenuation of NPR1 signaling as indicated by the statistically significant reduction of cGMP with subcutaneous or intravenous administration 22 days later (FIG. 10).

Both bivalent and monovalent anti-R5381 antibodies REGN6580, and REGN9035 and REGN9037, respectively, rapidly and persistently reversed the blood pressure-lowering effects of R5381 and inhibited NPR1-induced cGMP production through study day 21 following the single subcutaneous or intravenous injection on study day 3 to normotensive NPR1$^{hu/hu}$ mice that had received a single dose of R5381.

Example 14

Midodrine Rescue Following a Single Intravenous Dose of R5381 in Telemetered Cynomolgus Monkeys An in vivo study was performed to evaluate the alpha-adrenergic receptor agonist, midodrine, as an effective agent to transiently reverse the blood pressure lowering effects of R5381 in cynomolgus monkeys. Animals received a single IV bolus of 25 mg/kg R5381 and 3 days later were administered 3 doses of 2.5 mg/kg midodrine by oral gavage with 3 to 4 hours between each dose. Animals were monitored for 4 days post R5381 dosing, including 1 day post midodrine dosing, to assess for hemodynamic changes; pre-dose measurements served as the baseline for each animal. Midodrine transiently reversed the R5381-induced reductions in mean systolic blood pressure to time-matched control levels. Midodrine also transiently reversed the R5381-induced elevations in mean heart rate and resulted in a mean reduction from baseline heart rate in R5381-dosed animals.

Specifically, the evaluation of the utility of administration of a vasopressor as an agent to transiently reverse the blood pressure effects of R5381 in normotensive telemetered male cynomolgus monkeys is particularly relevant to clinical settings in which a patient on R5381 may need to have their blood pressure increased (e.g., shock-induced hypotension). Prior to dose administration, each animal was surgically implanted with a radio telemetry transmitter. On Day 0, animals each received a single IV bolus of saline (PBS; n=10) or 25 mg/kg R5381 (n=13). On Day 3, animals each received three 2.5 mg/kg doses of the alpha-adrenergic receptor agonist, midodrine, (n=6 for saline group; n=7 for R5381 group) or water/vehicle (n=4 for saline group; n=6 for R5381 group) administered by oral gavage, with each dose spaced 3 to 4 hours apart. Animals were monitored for 48 hours to assess for cardiovascular hemodynamic changes. Blood pressure and heart rate measurements were collected for each animal from Day −3 pre-R5381-dose through Day 4 post-R5381-dose. Pre-dose measurements served as the baseline for each animal.

Results

Midodrine Reversed the Blood Pressure and Heart Rate Effects of R5381 in Cynomolgus Monkeys. Three doses of midodrine transiently reversed the R5381-induced reductions in mean systolic blood pressure, with the R5381-dosed animals that received midodrine exhibiting similar mean changes from baseline systolic blood pressure compared to those observed in saline-dosed animals that did not receive midodrine (FIG. 11).

In addition, the 3 doses of midodrine reversed the R5381-induced elevations in mean heart rate. The administration of midodrine resulted in a mean reduction from baseline heart rate in R5381-dosed animals; a similar effect was observed in saline-dose animals that were administered midodrine (FIG. 12).

The present disclosure is not to be limited in scope by the specific embodiments described herein. Indeed, various modifications in addition to those described herein will become apparent to those skilled in the art from the foregoing description and the accompanying figures. Such modifications are intended to fall within the scope of the appended claims.

What is claimed is:

1. An agent that reverses a reduction in blood pressure associated with the administration of a natriuretic peptide receptor 1 (NPR1) agonist, wherein the agent binds to the NPR1 agonist, wherein the agent is an immunoglobulin protein, wherein the immunoglobulin protein comprises three heavy chain complementarity determining regions (CDRs) HCDR1, HCDR2, and HCDR3 contained within a heavy chain variable region (HCVR) and three light chain CDRs LCDR1, LCDR2 and LCDR3 contained within a light chain variable region (LCVR), wherein the immunoglobulin protein comprises the HCVR comprising the amino acid sequence of SEQ ID NO: 2 and the LCVR comprising the amino acid sequence of SEQ ID NO: 10 or the HCVR comprising the amino acid sequence of SEQ ID NO: 22 and the LCVR comprising the amino acid sequence of SEQ ID NO: 30.

2. The agent of claim 1, wherein the NPR1 agonist is an antibody or antigen-binding fragment thereof that binds specifically to NPR1, wherein the antibody or antigen-binding fragment thereof comprises three heavy chain CDRs HCDR1, HCDR2, and HCDR3 contained within a HCVR comprising SEQ ID NO: 48; and three light chain CDRs LCDR1, LCDR2 and LCDR3 contained within a LCVR comprising SEQ ID NO: 52.

3. The agent of claim 2, wherein the antibody or antigen-binding fragment thereof comprises three heavy chain CDRs HCDR1, HCDR2, and HCDR3 comprising SEQ ID NOs: 49, 50, and 51, respectively; and three light chain CDRs LCDR1, LCDR2 and LCDR3 comprising SEQ ID NOs: 53, 54, and 55, respectively.

4. The agent of claim 3, wherein the antibody or antigen-binding fragment thereof comprises a HCVR of SEQ ID NO: 48 and a LCVR of SEQ ID NO: 52.

5. The agent of claim 2, wherein the antibody or antigen-binding fragment thereof is a monoclonal antibody.

6. The agent of claim 5, wherein the antibody is an IgG1 antibody.

7. The agent of claim 5, wherein the antibody is an IgG4 antibody.

8. The agent of claim 5, wherein the antibody comprises a heavy chain comprising SEQ ID NO: 56 and a light chain comprising SEQ ID NO: 57.

9. The agent of claim 1, wherein the NPR1 agonist is R5381.

10. The agent of claim 1, wherein the immunoglobulin protein comprises three heavy chain CDRs HCDR1, HCDR2, and HCDR3 and three light chain CDRs LCDR1, LCDR2 and LCDR3 comprising amino acid sequences selected from SEQ ID NOs: 4, 6, 8, 12, 14 and 16; or SEQ ID NOs: 24, 26, 28, 32, 34, and 36.

11. The agent of claim 10, wherein the HCVR comprises an amino acid sequence having at least 90%, 95%, 98%, or 99% sequence identity to the sequence of SEQ ID NOs: 2 or the sequence of SEQ ID NO: 22.

12. The agent of claim 10, wherein the LCVR comprises an amino acid sequence having at least 90%, 95%, 98%, or 99% sequence identity to the sequence of SEQ ID NOs: 10 or the sequence of SEQ ID NO: 30.

13. The agent of claim 10, wherein the HCVR comprises the amino acid sequence of SEQ ID NO: 2 and the LCVR comprises the amino acid sequence of SEQ ID NO: 10.

14. The agent of claim 10, wherein the HCVR comprises the amino acid sequence of SEQ ID NO: 22 and the LCVR comprises the amino acid sequence of SEQ ID NO: 30.

15. The agent of claim 1, wherein HCDR1-HCDR2-HCDR3-LCDR1-LCDR2-LCDR3 comprise amino acid sequences selected from the group consisting of (i) SEQ ID NOs: 4, 6, 8, 12, 14 and 16; and (ii) SEQ ID NOs: 24, 26, 28, 32, 34, and 36.

16. The agent of claim 15, wherein the HCVR comprises the amino acid sequence of SEQ ID NO: 2 and the LCVR comprises the amino acid sequence of SEQ ID NO: 10.

17. The agent of claim 15, wherein the HCVR comprises the amino acid sequence of SEQ ID NO: 22 and the LCVR comprises the amino acid sequence of SEQ ID NO: 30.

18. The agent of claim 1 wherein the immunoglobulin protein is comprised within a Fab fragment.

19. The agent of claim 18, further comprising a multimerizing component.

20. The agent of claim 19, wherein the multimerizing component comprises at least one Fc fragment.

21. The agent of claim 20, wherein the at least one Fc fragment is of isotype IgG1, IgG4, or a variant thereof.

22. The agent of claim 21, wherein the at least one Fc fragment is of IgG4 isotype.

23. The agent of claim 21, wherein the at least one Fc fragment is of IgG1 isotype.

24. The agent of claim 20, comprising a first Fc fragment and a second Fc fragment, wherein the first Fc fragment or the second Fc fragment, but not both Fc fragments, comprises a modification in the CH3 domain that reduces binding of the immunoglobulin protein to Protein A as compared to an immunoglobulin protein lacking the modification.

25. The agent of claim 24, wherein the modification comprises a H315R substitution and a Y316F substitution according to EU numbering in a Fc fragment.

26. The agent of claim 20, wherein the multimerizing component comprises a first Fc fragment comprising the amino acid sequence of SEQ ID NO: 46 and a second Fc fragment comprising the amino acid sequence of SEQ ID NO: 58.

27. The agent of claim 1, wherein the immunoglobulin protein is a monovalent monoclonal antibody.

28. The agent of claim 27, wherein the monovalent monoclonal antibody comprises a heavy chain comprising a amino acid sequence of SEQ ID NO: 42 or the amino acid sequence of SEQ ID NO: 44; and a light chain comprising the amino acid sequence of SEQ ID NO: 20 or the amino acid sequence of SEQ ID NO: 40.

29. The agent of claim 28, wherein the heavy chain comprises a modification in a CH3 domain that reduces binding of the immunoglobulin protein to Protein A.

30. The agent of claim 29, wherein the modification comprises a H315R substitution and a Y316F substitution according to EU numbering in the constant region of IgG1 or IgG4 isotype.

31. The agent of claim 28, wherein the immunoglobulin protein further comprises a Fc fragment.

32. The agent of claim 31, wherein the Fc fragment is of IgG1 or IgG4 isotype.

33. The agent of claim 31, wherein the Fc fragment comprises the amino acid sequence of SEQ ID NO: 46.

34. The agent of claim 1, wherein the agent is REGN9035 or REGN9037.

35. An isolated polynucleotide molecule comprising a polynucleotide sequence that encodes a HCVR of an immunoglobulin protein as in claim 33.

36. An isolated polynucleotide molecule comprising a polynucleotide sequence that encodes a LCVR of an immunoglobulin protein as in claim 33.

37. A vector comprising the polynucleotide molecule of claim 35 or the polynucleotide molecule of claim 36.

38. A host cell expressing the vector of claim 37.

39. A host cell expressing the polynucleotide molecule of claim 35 or the polynucleotide molecule of claim 36.

40. The host cell of claim 39, wherein the host cell is a CHO cell.

41. A pharmaceutical composition comprising the agent of claim 1 and a pharmaceutically acceptable carrier or diluent.

42. A method of reversing the hemodynamic effects of a NPR1 agonist, the method comprising administering a pharmaceutical composition comprising a therapeutically effective amount of the agent of claim 1 to a subject in need thereof.

43. The method of claim 42, wherein the composition is administered subcutaneously, intravenously, intradermally, intraperitoneally, or intramuscularly to the subject.

44. The method of claim 42, wherein the subject has a disease or disorder selected from the group consisting of hypertension, heart failure, and chronic kidney disease.

\* \* \* \* \*